(12) United States Patent
Shluzas et al.

(10) Patent No.: US 10,960,144 B2
(45) Date of Patent: Mar. 30, 2021

(54) SYSTEM AND METHOD FOR SAFETY SYRINGE

(71) Applicant: Credence MedSystems, Inc., Menlo Park, CA (US)

(72) Inventors: Alan E. Shluzas, San Carlos, CA (US); Stephen H. Diaz, Palo Alto, CA (US); John F. Shanley, Emerald Hills, CA (US); Scott Segelke, Mountain View, CA (US); John Merhige, Sudbury, MA (US)

(73) Assignee: Credence MedSystems, Inc., Menlo Park, CA (US)

( * ) Notice: Subject to any disclaimer, the term of this patent is extended or adjusted under 35 U.S.C. 154(b) by 192 days.

(21) Appl. No.: 15/801,304

(22) Filed: Nov. 1, 2017

(65) Prior Publication Data

US 2018/0133408 A1 May 17, 2018

Related U.S. Application Data

(60) Provisional application No. 62/416,102, filed on Nov. 1, 2016, provisional application No. 62/431,382, filed
(Continued)

(51) Int. Cl.
*A61M 5/32* (2006.01)
*A61M 5/178* (2006.01)
(Continued)

(52) U.S. Cl.
CPC .......... *A61M 5/3221* (2013.01); *A61M 5/178* (2013.01); *A61M 5/2066* (2013.01);
(Continued)

(58) Field of Classification Search
CPC .............. A61M 5/3221; A61M 5/2066; A61M 5/2448; A61M 5/284; A61M 5/3148;
(Continued)

(56) References Cited

U.S. PATENT DOCUMENTS 9,814,842 B2 11/2017 Diaz et al.
2008/0140005 A1 6/2008 Luo
(Continued)

FOREIGN PATENT DOCUMENTS

WO WO 89/09075 10/1989
WO WO 2015/164839 10/2015

OTHER PUBLICATIONS

PCT International Search Report for PCT/US2017/059617, Applicant: Credence MedSystems, Inc., Form PCT/ISA/210 and 220, dated May 4, 2018.
(Continued)

*Primary Examiner* — Tiffany Legette
(74) *Attorney, Agent, or Firm* — Vista IP Law Group, LLP

(57) ABSTRACT

A system for injecting includes a syringe body defining a proximal opening and a distal needle interface. The system also includes a plunger member defining a plunger interior and configured to be manually manipulated to insert a stopper member relative to the syringe body, the plunger member. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the syringe body. The needle assembly includes a needle having a needle proximal end feature, a hub, and a needle latching member configured to couple the needle to the hub. The needle is at least partially retractable into plunger interior. The needle proximal end feature includes an annular distally facing surface.

18 Claims, 72 Drawing Sheets

Related U.S. Application Data on Dec. 7, 2016, provisional application No. 62/480,276, filed on Mar. 31, 2017, provisional application No. 62/542,230, filed on Aug. 7, 2017.

(51) Int. Cl.
| | |
|---|---|
| *A61M 5/24* | (2006.01) |
| *A61M 5/20* | (2006.01) |
| *A61M 5/28* | (2006.01) |
| *A61M 5/315* | (2006.01) |
| *A61M 5/31* | (2006.01) |
| *A61J 1/20* | (2006.01) |

(52) U.S. Cl.
CPC ............ *A61M 5/2448* (2013.01); *A61M 5/28* (2013.01); *A61M 5/284* (2013.01); *A61M 5/3137* (2013.01); *A61M 5/3148* (2013.01); *A61M 5/31501* (2013.01); *A61M 5/31511* (2013.01); *A61M 5/31513* (2013.01); *A61M 5/3202* (2013.01); *A61M 5/322* (2013.01); *A61M 5/3234* (2013.01); *A61J 1/2006* (2015.05); *A61J 1/2096* (2013.01); *A61M 5/3232* (2013.01); *A61M 5/3293* (2013.01); *A61M 2005/323* (2013.01); *A61M 2005/3223* (2013.01); *A61M 2005/3231* (2013.01); *A61M 2005/3241* (2013.01)

(58) Field of Classification Search
CPC ............ A61M 5/31501; A61M 5/3234; A61M 5/3231; A61M 2005/323; A61M 2005/3241; A61M 5/178; A61M 5/28; A61M 5/3137; A61M 5/31511; A61M 5/31513; A61M 5/3202; A61M 5/333; A61M 5/3232; A61M 5/3293; A61M 2005/03; A61M 5/322; A61M 2005/3231; A61J 1/2006
See application file for complete search history.

(56) References Cited

U.S. PATENT DOCUMENTS

| | | |
|---|---|---|
| 2015/0005706 A1 | 1/2015 | Diaz |
| 2015/0148748 A1 | 5/2015 | Shluzas |
| 2016/0206834 A1 | 7/2016 | Shluzas |
| 2018/0117260 A1 | 5/2018 | Shluzas |
| 2018/0117261 A1 | 5/2018 | Steese-Bradley |

OTHER PUBLICATIONS

PCT Written Opinion of the International Search Authority for PCT/US2017/059617, Applicant: Credence MedSystems, Inc., Form PCT/ISA/237, dated May 4, 2018.
PCT International Preliminary Report on Patentability (Chapter I of the Patent Cooperation Treaty) for PCT/US2017/059617, Applicant: Credence MedSystems, Inc., Form PCT/ISA/326 and 373, dated May 16, 2019.

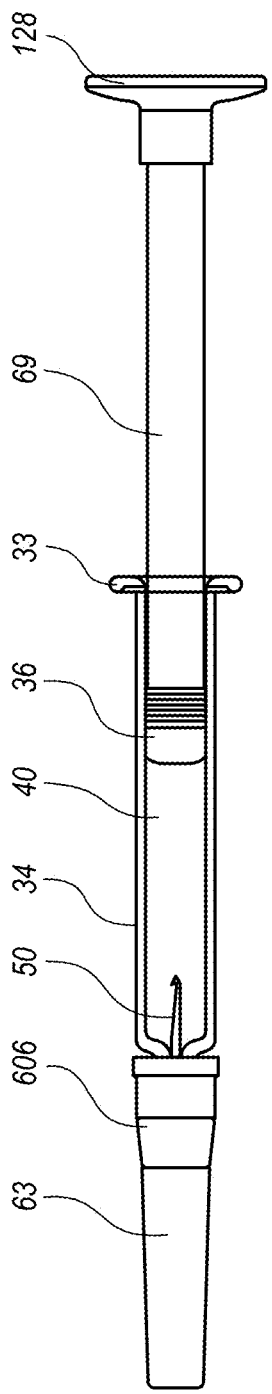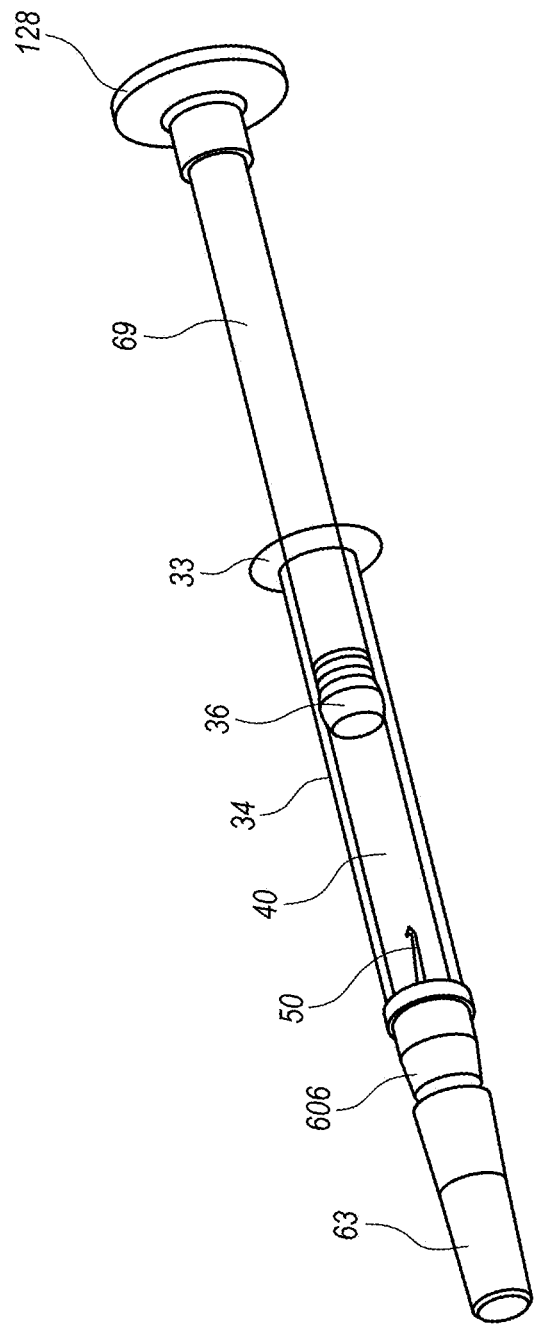
FIG. 6A
FIG. 6B

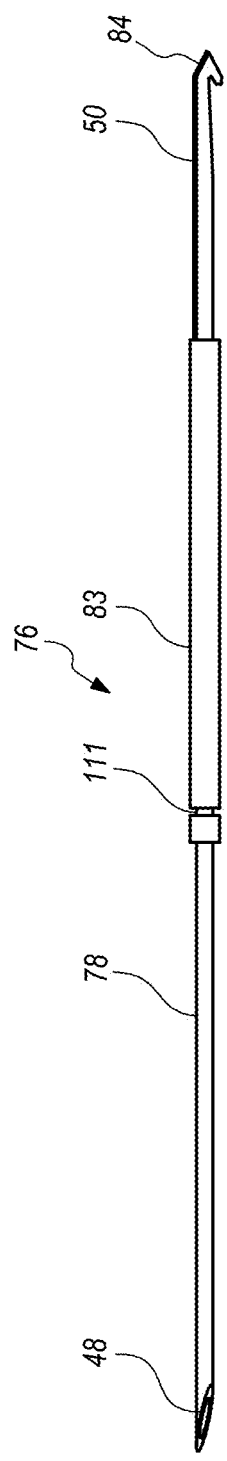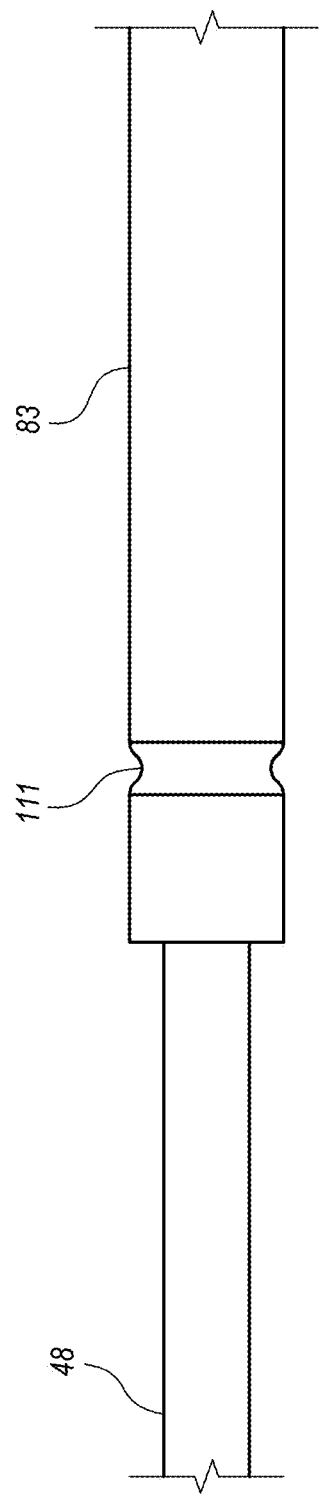

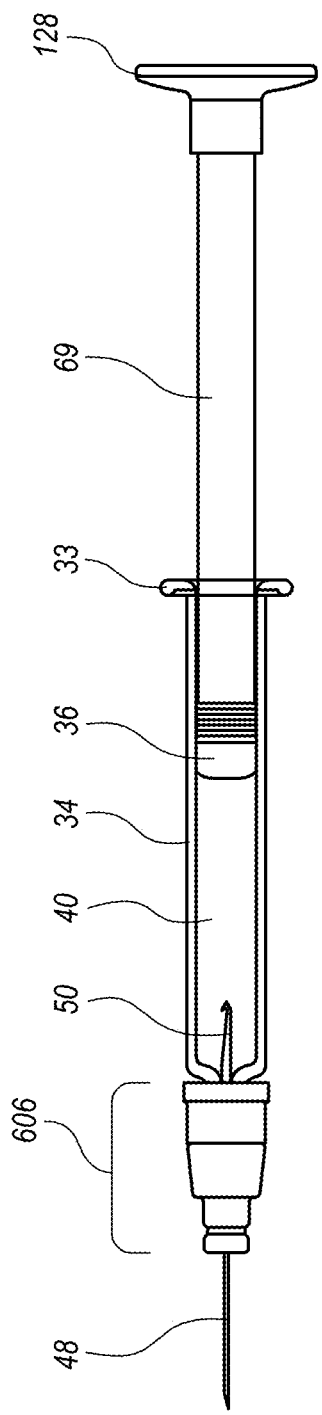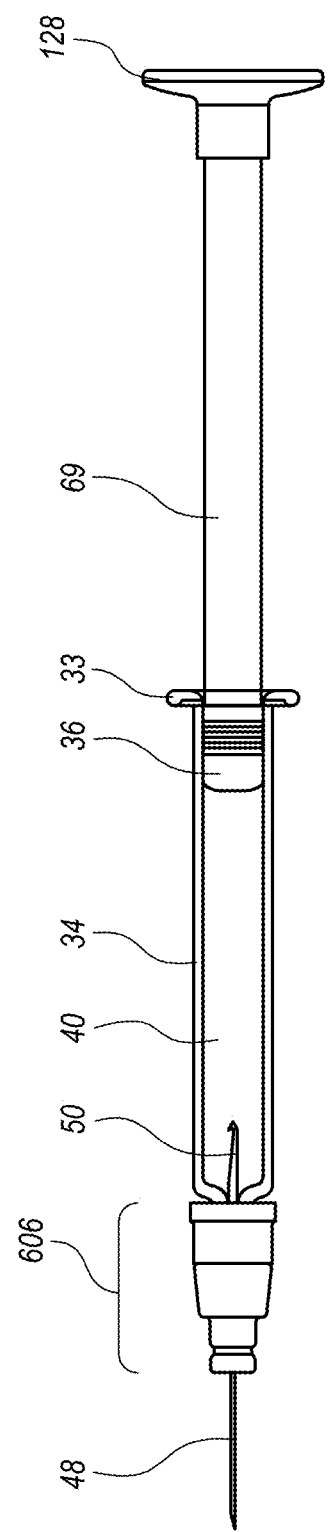

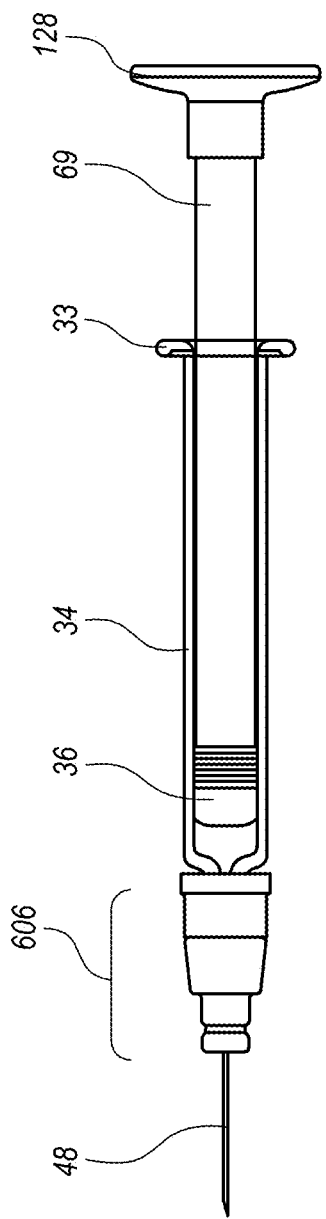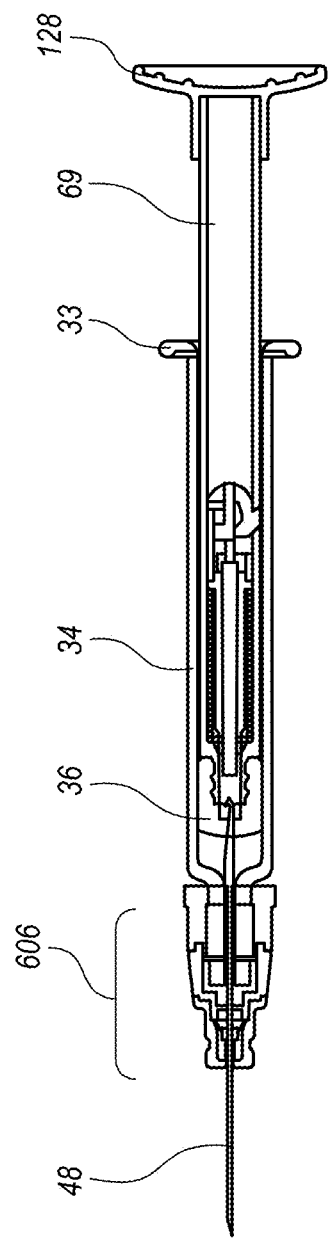

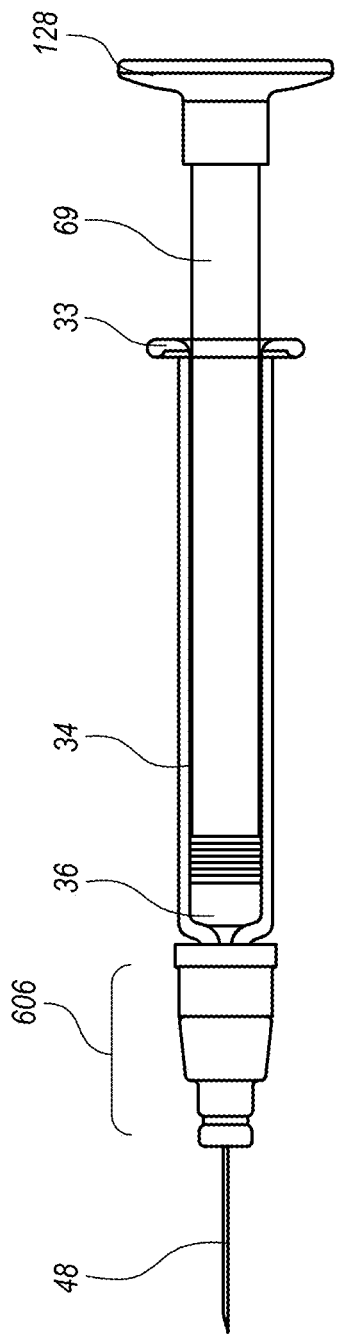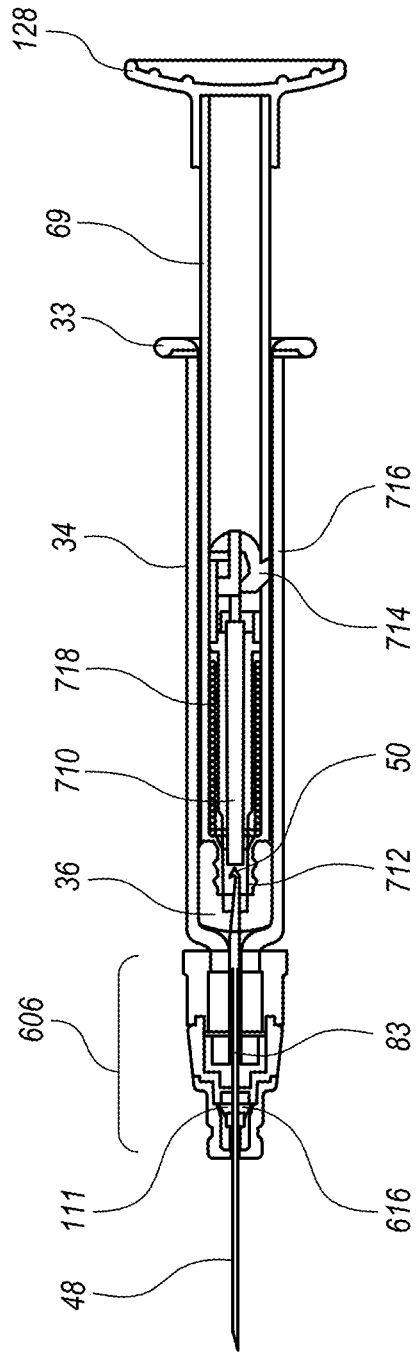
FIG. 6Q
FIG. 6R

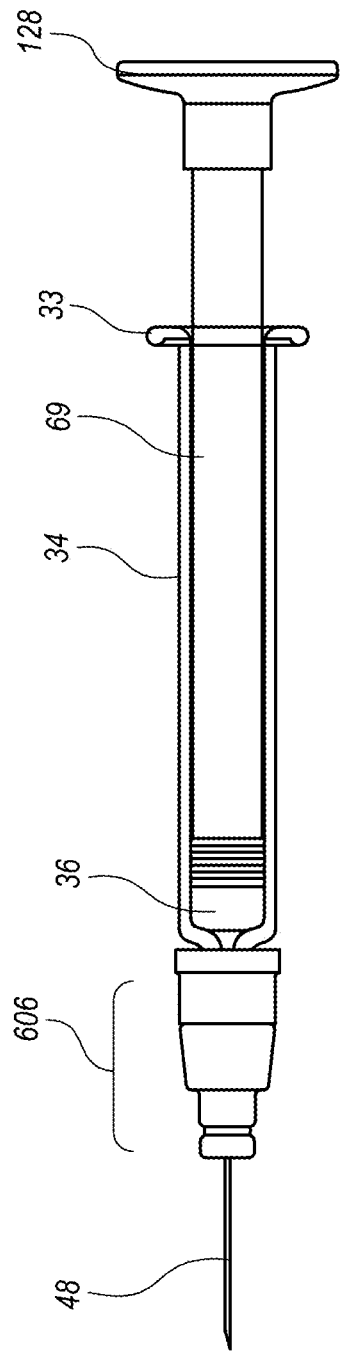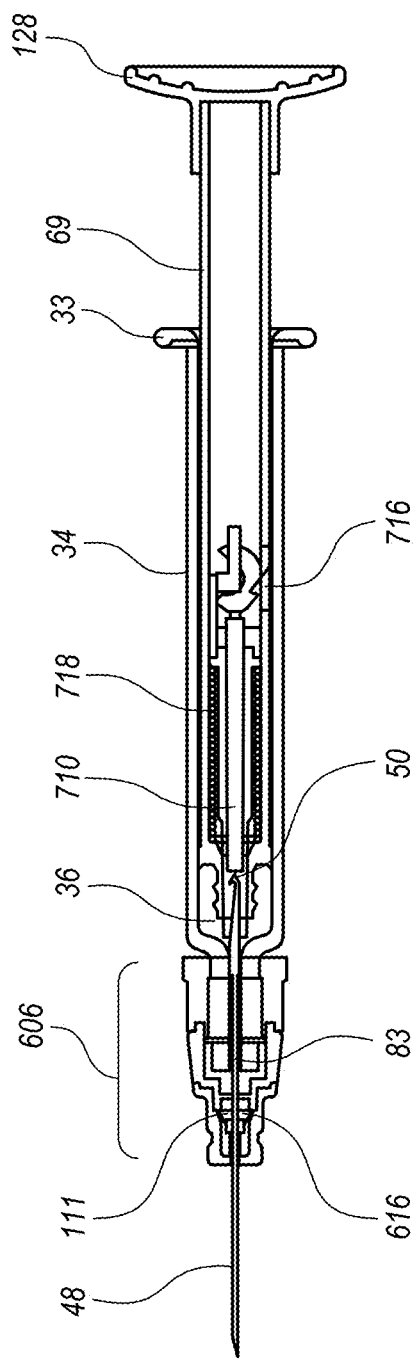

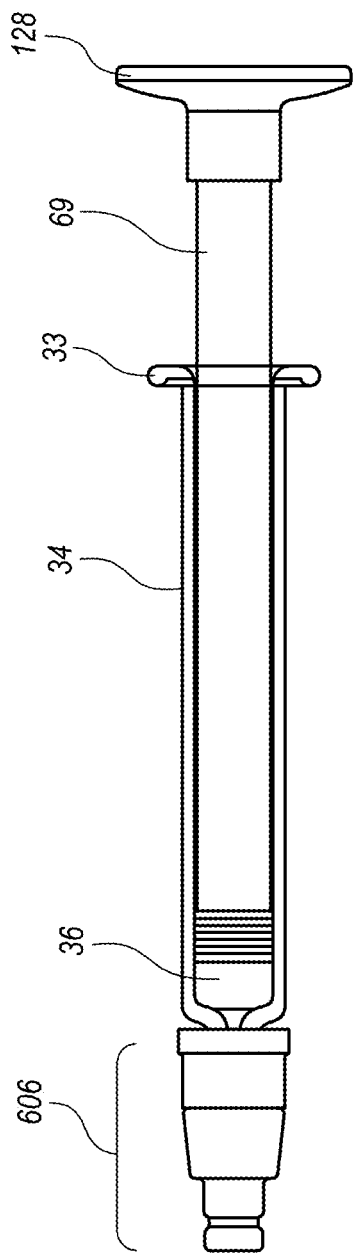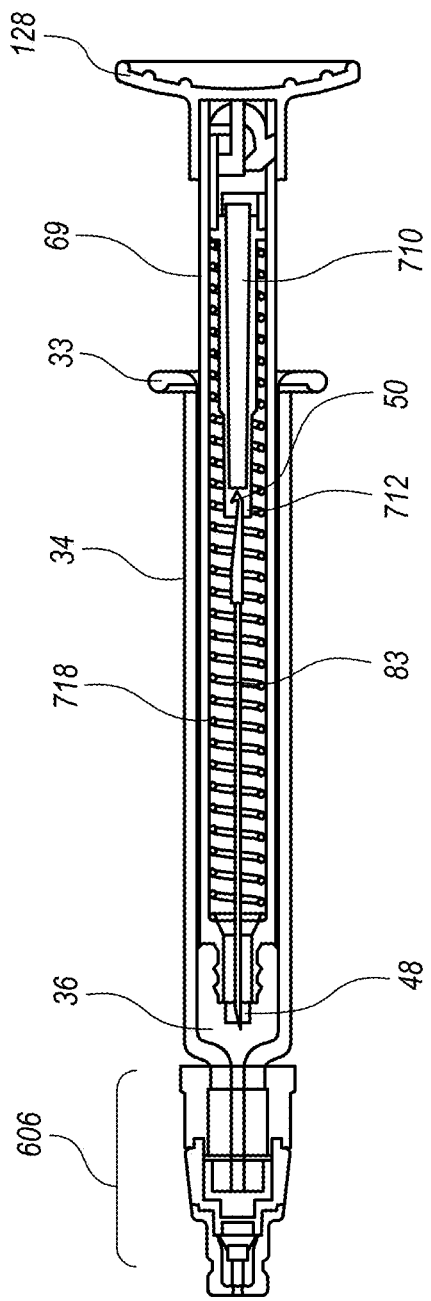

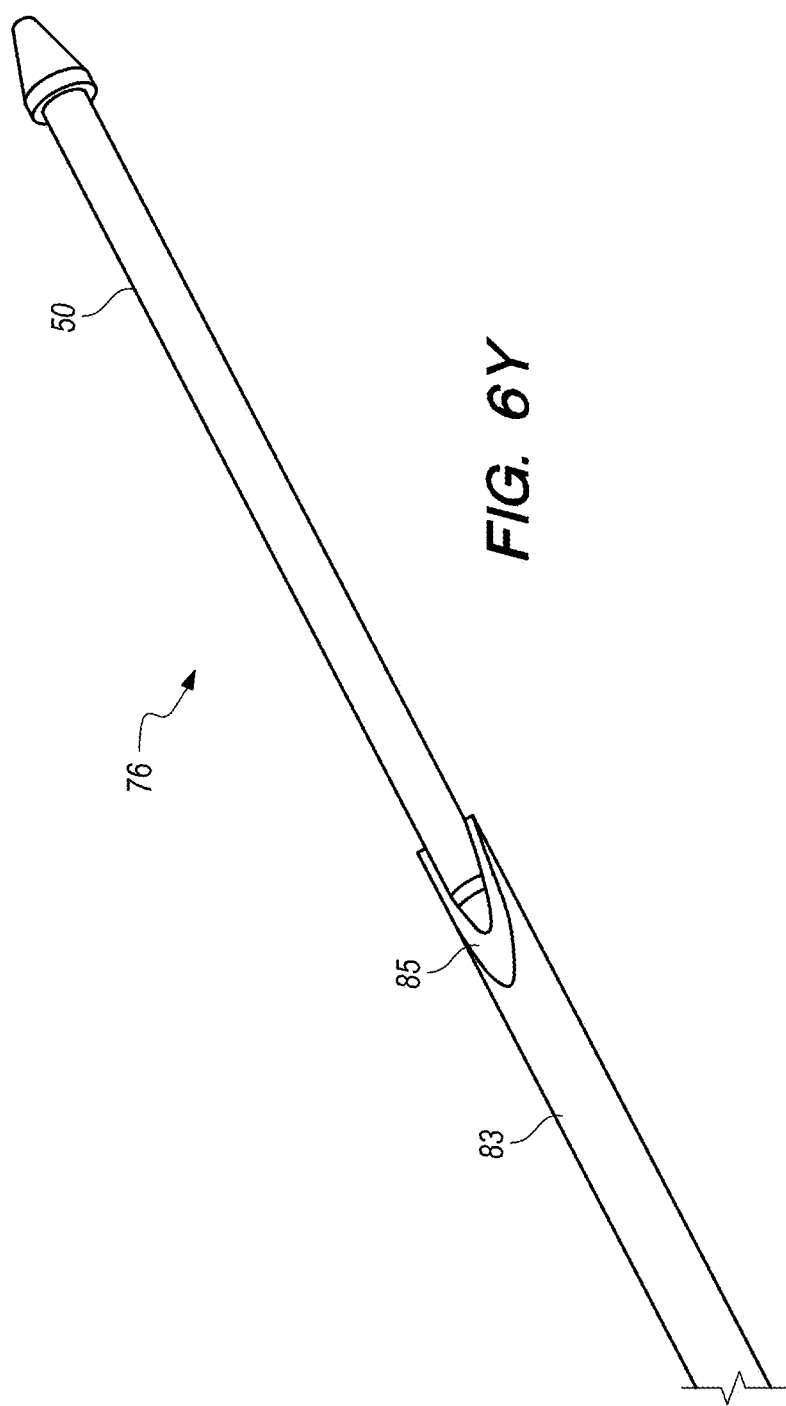

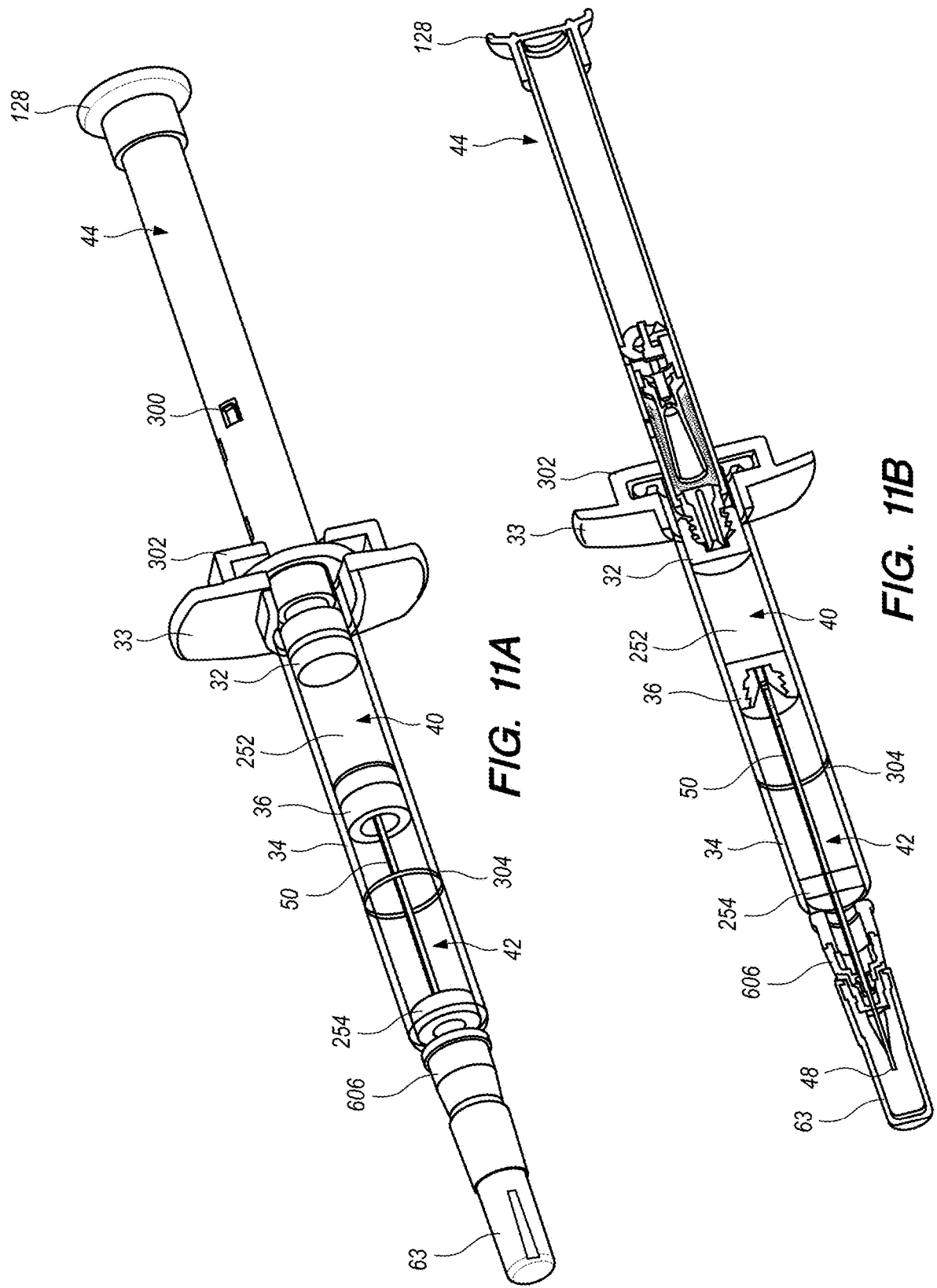

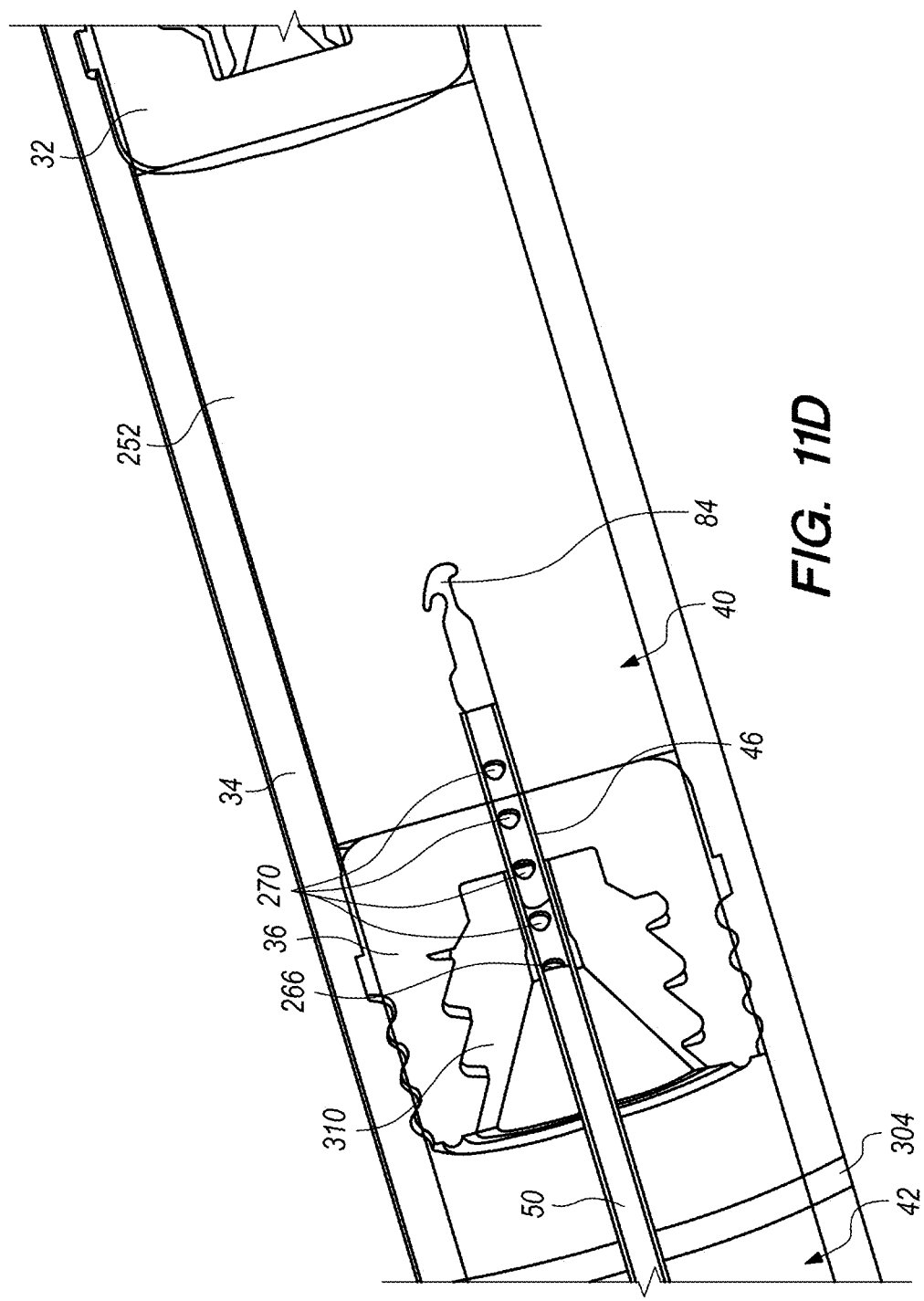

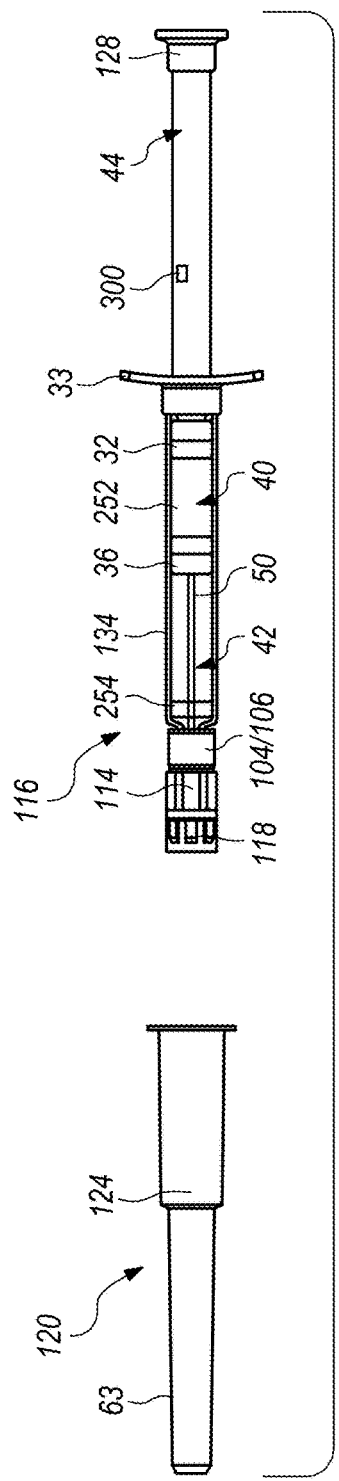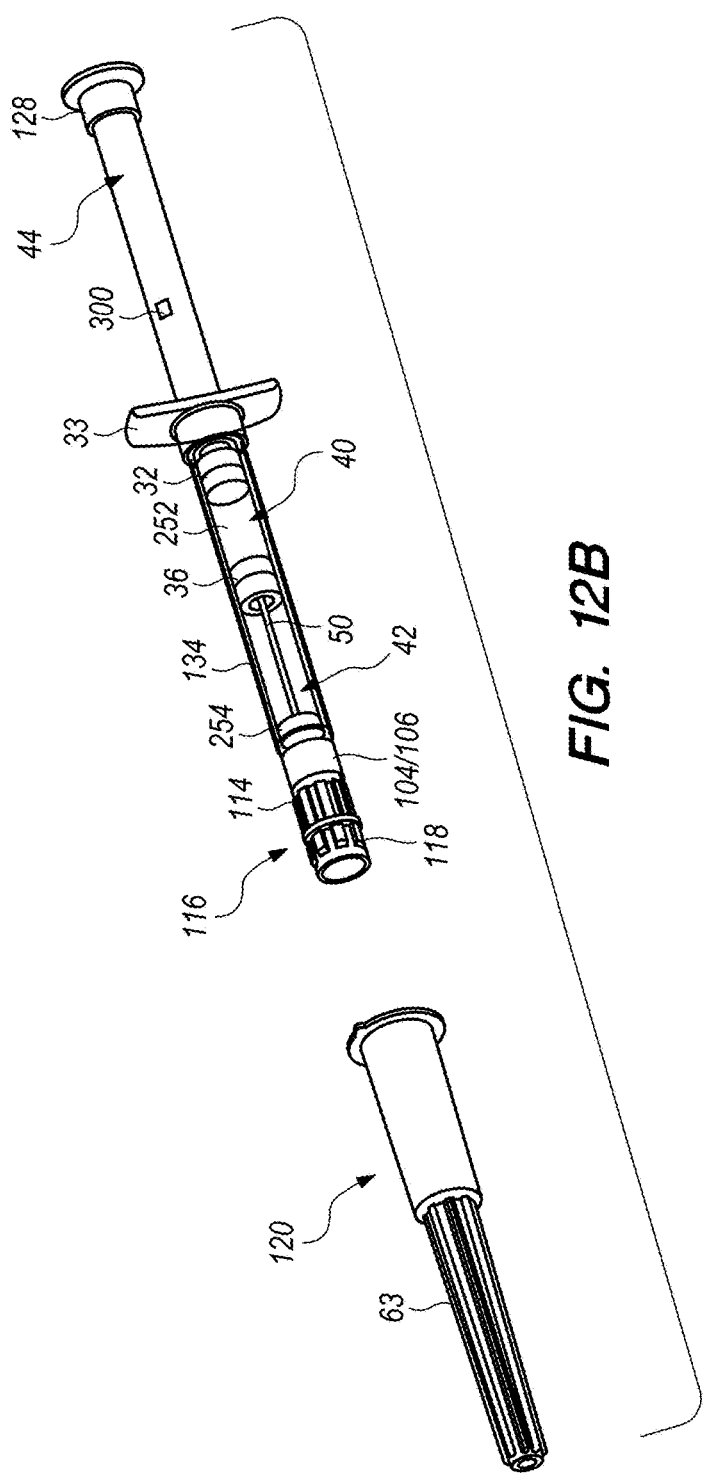
FIG. 12A
FIG. 12B

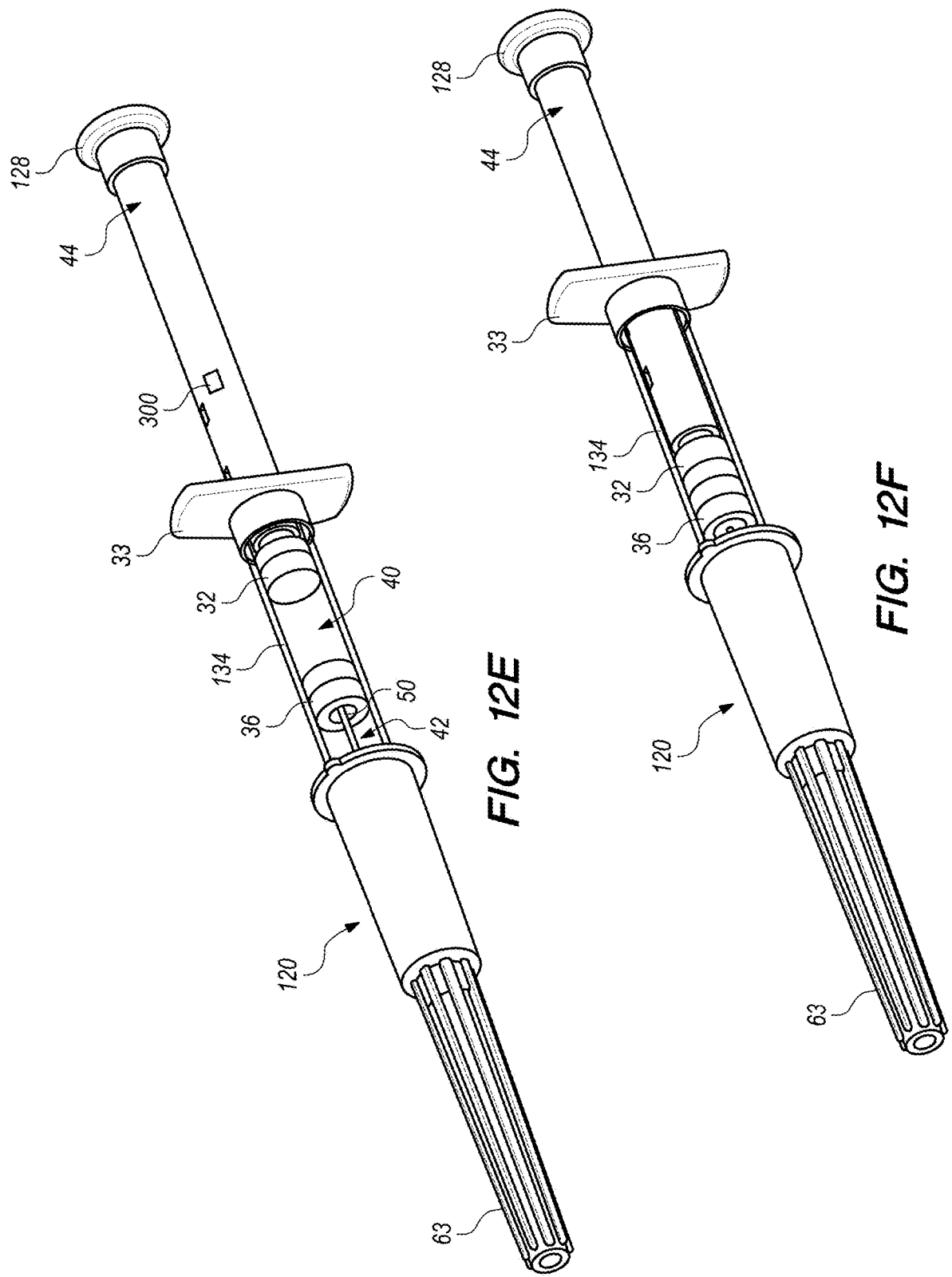

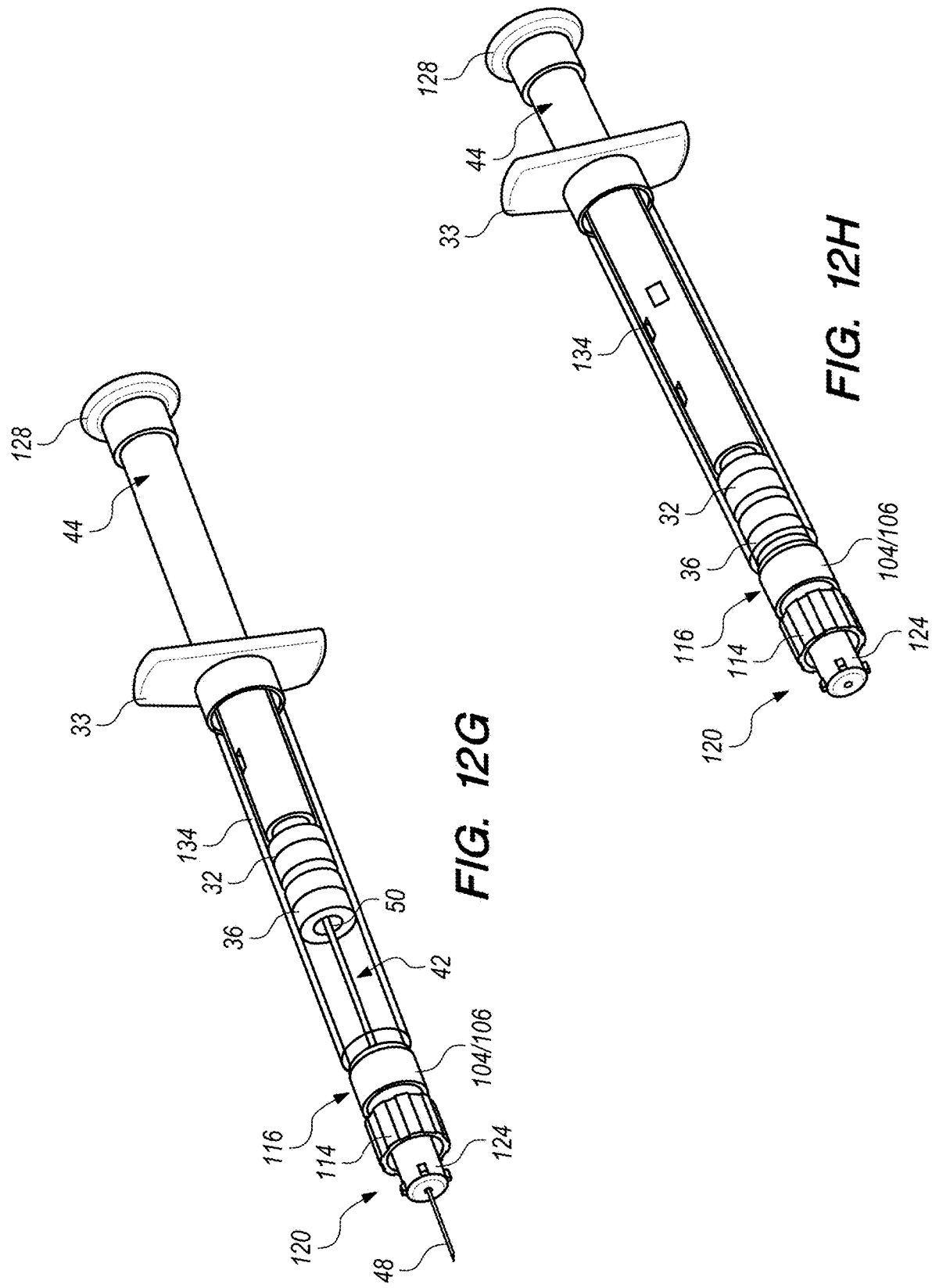

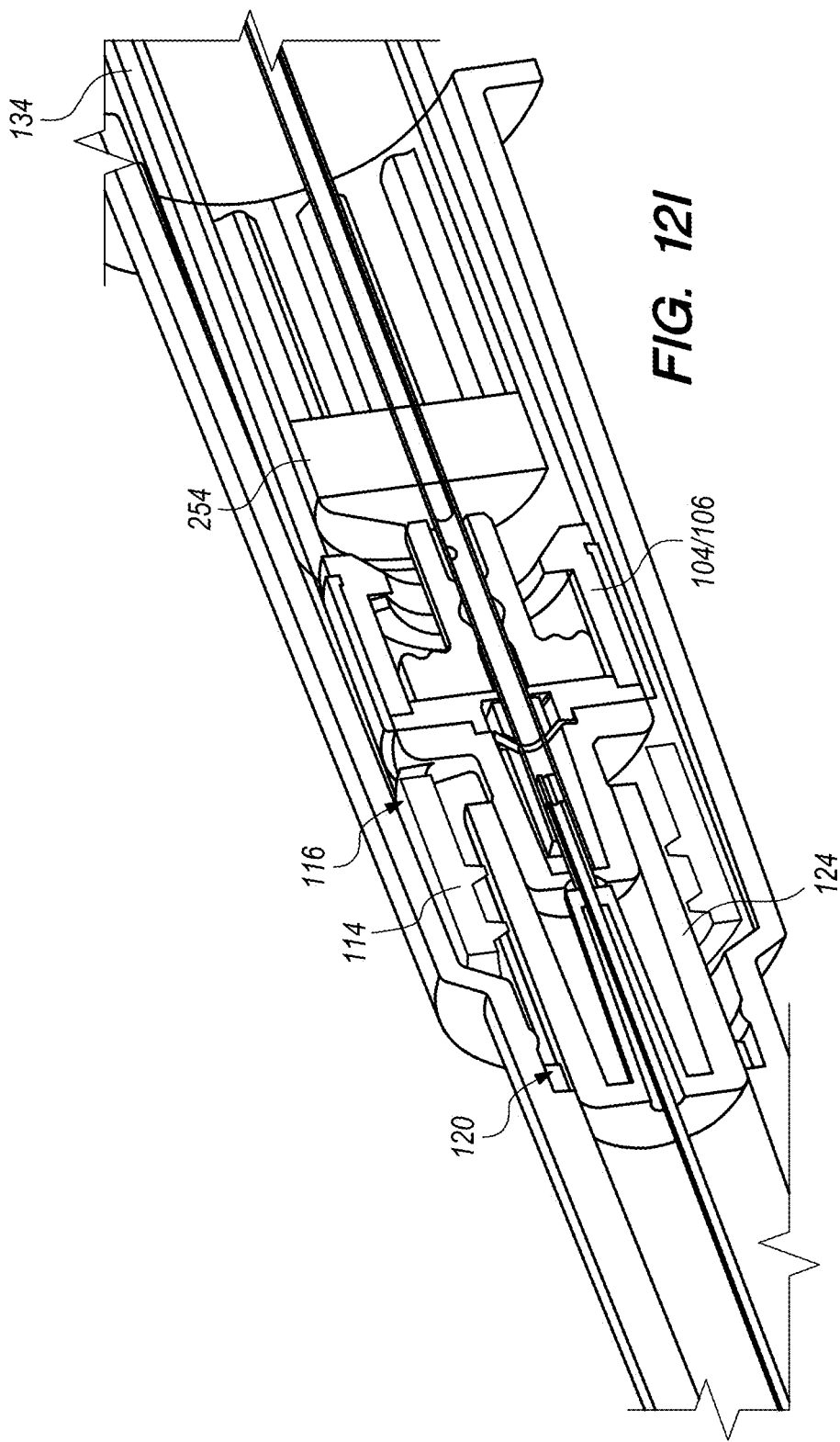

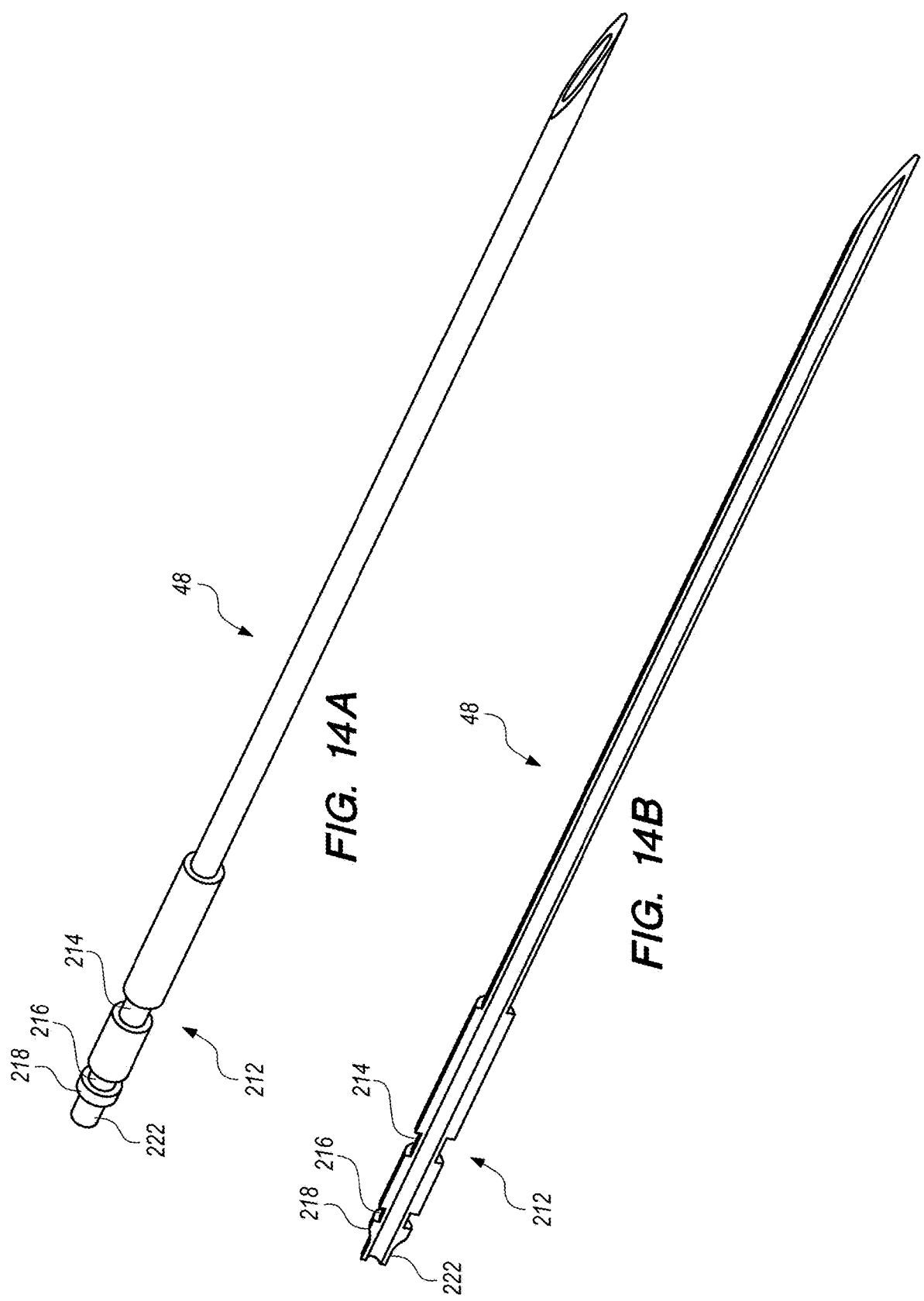

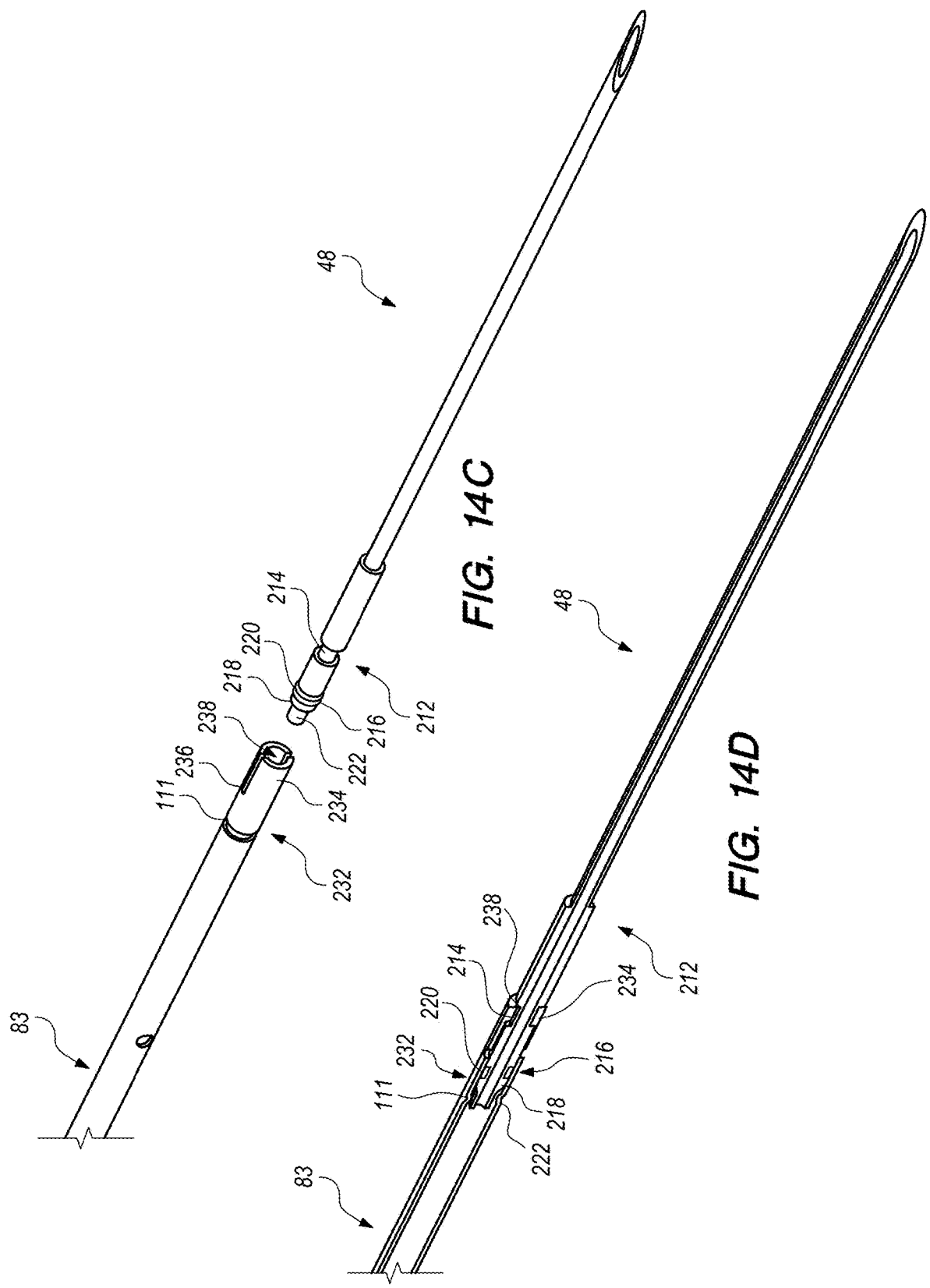

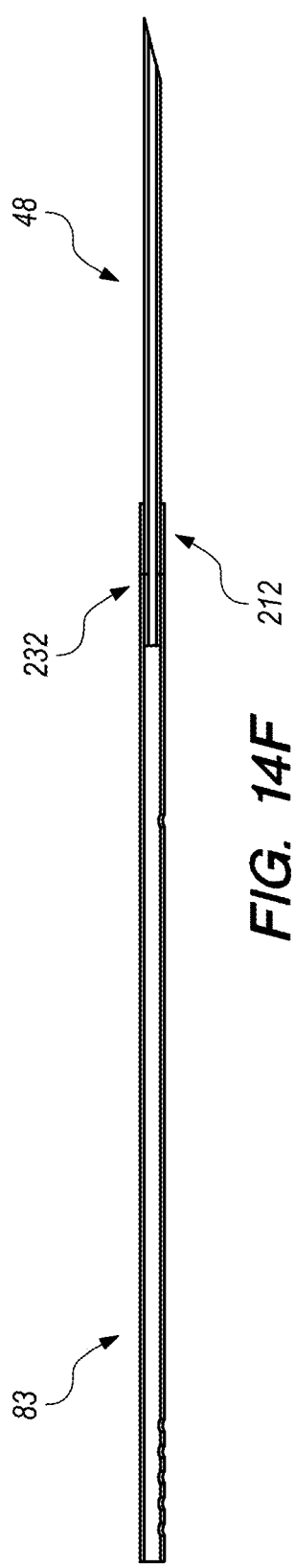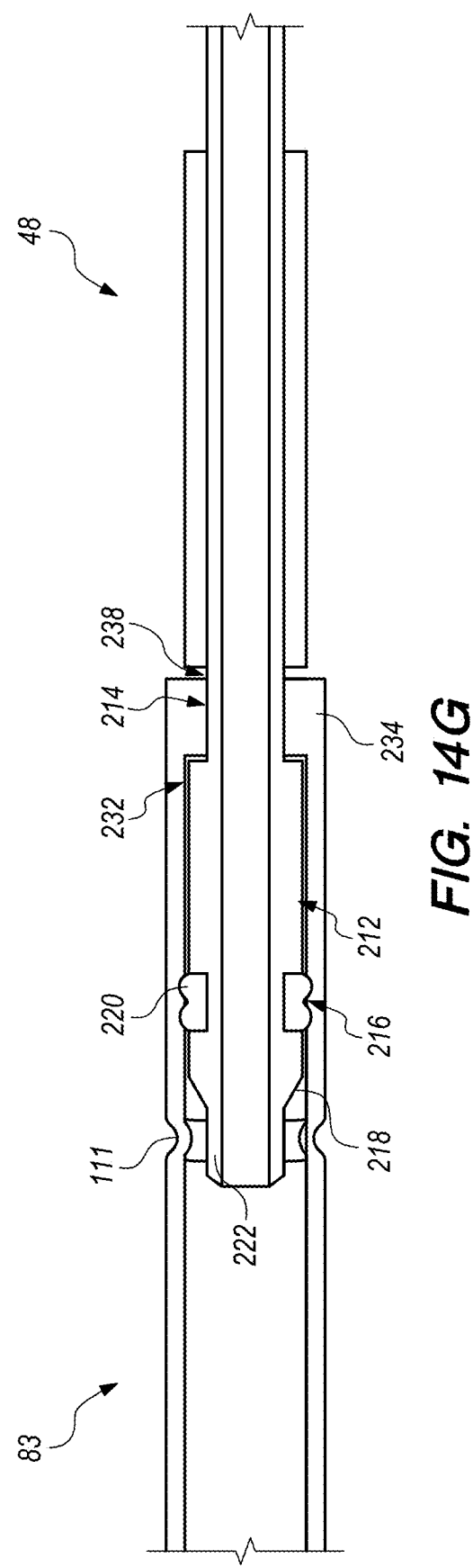

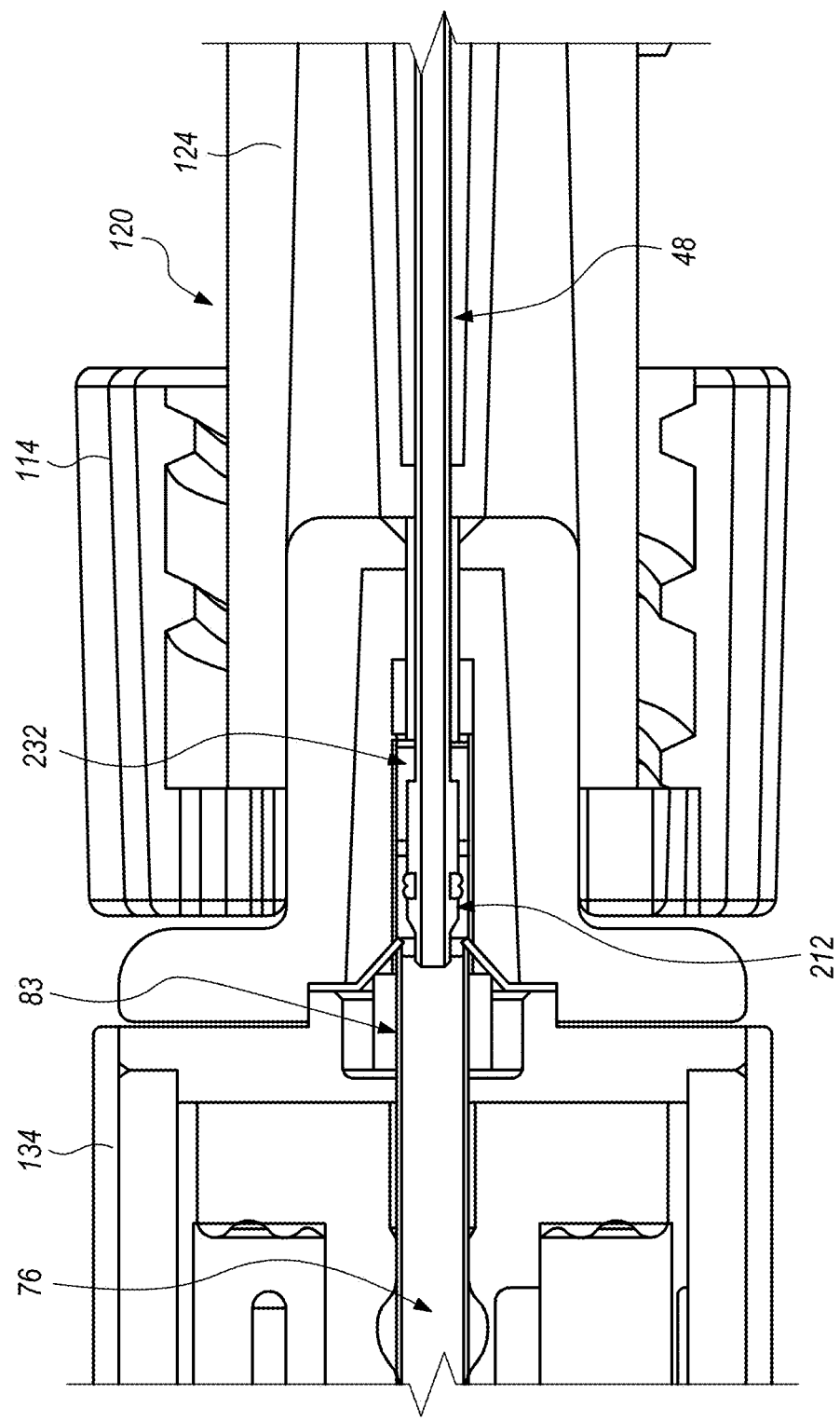

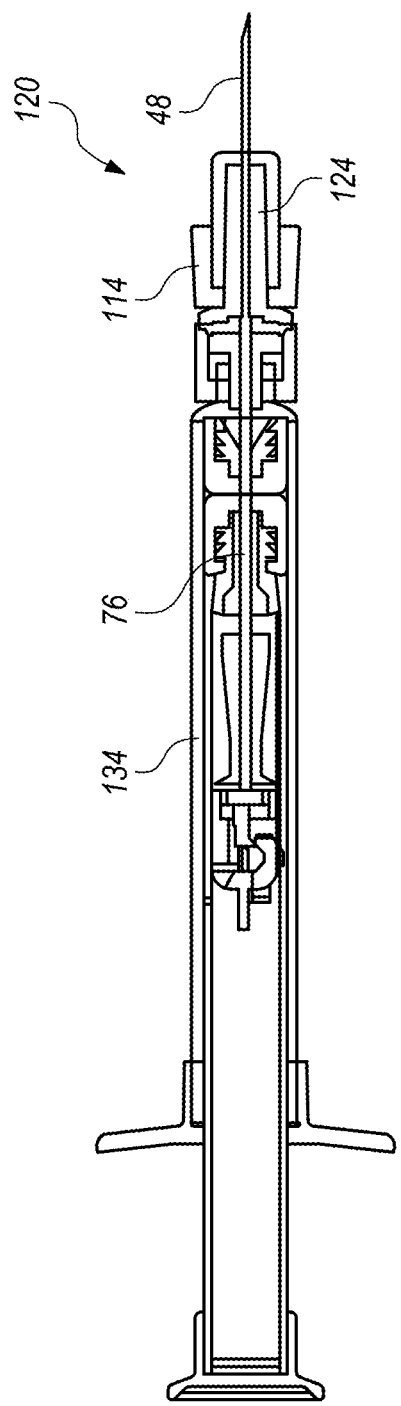

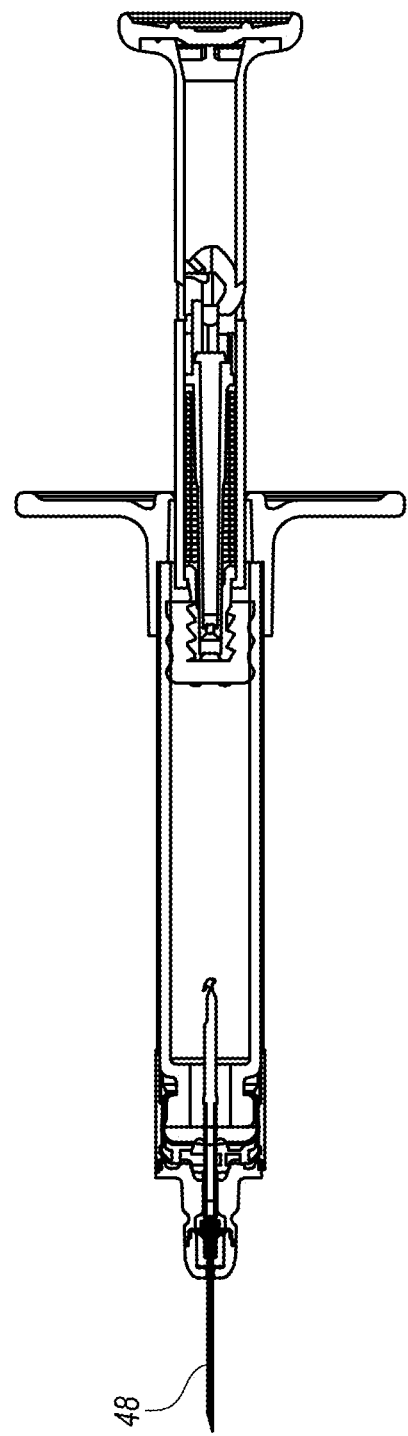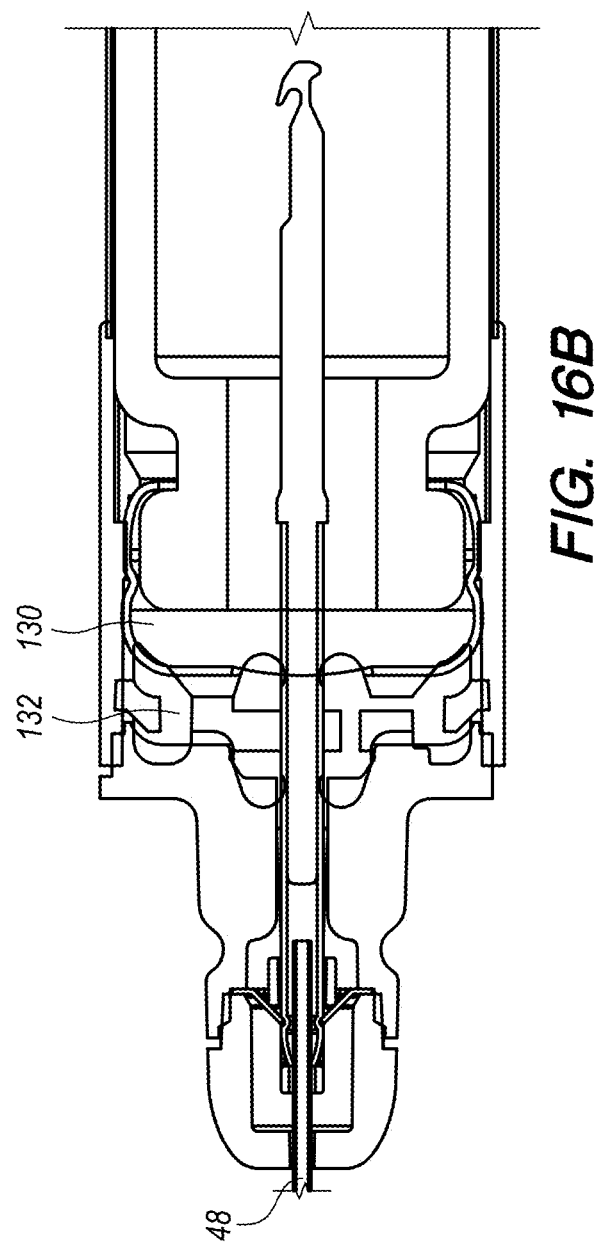

SYSTEM AND METHOD FOR SAFETY SYRINGE

CROSS-REFERENCE TO RELATED APPLICATION(S)

The present application claims priority to (1) U.S. Provisional Patent Application Ser. No. 62/416,102, filed on Nov. 1, 2016 and entitled "SYSTEM AND METHOD FOR SAFETY SYRINGE"; (2) U.S. Provisional Patent Application Ser. No. 62/431,382, filed on Dec. 7, 2016 and entitled "SYSTEM AND METHOD FOR SAFETY SYRINGE"; (3) U.S. Provisional Patent Application Ser. No. 62/480,276, filed Mar. 31, 2017 under attorney docket number CM.30015.00 and, entitled "SYSTEM AND METHOD FOR SAFETY SYRINGE"; (4) U.S. Provisional Patent Application Ser. No. 62/542,230, filed Aug. 7, 2017 and entitled "CARTRIDGE SAFETY INJECTION SYSTEM AND METHODS." This application includes subject matter similar to the subject matter described in the following co-owned U.S. patent applications: (1) U.S. Utility patent application Ser. No. 14/696,342, filed Apr. 24, 2015, entitled "SYSTEM AND METHOD FOR SAFETY SYRINGE"; (2) U.S. Utility patent application Ser. No. 14/543,787, filed Nov. 17, 2014, entitled "SYSTEM AND METHOD FOR DRUG DELIVERY WITH A SAFETY SYRINGE"; (3) U.S. Utility patent application Ser. No. 14/321,706, filed Jul. 1, 2014, entitled "SAFETY SYRINGE"; (4) U.S. Utility patent application Ser. No. 15/801,239, filed on Nov. 1, 2017 under Ser. No. 15/801,239 and entitled "SYSTEM AND METHOD FOR SAFETY SYRINGE"; (5) U.S. Utility patent application Ser. No. 15/801,259, filed on Nov. 1, 2017 under Ser. No. 15/801,259 and entitled "SYSTEM AND METHOD FOR SAFETY SYRINGE"; and (6) U.S. Utility patent application Ser. No. 15/801,281, filed on Nov. 1, 2017 under Ser. No. 15/801,281 and, entitled "CARTRIDGE SAFETY INJECTION SYSTEM AND METHODS." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "Luer slip," "slip-on" or "conical" Luer configuration). While such Luer couplings are perceived to be relatively safe for operators, there is risk of medicine spilling/leaking and parts breakage assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface (14). Liquid medicine may reside in the volume, or medicine reservoir, (40) between the distal seal (35) and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body (34) structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross sectional shape may establish a seal against the syringe body (34)), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Adding safety, auto-disabling, and anti-needle-stick features to existing syringe systems, using off-the-shelf components (e.g., syringe bodies, cartridges, and stoppers) requires a plurality of connections between the off-the-shelf components and the specialized components. These connections can be made during the assembly process by technicians or machines. Alternatively, some of these connections may be made directly before or during use by the medical professionals or self-administering patients. If any of these connections fail during injection, the safety syringe may not properly function, resulting in failed injections and danger to the medical professional administering the injections.

There is a need for injection systems which address the shortcomings of currently-available configurations. In particular, there is a need for safety injection solutions that may utilize the existing and relatively well-controlled supply chain of conventionally delivered pre-filled syringe assemblies such as those described in reference to FIGS. 3 to 5B. Further, there is a need for safety syringe assemblies including reliable connects between the various assembled parts that meet various injection system standards, such as safety, auto-disabling, and anti-needle-stick.

SUMMARY

Embodiments are directed to injection systems. In particular, the embodiments are directed to safe injection systems that move the needle into a protected configuration to minimize accidental user injury and contamination with used needles.

In one embodiment, a system for injecting includes a syringe body defining a proximal opening and a distal needle interface. The system also includes a plunger member defining a plunger interior and configured to be manually manipulated to insert a stopper member relative to the syringe body, the plunger member. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the syringe body. The needle assembly includes a needle having a needle proximal end feature, a hub, and a needle latching member configured to couple the needle to the hub. The needle is at least partially retractable into plunger interior upon manipulation of the plunger member relative to the syringe body to transform the energy-storage member latching member from a latched state to an unlatched state. The energy-storage member latching member is intercoupled between an interior surface of the plunger member and the needle retention feature. The needle proximal end feature includes an annular distally facing surface.

In one or more embodiments, the needle is configured to pierce through the stopper member to initiate needle retraction. The annular distally facing surface may be configured to prevent distal movement of the needle relative to the needle retention feature, when the needle is coupled to the needle retention feature. The needle proximal end feature may also include a proximally directed tapering surface. The proximally directed tapering surface may define a proximally pointed cone.

In one or more embodiments, the needle also has an elongate needle proximal portion, and the needle proximal end feature also includes a proximal tip. The elongate needle proximal portion may have a substantially constant first cross-sectional diameter. The annular distally facing surface may have a second cross-sectional diameter greater than the first cross-sectional diameter. The proximal tip may have a third cross-sectional diameter, lesser than the first cross-sectional diameter.

In one or more embodiments, the needle retention member includes a receiving member having a plurality of latching members to cooperate with the annular distally facing surface to prevent distal movement of the needle relative to the needle retention feature, when the needle is coupled to the needle retention feature. The plurality of latching members may consist of two latching members. Each of the two latching members may have an arcuate cross-sectional geometry. The plurality of latching members may consist of four latching members.

In one or more embodiments, the receiving member also has a rigid ring disposed at a distal end thereof. Each of the plurality of latching members may rotate about the rigid ring. The receiving member also having a plurality of slits, where each slit of the plurality of slits is disposed between two latching members of the plurality of latching members.

In one or more embodiments, the receiving member has an open configuration in which the needle proximal end feature can move proximally past the receiving member and a resting configuration in which the needle proximal end feature cannot move distally past the receiving member. The plurality of latching members may be closer to each other when the receiving member is in the resting configuration than when the receiving member is in the open configuration. The plurality of latching members may be biased to move closer to each other such that the receiving member is in the resting configuration. The plurality of latching members may be configured to move away from each other when the needle proximal end feature is moved proximally past the receiving member to place the receiving member in the open configuration. The plurality of latching members may be biased to move closer to each other when the needle proximal end feature has moved past the receiving member in a proximal direction such that the receiving member is returned to the resting configuration, such that an interaction between the plurality of latching members and the annular distally facing surface of the needle proximal end feature prevents distal movement of the needle relative to the needle retention feature.

In another embodiment, a needle assembly includes a proximal portion. The needle assembly also includes a tubular middle portion having a distal end receiving member having a plurality of latching members. The needle assembly also includes a distal portion having a proximal end connector including a reduced diameter area to receive the plurality of latching members thereby coupling the distal portion to the tubular middle portion.

In one or more embodiments, the reduced diameter area is an annular space. The distal end receiving member may also have a plurality of slits, where each slit of the plurality of slits is disposed between two latching members of the plurality of latching members. The proximal end connector may also include an O-ring to form a fluid tight seal between an outer surface of the proximal end connector and an inner surface of the tubular middle portion when the distal portion is coupled to the tubular middle portion.

In one or more embodiments, the proximal end connector also includes a proximally directed tapering surface. The proximally directed tapering surface may define a portion of a proximally pointed cone. The distal end receiving member may also have a proximally directed tapering surface to facilitate insertion of a proximal end of the proximal end connector into a lumen of the tubular middle portion. The proximally directed tapering surface may define a funnel that tapers in a proximal direction.

In one or more embodiments, the tubular middle portion may have a middle portion lumen and a proximal opening to allow fluid communication between an exterior of the tubular middle portion and the middle portion lumen. The distal portion may have a distal portion lumen and a distal opening to allow fluid communication between an exterior of the distal portion and the distal portion lumen. The proximal opening of the tubular middle portion, the middle portion lumen, the distal portion lumen, and the distal opening of the distal portion may form a fluid path between the exterior of the tubular middle portion and the exterior of the distal portion when the distal portion is coupled to the tubular middle portion. The tubular middle portion may also have a notch to cooperate with a needle latching member to restrict movement of the needle.

In one or more embodiments, the distal end receiving member has an open configuration in which a portion of the proximal end connector can move proximally past the distal end receiving member and a resting configuration in which the portion of the proximal end connector cannot move distally past the distal end receiving member. The plurality of latching members may be closer to each other when the distal end receiving member is in the resting configuration than when the distal end receiving member is in the open configuration. The plurality of latching members may be biased to move closer to each other such that the distal end receiving member is in the resting configuration. The plurality of latching members may be configured to move away from each other when the portion of the proximal end connector is moved proximally past the distal end receiving member to place the distal end receiving member in the open configuration. The plurality of latching members may be biased to move closer to each other when the portion of the proximal end connector has moved into the tubular middle portion such that the distal end receiving member is returned to the resting configuration, the plurality of latching members are disposed at least partially in the reduce diameter area, and an interaction between the plurality of latching members and the reduced diameter area of the proximal end connector prevents axial movement of the needle relative to the needle retention feature.

In still another embodiment, a system for injecting includes a syringe body defining a proximal opening and a distal needle interface. The system also includes a plunger member defining a plunger interior and configured to be manually manipulated to insert a stopper member relative to the syringe body. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the syringe body. The needle assembly includes a needle, a proximal connector hub coupled to the tubular middle portion of the needle, and a distal connector hub coupled to the distal portion of the needle. The needle includes a proximal portion, a tubular middle portion, having a distal end receiving member having a plurality of latching members, and a distal portion, having a proximal end connector. The proximal end connector includes a reduced diameter area to receive the plurality of latching members thereby coupling the distal portion to the tubular middle portion. The distal connector hub is configured to couple to the proximal connector hub to couple the distal and tubular middle portions of the needle. The needle is at least partially retractable into plunger interior upon manipulation of the plunger member relative to the syringe body to transform the energy-storage member latching member from a latched state to an unlatched state. The energy-storage member latching member is intercoupled between an interior surface of the plunger member and the needle retention feature.

In one or more embodiments, the proximal and distal connectors are Luer connectors. The reduced diameter area may be an annular space. The distal end receiving member may also have a plurality of slits, where each slit of the plurality of slits is disposed between two latching members of the plurality of latching members. The proximal end connector may also include an O-ring to form a fluid tight seal between an outer surface of the proximal end connector and an inner surface of the tubular middle portion when the distal portion is coupled to the tubular middle portion.

In one or more embodiments, the proximal end connector also includes a proximally directed tapering surface. The proximally directed tapering surface may define a portion of a proximally pointed cone. The distal end receiving member may also have a proximally directed tapering surface to facilitate insertion of a proximal end of the proximal end connector into a lumen of the tubular middle portion. The proximally directed tapering surface defines a funnel that tapers in a proximal direction.

In one or more embodiments, the tubular middle portion has a middle portion lumen and a proximal opening to allow fluid communication between an interior of the syringe body and the middle portion lumen. The distal portion may have a distal portion lumen and a distal opening to allow fluid communication between an exterior of the distal portion and the distal portion lumen. The proximal opening of the tubular middle portion, the middle portion lumen, the distal portion lumen, and the distal opening of the distal portion may form a fluid path between the interior of the syringe body and the exterior of the distal portion when the distal portion is coupled to the tubular middle portion.

In one or more embodiments, the needle hub assembly also includes a needle latching member configured to couple the needle to the hub. The tubular middle portion may also have a notch to cooperate with the needle latching member to couple the needle to the hub. The needle latching member may include a locking latching member releasable by distal movement of the needle relative to the hub to uncouple the needle from the hub.

In one or more embodiments, the distal end receiving member has an open configuration in which a portion of the proximal end connector can move proximally past the distal end receiving member and a resting configuration in which the portion of the proximal end connector cannot move distally past the distal end receiving member. The plurality of latching members may be closer to each other when the distal end receiving member is in the resting configuration than when the distal end receiving member is in the open configuration. The plurality of latching members may be biased to move closer to each other such that the distal end receiving member is in the resting configuration. The plurality of latching members may be configured to move away from each other when the portion of the proximal end connector is moved proximally past the distal end receiving member to place the distal end receiving member in the open configuration. The plurality of latching members may be biased to move closer to each other when the portion of the proximal end connector has moved into the tubular middle portion such that the distal end receiving member is returned to the resting configuration, the plurality of latching members are disposed at least partially in the reduce diameter area, and an interaction between the plurality of latching members and the reduced diameter area of the proximal end connector prevents axial movement of the needle relative to the needle retention feature.

In yet another embodiment, a method of retracting a needle after injection, the method includes injecting a substance using a system having a syringe body, a plunger member, and a needle. The plunger member has a needle retention feature therein. The needle has a proximal end feature including an annular distally facing surface. The method also includes moving the proximal end feature of the needle into an interior of the needle retention feature to thereby couple the needle to the needle retention feature. The method further includes retracting the needle retention feature in a proximal direction inside of the plunger member, thereby retracting the needle at least partially within the plunger member.

In one or more embodiments, the needle retention feature includes a receiving member having a plurality of latching members, the proximal end feature defines a proximally pointed cone, and moving the proximal end feature of the needle into the interior of the needle retention feature includes inserting a proximal end of the proximally pointed cone through an opening defined by the plurality of latching members of the receiving member. Inserting the proximal end of the proximally pointed cone through the opening may move the plurality of latching members away from each other to place the receiving member in an open configuration. Moving the proximal end feature of the needle into the interior of the needle retention feature may also include inserting the proximally pointed cone completely through the opening to allow the plurality of latching members to move toward each other to return the receiving member to a resting configuration, such that an interaction between the plurality of latching members and the annular distally facing surface of the proximal end feature prevents distal movement of the needle relative to the needle retention feature.

In still another embodiment, a method of assembling a needle having a proximal portion coupled to a tubular middle portion having a distal end receiving member having a plurality of latching members, and a distal portion having a proximal end connector including a reduced diameter area, includes moving a portion of the proximal end connector into an interior of the distal end receiving member to thereby couple the distal portion to the tubular middle portion.

In one or more embodiments, moving the portion of the proximal end connector into the interior of the distal end receiving member includes inserting a proximal end of the proximal end connector through an opening defined by the plurality of latching members of the distal end receiving member. Inserting the proximal end of the proximal end connector through the opening may move the plurality of latching members away from each other to place the distal end receiving member in an open configuration. Moving the portion of the proximal end connector into the interior of the distal end receiving member may also include inserting the portion of the proximal end connector completely through the opening to allow the plurality of latching members to move toward each other and into the reduced diameter area of the proximal end connector to return the distal end receiving member to a resting configuration, and an interaction between the plurality of latching members and the reduced diameter area of the proximal end connector prevents axial movement of the needle relative to the needle retention feature.

In yet another embodiment, a system for injecting includes a syringe body defining a proximal opening and a distal needle interface at a distal end thereof. The system also includes proximal and distal stopper members disposed in the syringe body, forming a proximal drug chamber between the proximal and distal stopper members and a distal drug chamber between the distal stopper member and the distal end of the syringe body. The system further includes a plunger member defining a plunger interior and configured to be manually manipulated to insert the proximal stopper member relative to the syringe body. The plunger member includes a needle retention feature disposed in the plunger interior, an energy-storage member disposed in the plunger interior, and an energy-storage member latching member disposed in the plunger interior. Moreover, the system includes a needle hub assembly coupled to the distal needle interface of the syringe body. The needle assembly includes a needle having a needle proximal end feature, a hub, and a needle latching member configured to couple the needle to the hub. The needle is at least partially retractable into plunger interior upon manipulation of the plunger member relative to the syringe body to transform the energy-storage member latching member from a latched state to an unlatched state. The energy-storage member latching member is intercoupled between an interior surface of the plunger member and the needle retention feature. The needle proximal end feature includes an annular distally facing surface. The needle proximal end feature includes a proximal opening and a hollow interior.

In one or more embodiments, the needle includes a tubular member coupled to the proximal end feature such that an interior of the tubular member is in fluid communication with the hollow interior of the needle proximal end feature. The tubular member may include a side opening. A fluid path may be formed between the proximal opening and the side opening through the hollow interior of the needle proximal end feature and the interior of the tubular member. The needle proximal end feature and the tubular member may be configured such that the tubular member and the needle proximal end feature can span the distal stopper member with the proximal opening in the proximal chamber and the side opening in the distal chamber.

In one or more embodiments, the needle including a shoulder configured to increase a distal force required to push the distal stopper member over the needle. The proximal opening may be defined by blunted edges of the needle proximal end feature. The needle proximal end feature may include a closed proximal end The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 16A-16B illustrate safe cartridge injection systems with which distal needle tip connectors according to various embodiments may be used.

Figure 1A:
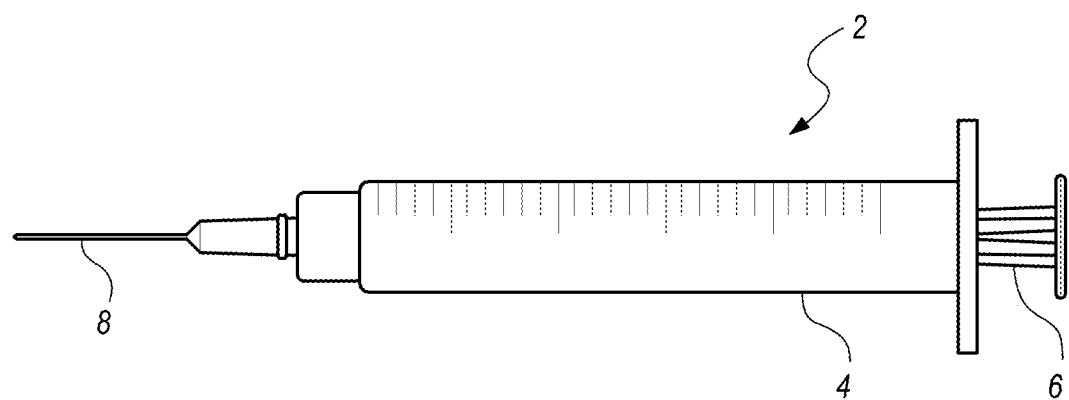
FIGS. 1A-5C illustrate various aspects of conventional injection syringe configurations.
Figure 1B:
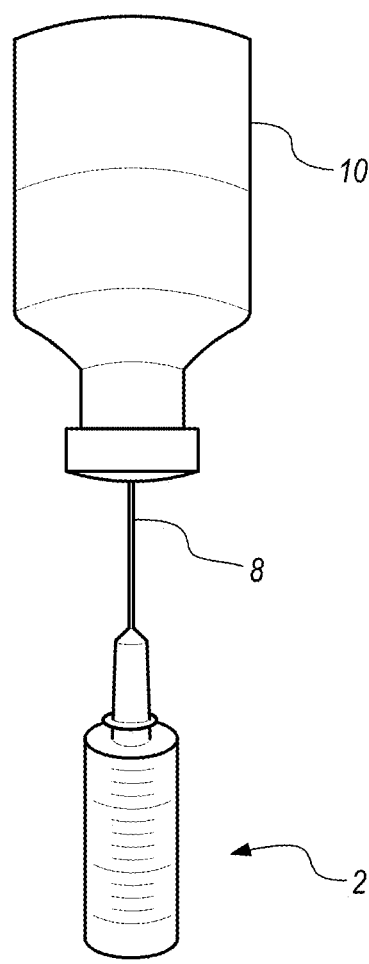
Figure 2A:
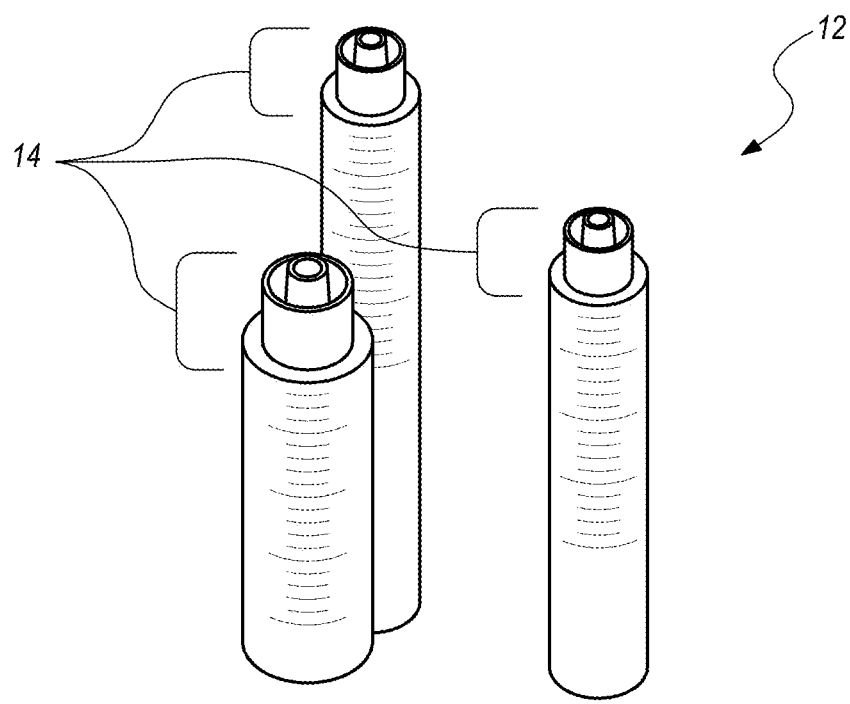
Figure 2B:
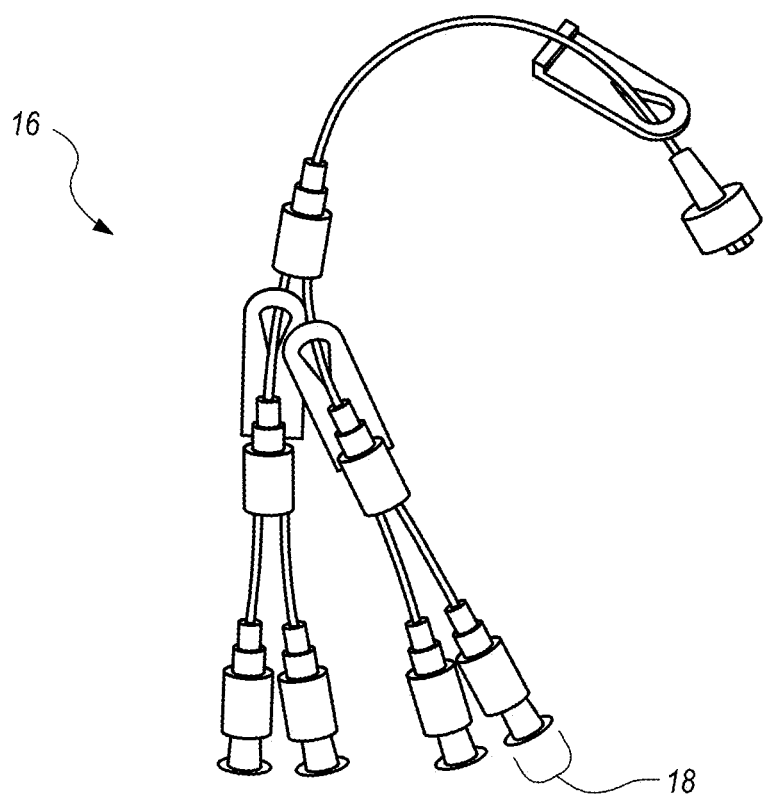
Figure 3:
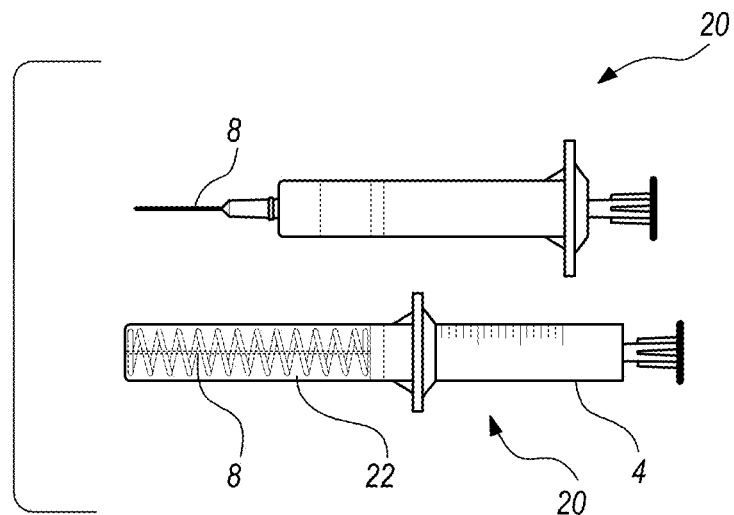
Figure 4A:
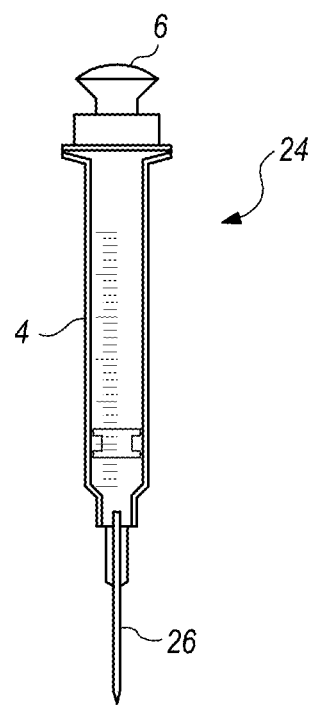
Figure 4B:
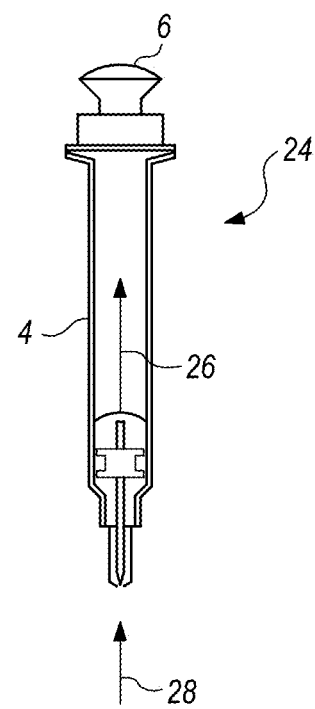
Figure 5A:
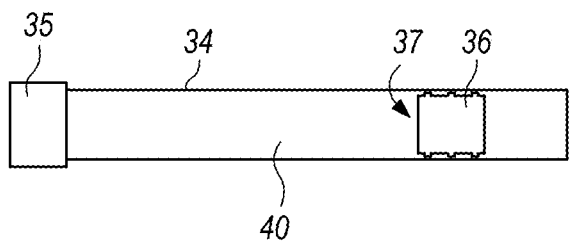
Figure 5B:
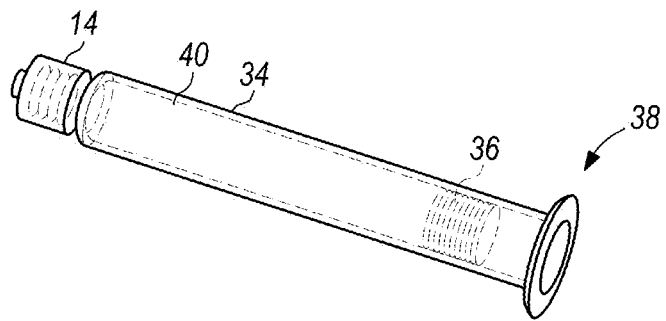
Figure 5C:
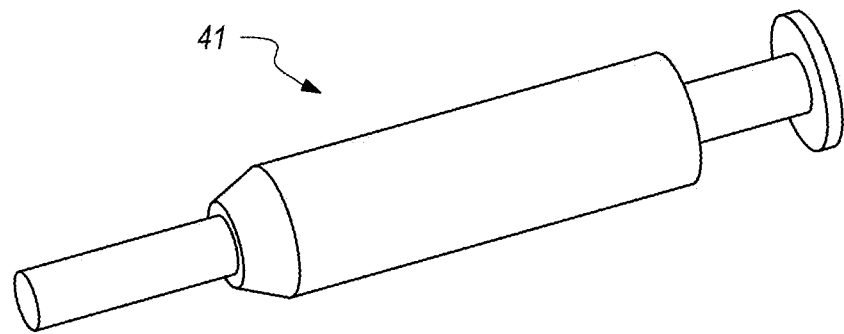

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Safe Syringe System (with Staked Needle)

Figure 6C:
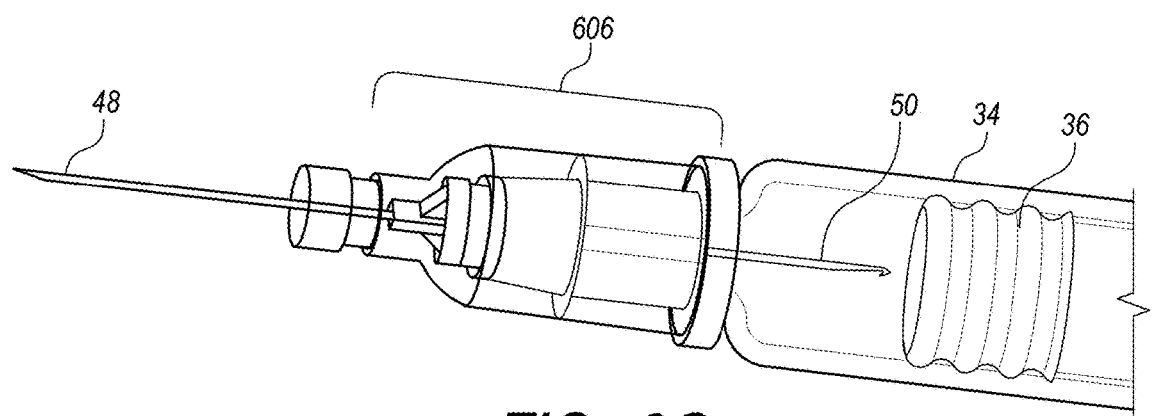
FIGS. 6A-6CC illustrate a safe injection system according to one embodiment.
Figure 6D:
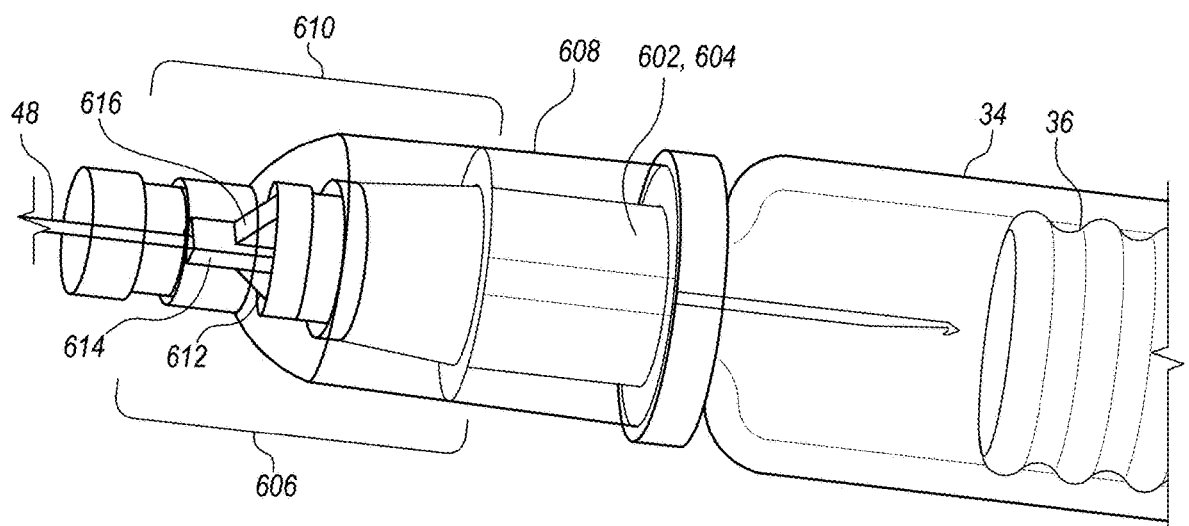
Figure 6G:
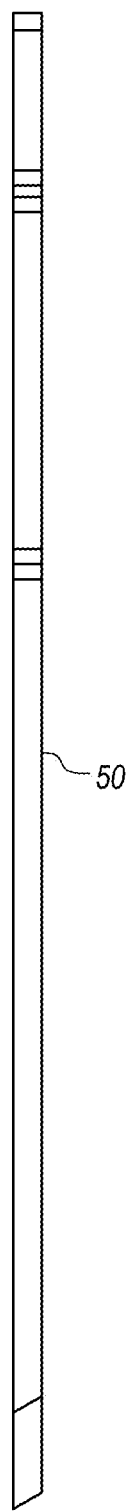
Figure 6H:
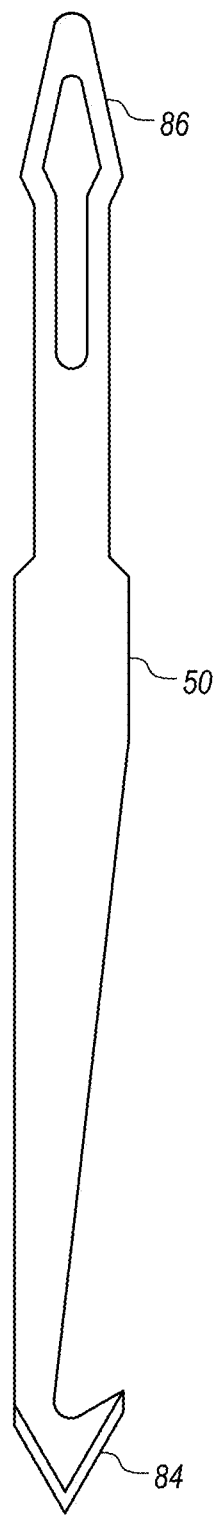
Figure 6I:
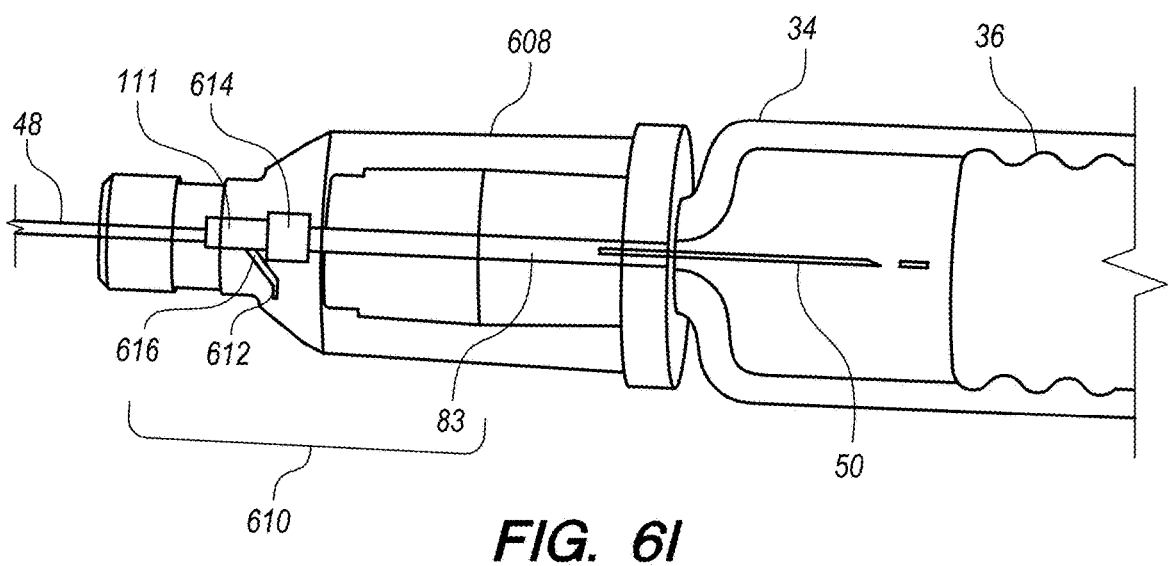
Figure 6J:
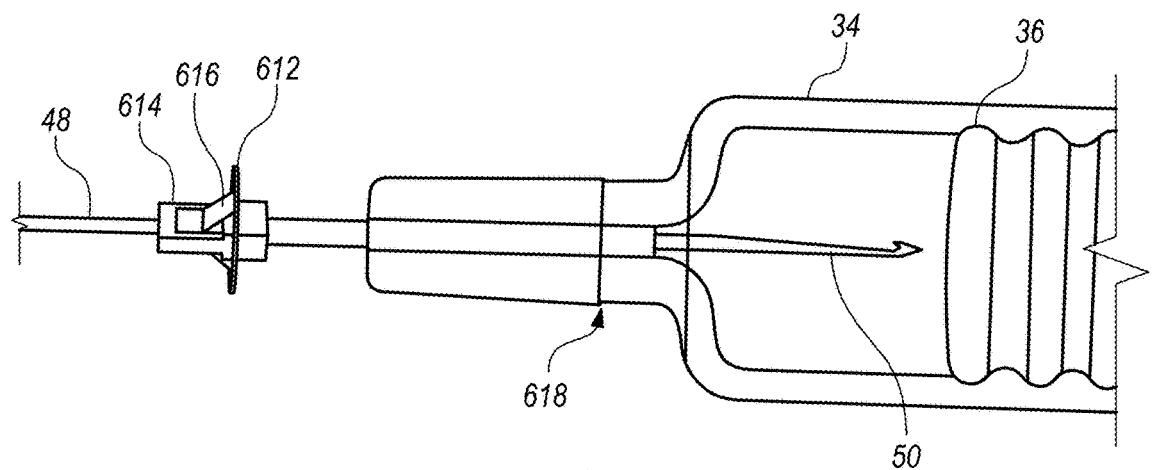
Figure 6K:
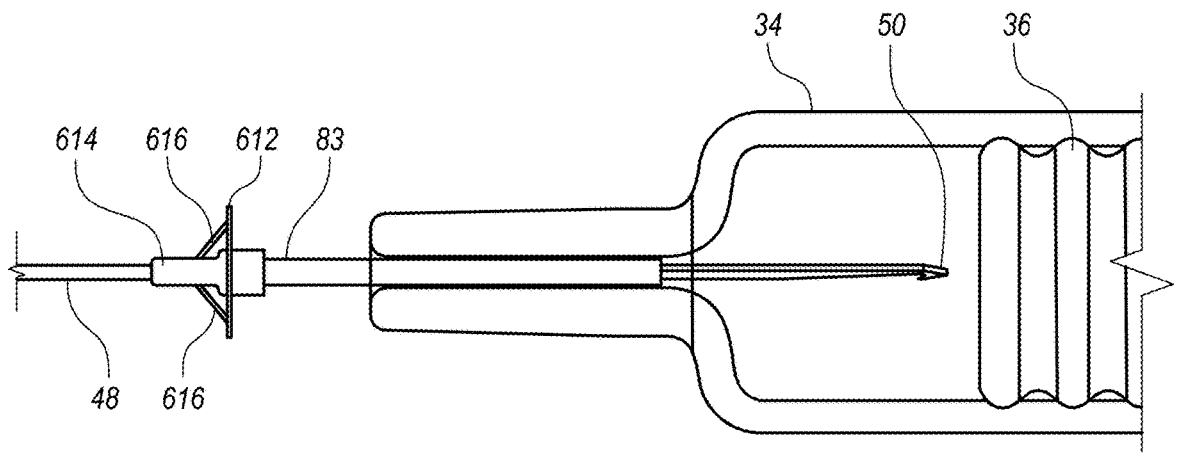
Figure 6L:
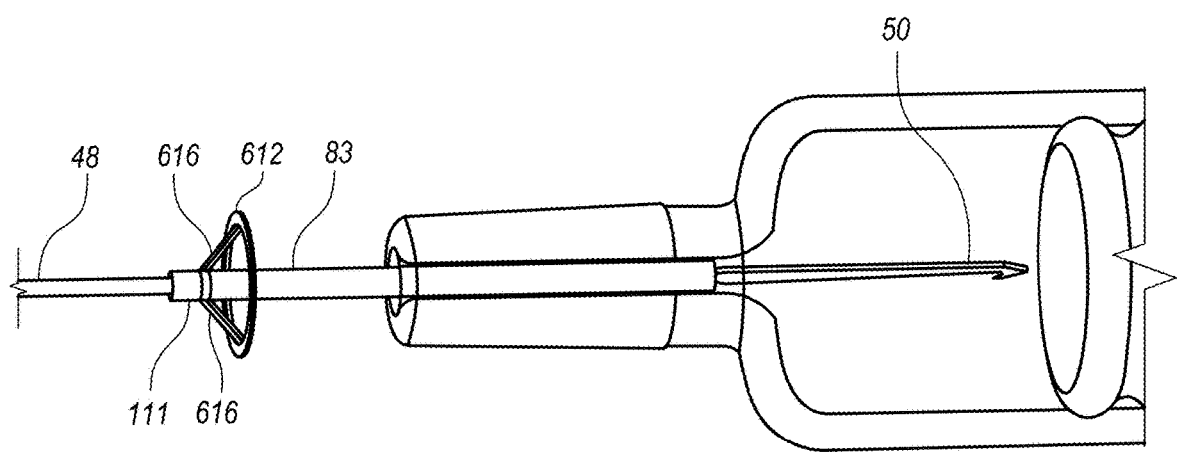
Figure 6W:
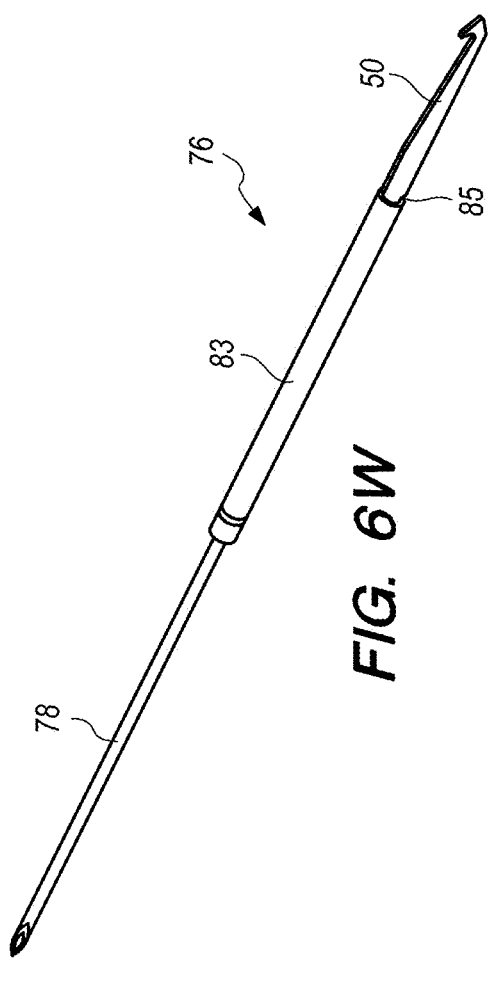
Figure 6X:
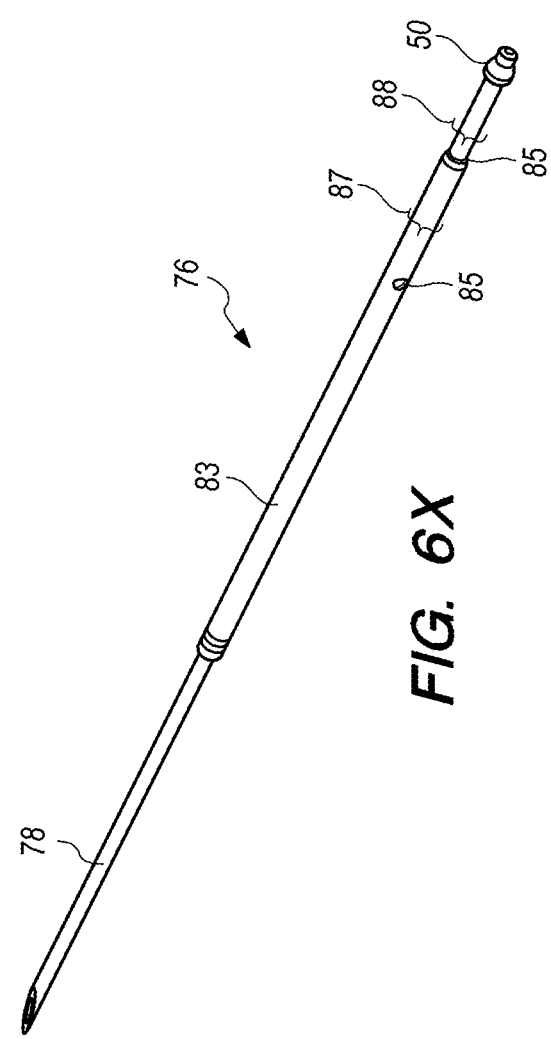
Figure 6Z:
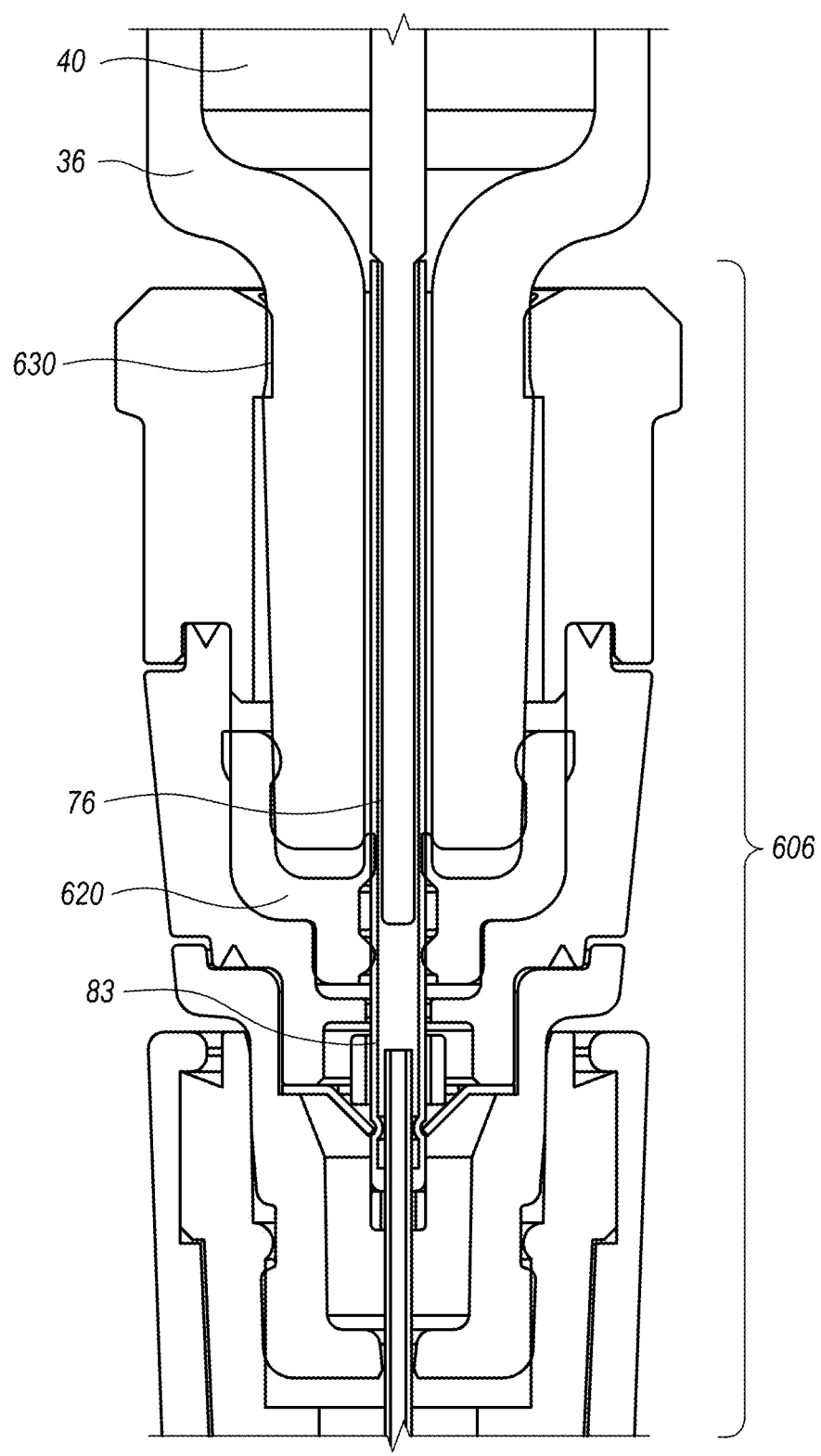
Figure 6A:
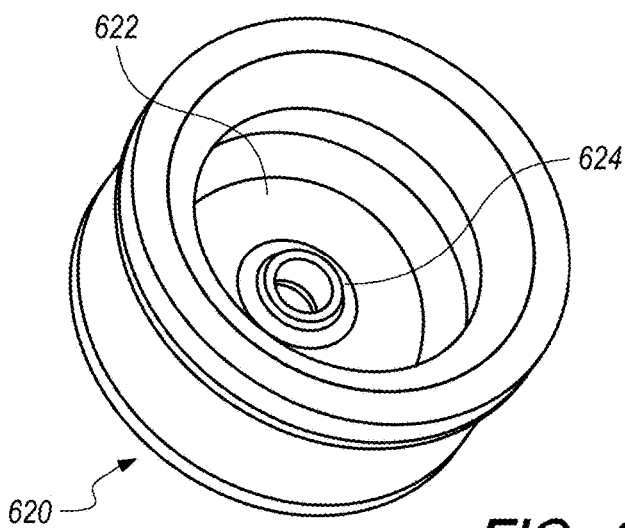
Figure 6B:
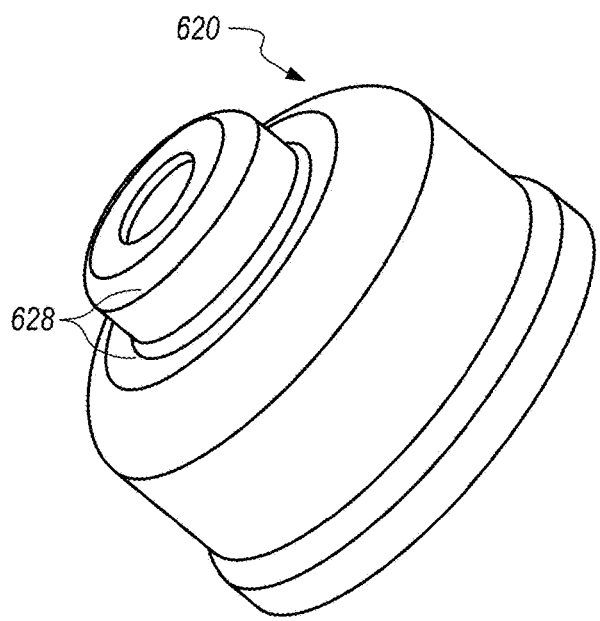
Figure 6C:
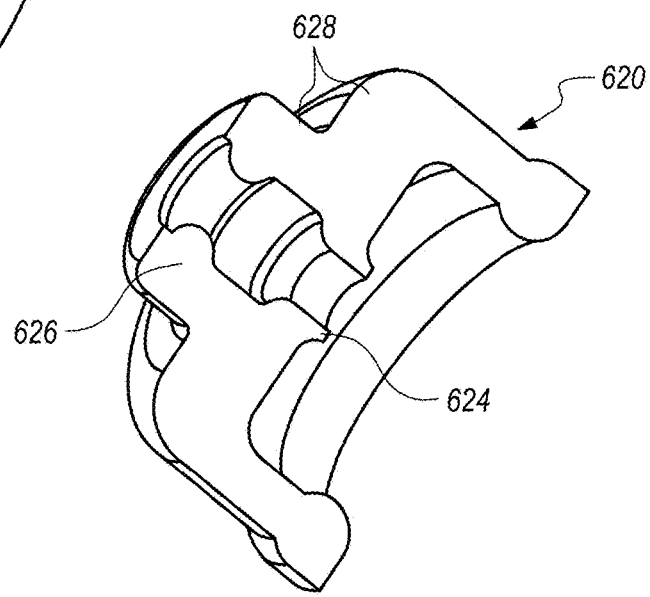

Referring to FIGS. 6A-6B, a side and a perspective view of a safe injection system are shown, with a conventional off-the-shelf pre-filled syringe body (34) defining a medicine chamber (40), a stopper member (36) occluding the proximal aspect of the medicine chamber (40), and a needle coupling assembly (606) disposed at the distal aspect of the medicine chamber (40) with a needle cover member (63) installed for storage. The safe injection system controls exit of medicine from the chamber (40) distally subject to insertion of a plunger assembly relative to the syringe body (34) by a user. The plunger assembly includes a stopper member (36), a plunger housing member (69) and a plunger manipulation interface (128).

Referring to FIG. 6C-6D the safe injection system has a staked needle configuration wherein upon presentation to the user, a needle assembly, comprising a needle coupling assembly (606; itself comprising a proximal housing portion 608 and a distal housing portion 610), a needle distal tip (48), a needle joining member (83—see, for example, FIG. 6E), and a needle proximal end (50) are mounted in position ready for injection after removal of a needle cover member (63) which may comprise an elastomeric sealing material on its internal surface to interface with the needle distal tip (48) or the distal housing portion (610) during storage. While, the staked needle is depicted as mounted in position, the staked needle may be removably coupled to the syringe body (34) using a Luer interface (not shown), with the proximal end (50) of the needle member extending through the Luer interface and into the medicine chamber (40). In the embodiments depicted in FIGS. 6A-8K, a significant portion of the safe needle retraction hardware resides within a plunger housing.

Referring to FIGS. 6E and 6F, the needle spine assembly (76), i.e., "needle," includes an injection member having a distal needle tip (48), and a needle proximal end (50) coupled to a needle joining member (83). The needle joining member (83) is configured to have a necked-down or radially-reduced portion (111) that is configured to interface with a latching member (612) and movable block member (614) such that during injection, the needle distal tip (48), needle joining member (83), and needle proximal end (50) remain fixed in position relative to the syringe body (34), but after complete insertion of the plunger assembly relative to a small diameter flange (33—see, for example, FIG. 6A) (i.e., after full expulsion of the medicine which may be contained within the medicine chamber 40 of the syringe body 34), the movable block member (614) is advanced relative to the distal housing portion (610) such that the plurality (two are illustrated) of cantilevered latch members (616) of the latch member (612) are urged out of the way by the movable block member (614) to allow the needle distal end (48), joining member (83), and proximal end (50) to be retracted through their coupling (as described below), thereby placing the needle distal end (48) safely within the plunger housing member (69). In other words, the cantilevered latch members (616) retain the position of the needle distal end (48) during injection, until they are pushed out of the way by the movable block member (614) at full plunger insertion, after which the needle is free to be withdrawn as described below.

Referring to FIG. 6D, at initial assembly time (i.e., in the factory or processing facility—not in the field in a "staked needle" configuration), the proximal housing assembly (608) is configured to snap-fit (i.e., using a snap ring element 604 comprising or coupled to the proximal housing assembly) over a slightly recessed radial portion (602) of the syringe body which is formed into the syringe body upon manufacture of the syringe body. FIG. 6Z illustrates a cross sectional view of such constructs in action, and FIGS. 6H-6J illustrate partial perspective wireframe views to more directly visualize the latching member (612) and cantilevered members (616) relative to the needle portions (48, 83, 50, 111).

FIG. 6Z also illustrates a distal seal (620) configured to provide a seal between the medicine chamber (40) in a medicine container (e.g., syringe body (34)) and the exterior surfaces of the needle spine assembly (76). Preferably, the distal seal (620) is configured to provide a seal around the outside of the needle joining member (83). This seal is further configured to provide a seal between the medicine chamber (40) and the interior surfaces of the needle coupling assembly (606). FIG. 6Z also shows a snap fit (630) between a distal end of the medicine container (e.g., syringe body (34)) and a proximal end of the needle coupling assembly (606).

Referring to FIGS. 6AA-6CC, the distal seal (620) is shown in perspective views (FIGS. 6AA-6BB) and a cross sectional view (FIG. 6CC). The distal seal (620) includes a medicine container contact seal surface (622). This contact seal surface (622) further includes a proximally projecting seal (624) configured to seal against the outside surfaces of the needle spine assembly (76) when the distal seal (620) is coupled to the medicine container (e.g., syringe body (34)) and the needle coupling assembly (606). The distal seal (620) is also includes internal sealing glands (626) to seal on the outside of the needle joining member (83). Moreover, the distal seal (620) includes a needle coupling assembly contract surface (628) configured to seal against an inside surface of the needle coupling assembly (606) when the distal seal (620) is coupled to the needle coupling assembly (606).

FIG. 6E illustrates aspects of a needle spine assembly (76), comprising the elements of a needle assembly without the needle coupling assembly (606). The distal portion (48) of the needle spine assembly (76) comprises a sharpened hypodermic needle tip formed on an injection member (78). As shown in FIGS. 6G and 6H, the needle proximal end (50) also comprises a sharped tip (86) that is formed into a coupling member that forms the distal portion. A hollow joining member (83) couples the coupling member to the tubular injection member (78). The injection member (78), sharpened tip (86) on the needle proximal end (50), and hollow joining member (83) may be held together with interference fits, welds, and/or adhesives. The most proximal end (84) of the needle proximal end (50) in the depicted embodiment comprises a "harpoon" style geometry configured to stab into and hold onto a compliant member to which it may be interfaced, as described in further detail below, for withdrawal of the needle spine assembly (76) into the plunger housing member (69). The needle proximal end (50) may be formed from a thin sheet metal component using laser cutting, etching, stamping, and/or machining techniques, for example. Referring to FIGS. 6W-6Y, the hollow joining member (83) also may provide a fluid pathway from the medicine chamber (not shown; see e.g., 40 in FIG. 6M and 42 in FIG. 11A) into the inner diameter of the tubular injection member (78). This fluid pathway may include an opening (85) at the proximal end of the hollow joining member (83) adjacent to the needle proximal end (50) as shown in FIGS. 6W and 6Y. As shown in FIG. 6Y, the opening (85) may be formed by cutting or skiving the proximal end of the hollow joining member (83). Referring to FIG. 6X, an alternative fluid pathway may be formed through an opening (85) (e.g., a hole or a slot) in the side wall of the hollow joining member. The transition between the outer diameter (87) of the hollow joining member (83) and the outer diameter (88) of the needle proximal end (50) may be smoothed to reduce retraction forces required to retract the needle spine assembly (76) through the stopper/plunger tip (36) at least partially into the plunger member housing (not shown, see e.g., 69 in FIG. 6M).

Returning to FIGS. 6A-6B, for example, a safe injection configuration comprises a conventional syringe body (34), fitted with a plunger tip (36) configured to be pierced by proximal needle end (50) at an appropriate time to assist with needle retraction; this plunger tip (36) is coupled to a plunger manipulation interface (128) by a plunger housing member (69) defining an inner volume occupied by various other portions of the assembly, as described below, which are configured to retract the needle at an appropriate time in the sequence of use. A needle coupling assembly (606) described above is included in the illustrated embodiment; other embodiments may comprise Luer type or cartridge type needle assembly coupling to the syringe body (34). The depicted version of the syringe body (34) comprises a conventional small-diameter flange (33) geometry which may be manipulated or interfaced between the index and middle fingers of the operator, for example, while a thumb of the operator is interfaced with the plunger manipulation interface (128). FIGS. 6A and 6B illustrate pre-utilization assemblies with a needle cover (63) in place to mechanically isolate the distal needle tip (48). Referring to FIG. 6M, the needle cover (63) has been removed and the assembly is readied for injection into a patient. Referring to FIG. 6N, after the distal needle end (48) has been inserted or stabbed into a tissue structure of a patient, the plunger manipulation interface (128) may be briefly pulled away from the syringe body (34) to "aspirate" or check to confirm that the needle distal tip (48) has not come to rest within an unwanted tissue structure portion, such as a vessel. For example, if the distal needle tip (48) has come to rest within a vessel, upon slightly pulling out the plunger tip (36), a small marking of blood of the patient is likely to appear within the medicine chamber (40), and the operator can see this and reposition the distal needle tip (48).

Referring to FIG. 6O, with the desired distal needle tip position confirmed, the plunger manipulation interface (128) is inserted relative to the syringe body (34) and the medicine is expelled out of the medicine chamber (40), through the needle tip (48), and into the patient. FIG. 6P illustrates a cross sectional view of the configuration of FIG. 6O. Referring to FIG. 6Q, with complete seating of the plunger tip (36) into the syringe body (34), the proximal needle end (50) is stabbed through the plunger tip (36), while elastic deformation of the material comprising the plunger tip (36) allows the plunger tip to reach the bottom of the syringe body to expel all of the medicine, and trigger the spring to retract the needle while accounting for geometric variation of syringe body and other components due to manufacturing and assembly tolerances. Referring to FIG. 6R, the needle retention feature (712) is configured to prevent pull-out of the proximal needle end (50) once it has been stabbed into and captured by the needle retention feature (712). The capturing interaction between the needle retention feature (712) and the proximal end harpoon (84) of the needle proximal end (50) is configured to allow relatively easy motion (using less force) in the compressive/coupling direction (i.e., during the stabbing-in motion with the proximal end harpoon 84 of the needle proximal end 50), and relatively difficult motion (withstanding more force) in the axial tension/decoupling motion (i.e., with a needle retracting load from the plunger assembly to pull the needle distal tip into a safe configuration).

With complete insertion of the plunger tip (36), the needle latch (616) is configured to become unseated from its previous interface position (111) against the needle body, as shown in FIG. 6R, to allow for retraction of the needle; concomitantly, as is shown in the progression from FIGS. 6Q/6R to FIGS. 6S/6T, the proximal needle end (50) is configured to directly abut or compress against an unlatching member (710) or rod that is configured to allow a rotatable latching member (714) to be positioned or configured into either of two states. The first configuration of the rotatable latching member (714), shown in FIG. 6Q and associated cross section FIG. 6R, is the "latched" condition, where the rotatable latching member (714) is retained in the position shown in FIG. 6R by a proximal feature comprising the proximal aspect of the unlatching member (710). In this latched condition, a load generated by a compressed energy-storing member (718), such as a spring, is reacted by the geometric state of the latching member (714), maintaining the compressed state of the energy-storing member (718). The second configuration of the rotatable latching member (714), shown in FIG. 6S and associated cross section FIG. 6T, may be termed the "unlatched" condition wherein the unlatching member (710) has been moved more proximally with loading from the needle proximal end (50) to cause the rotatable latching member (714) to be free to rotate. In this second configuration, with rotation of the rotatable latching member (714) out of the lock interface window (716) as shown in FIG. 6T, the load generated by the compressed energy-storing member (718) is not reacted by the rotatable latching member (714), and the energy-storing member (718) is free to expand longitudinally, as shown in FIG. 6U and associated cross section FIG. 6V, thereby pulling the needle retention feature (712) and intercoupled needle spine assembly (76) proximally, which retracts the needle spine assembly (76) through the plunger tip (36) where the needle distal tip (48) is safely encapsulated in at least a portion of the plunger housing member (69) and/or inside at least a portion of the needle coupling assembly (606). As such, the rotatable latching member (714) is a "living hinge". Thus referring to FIG. 6T, in the unlatched configuration, the unlatching member (710) is moved proximally and the rotatable latching member (714) is configured to rotate from a latched position, wherein the rotatable latching member (714) is seated within a lock interface window (716), and wherein this interfacing of the latch position maintains the energy storage member (718), which may comprise a spring, in a stored configuration, to an unlatched position, wherein the rotatable latching member (714) is rotated slightly out of the lock interface window, as shown in FIG. 6S, and the cross sectional view of FIG. 6T, to free the energy storage member (718) to accelerate and move the unlatching member (710) and intercoupled retention features (712) to the right as the potential energy stored in the energy storage member (718) is released, thereby pulling the intercoupled proximal needle end (50) along with it, as shown in FIG. 6U and the cross sectional view of FIG. 6V, such that the needle distal tip (48) becomes safely encapsulated within the plunger tip (36) and the plunger housing member (69) (i.e., into a protected configuration). Once in this configuration, the needle coupling assembly (606) preferably is configured to prevent any further re-insertion of the distal needle tip (48) relative to the syringe body (34); in other words, needle tip re-exposure is prevented with such a safety configuration. In one embodiment the plunger tip (36) may be solid, not having any pre-formed through-holes to facilitate transection of the needle proximal end (50). As shown, for example, in FIG. 6V, complete retraction of the needle through the plunger tip (36) requires the needle to penetrate the plunger tip. To pull the needle through the plunger tip (36) without losing "grip" on the needle proximal end (50), the penetration force of the needle through the plunger tip (36) generally must be low enough so as not to exceed the "gripping load" provided by the interface that has been formed between the proximal needle end (50) and the needle retention features (712) with stabbing of the proximal needle end (50) through the plunger tip (36). With one embodiment, experimentation has shown that the penetration force between the needle spine assembly (76) and the plunger tip (36), or the needle joining member (83) and the plunger tip (36), is between about 1 lb. and about 7 lbs., depending upon the rubber or elastomeric material used to manufacture the plunger tip (36), or the plastic or metal used to manufacture the needle joining member (83). To further minimize resistance as the needle spine assembly (76) is pulled through the elastomeric plunger tip (36), in one embodiment it is desirable to create a chamfered, tapered, and or blended transition geometry on the proximal geometric aspects of the needle joining member (83).

As was discussed above in reference to FIGS. 6Q and 6R, in the embodiment of FIGS. 6A-6CC, the elastomeric material comprising the plunger tip (36) is utilized to assist in dealing with slight geometric tolerances which may be present due to manufacturing, assembly, temperature, or other factors. In use, the operator feels the full insertion position of the plunger tip (36) relative to the syringe body (34) coming by an increased insertion load required to continue inserting the plunger tip (36). The operator may be trained to continue such insertion against such increasing insertion resistance load until a "click" sound is heard, which signifies that the needle latching mechanism (616) has been triggered, thereby releasing the needle longitudinally relative to the syringe body (34) so that it may be retracted. In one embodiment, the "click" sound is caused by rotation of the rotatable latching member (714), which is driven by the energy storage member (718), and the release of the energy stored in the energy storage member to retract the needle into the plunger rod. The "click" sound may also provide a tactile feedback to the user that the injection has been completed by being triggered by the plunger tip (36) reaching the bottom of the medicine chamber, thus having expelled all of the medicine.

Exemplary Safe Syringe System (with Luer Needle)

As noted above, while the configurations of FIGS. 6A-6CC are illustrated using a staked needle/needle housing/latch configuration as described in detail here, such configurations may also utilize a removable Luer type (e.g., Luer lock, Luer slip, Luer taper, etc.) coupling and associated hardware.

Figure 7A:
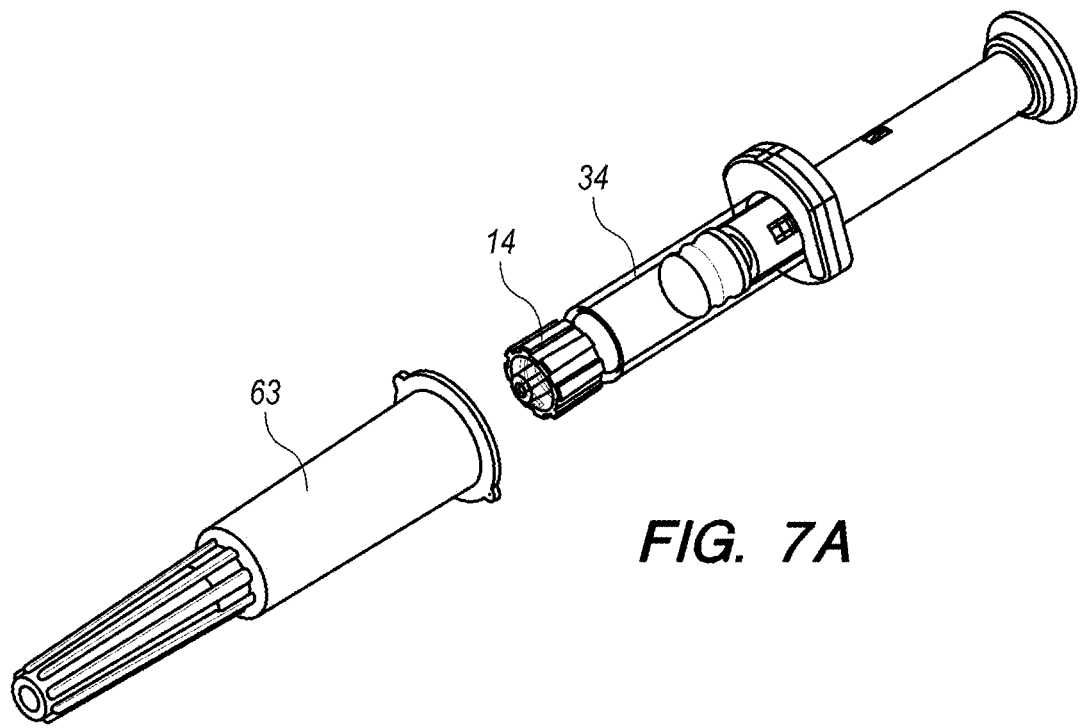
FIGS. 7A-7N illustrate a safe injection system according to another embodiment.
Figure 7B:
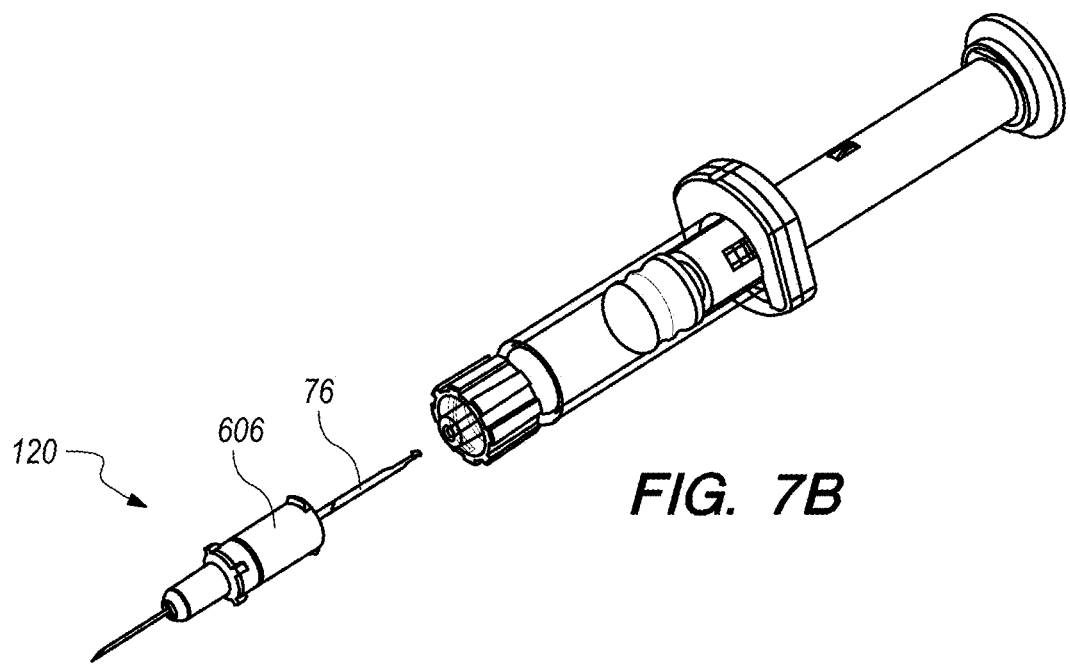
Figure 7C:
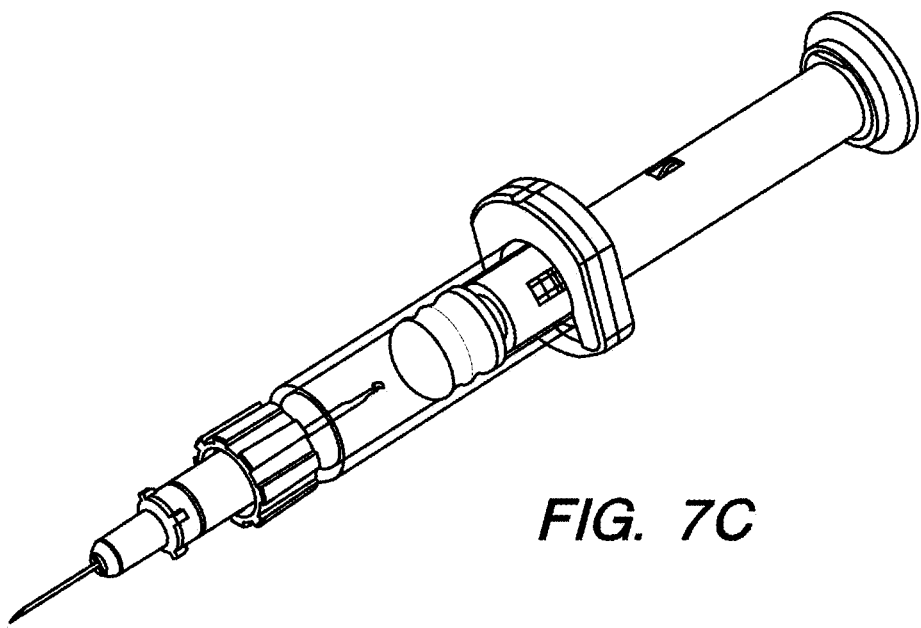
Figure 7D:
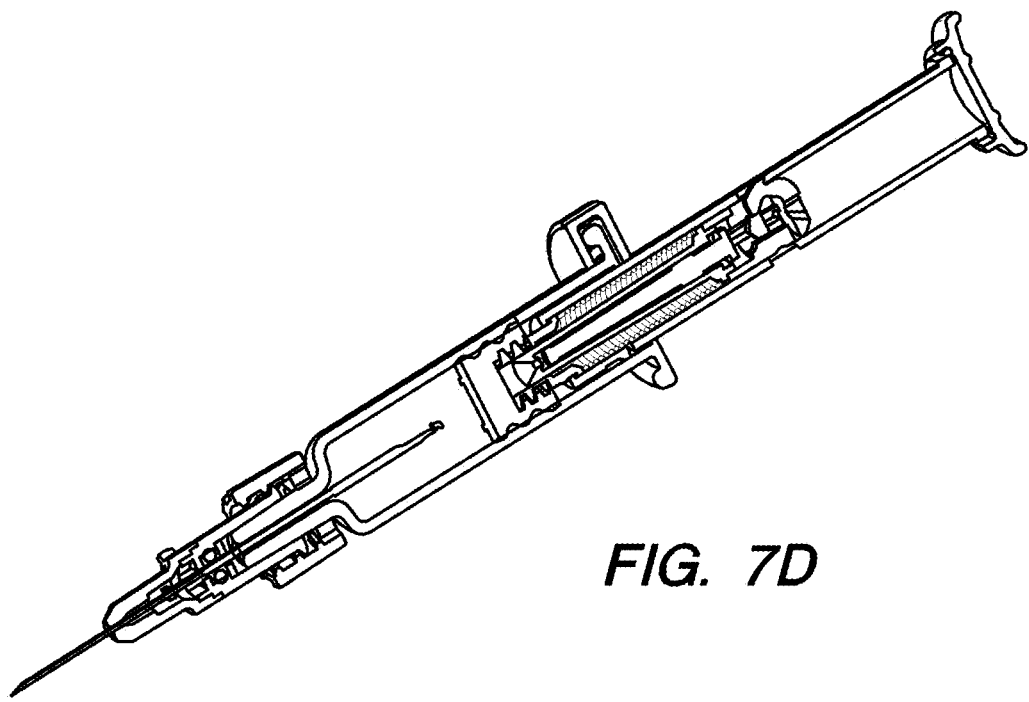
Figure 7E:
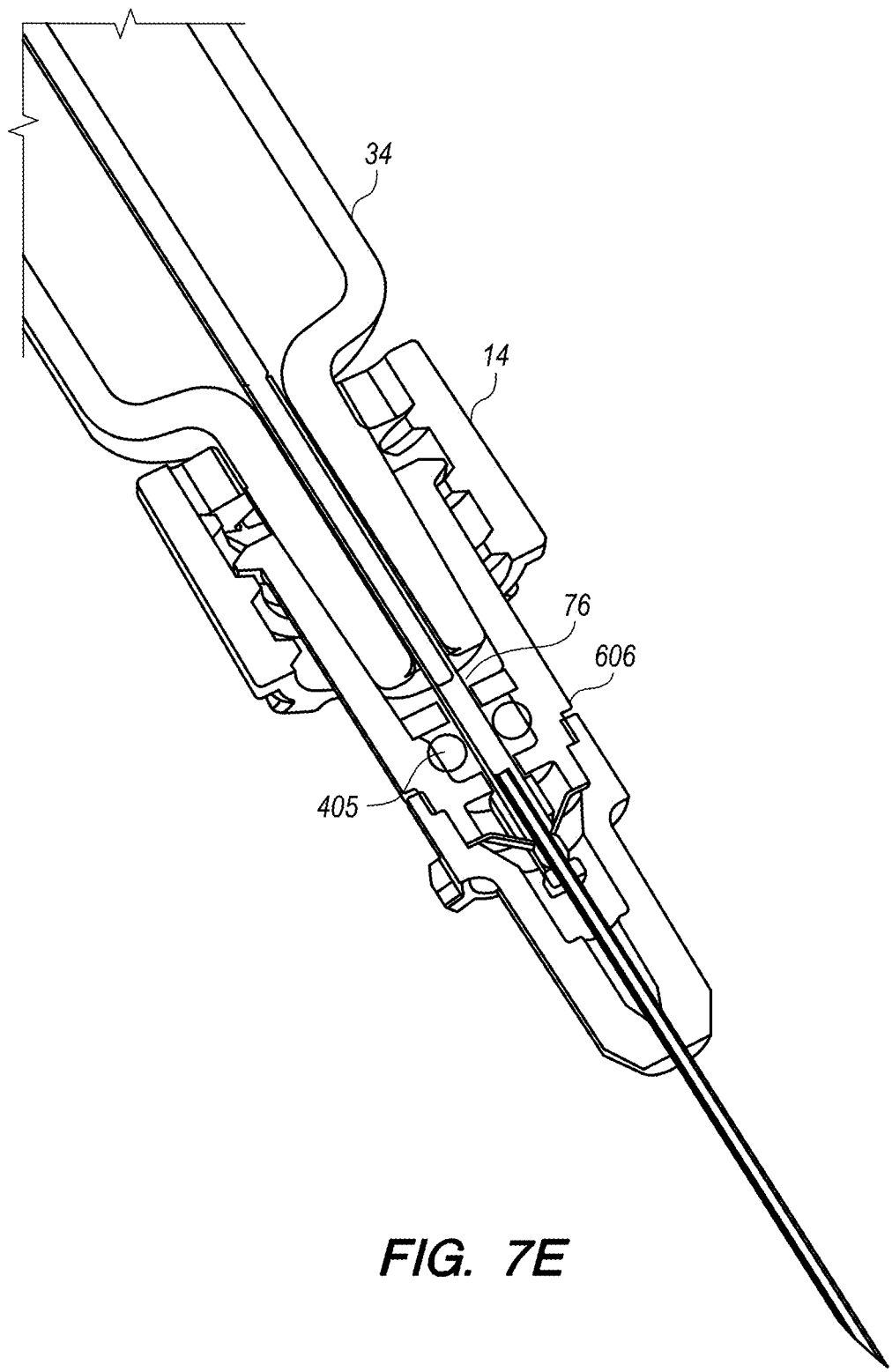
Figure 7F:
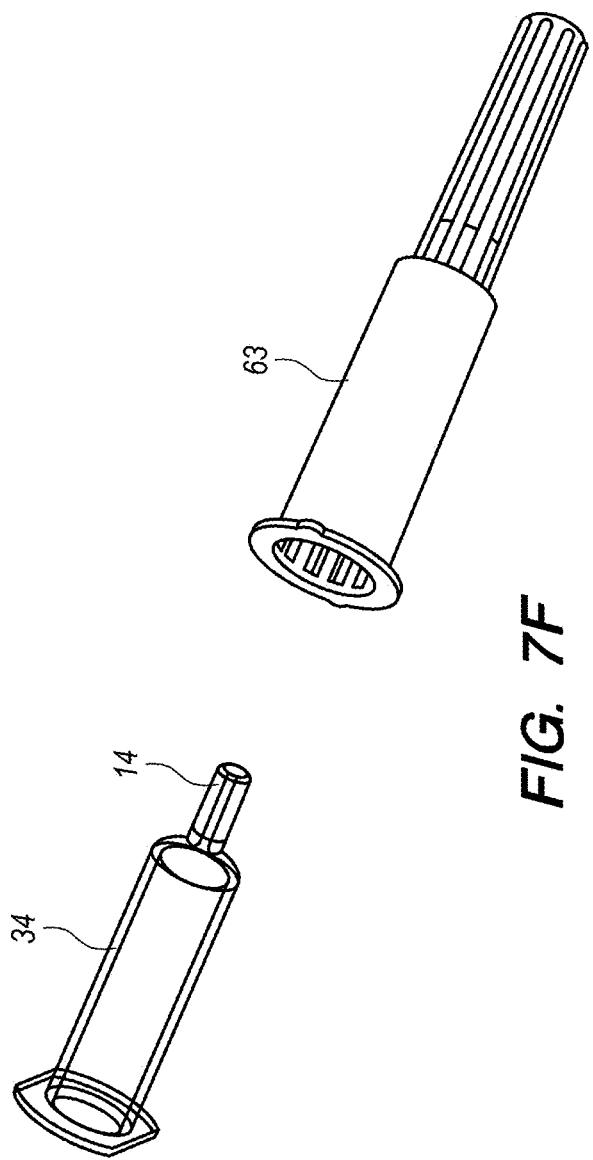
Figure 7G:
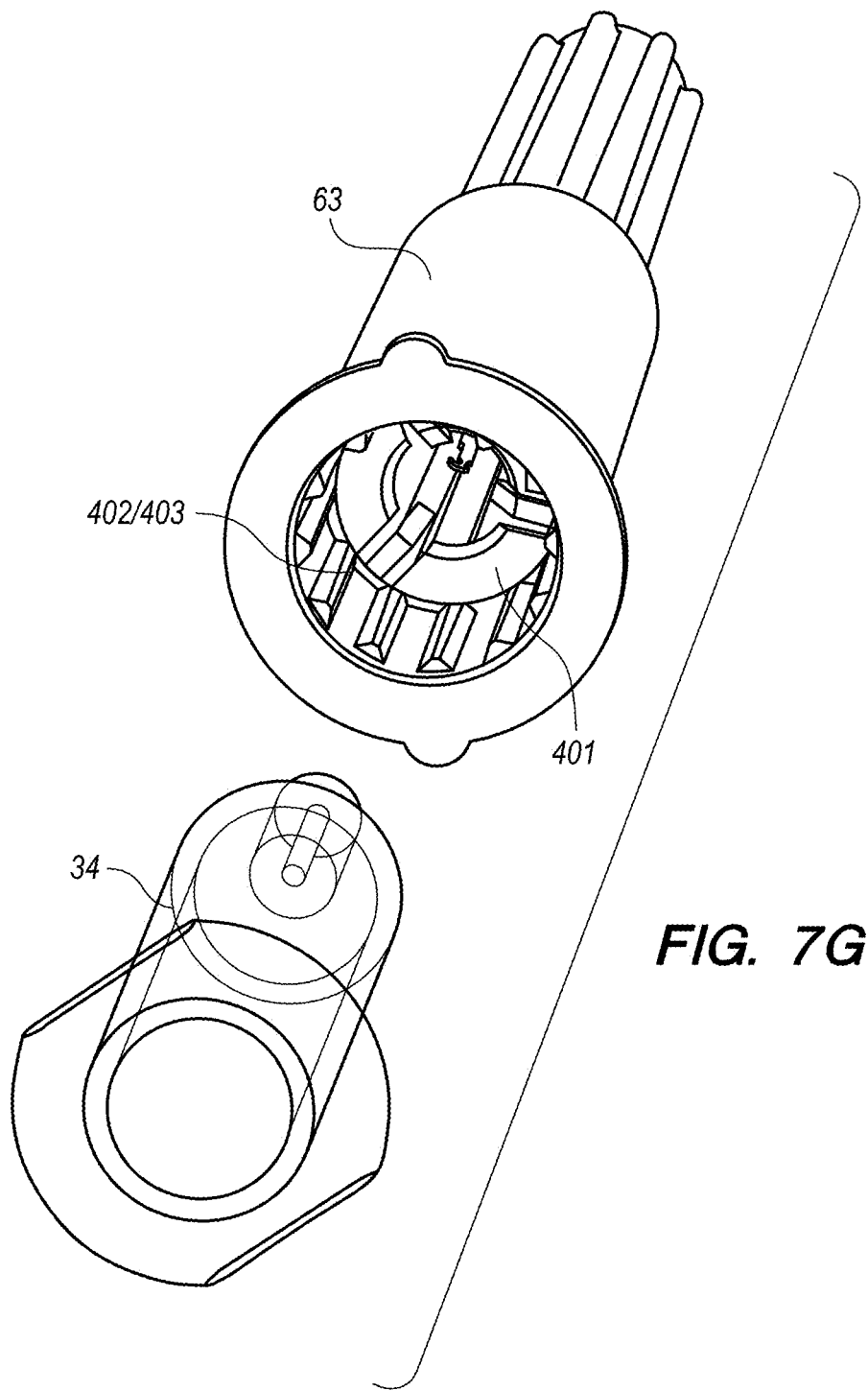

For instance, FIGS. 7A-7E illustrate a syringe (34) with an integrated safety needle configured to have a user attachable needle which utilizes a Luer type coupling (14). FIG. 7A is a Luer type user attachable needle safety syringe where the Luer needle (120) comprises a needle spine assembly (74) and needle coupling assembly (606) and is housed within a needle cover/shield (63). The needle cover/shield (63) of this type may contain the rotational clutch mechanisms as described in patent Ser. No. 14/696,342, which has been incorporated by reference herein. FIG. 7B shows a user attachable Luer needle (120) in the "ready to be attached state", with the needle shield removed for clarity. FIGS. 7C-7E show perspective and cross sectional views of a syringe with the attachable needle fully attached and ready for the injection to be performed. FIG. 7E further illustrates a needle seal (405) which seals a joint between the needle spine assembly (76) and the interior of the needle coupling assembly (606).

FIGS. 7F-7N illustrate a syringe (34) with an integrated safety needle configured for use with a user attachable needle having a Luer taper or Luer slip type coupling (14). To prevent incorrect assembly by the user, the Luer slip coupling (14) and features contained in the needle cover (63) are designed to prevent insertion of the syringe (34) into the needle cover (63) before a syringe cap (400) is removed. A filter disc (401) is configured to be releasably coupled to mating features (403) inside the needle cover such that mechanical interference between the syringe cap (400) and the filter disc (401) does not allow the syringe cap (400) to advance into the cover (63).

Figure 7H:
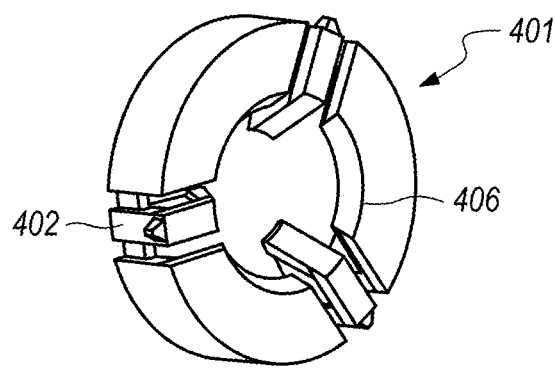
Figure 7I:
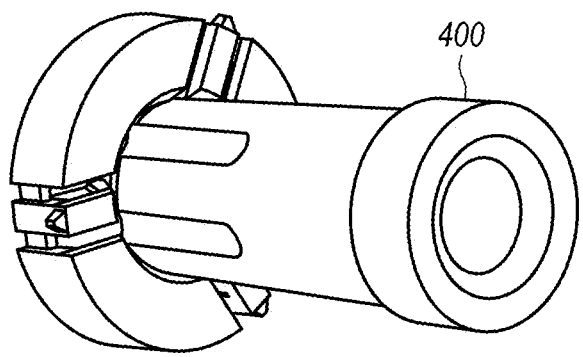
Figure 7J:
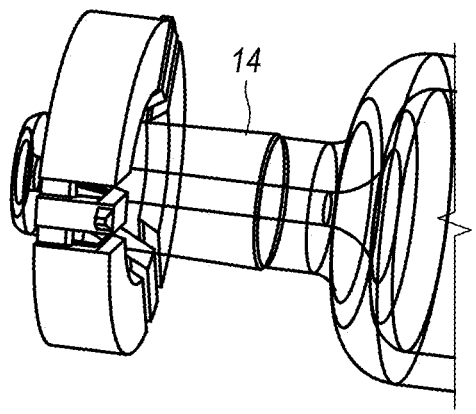
Figure 7K:
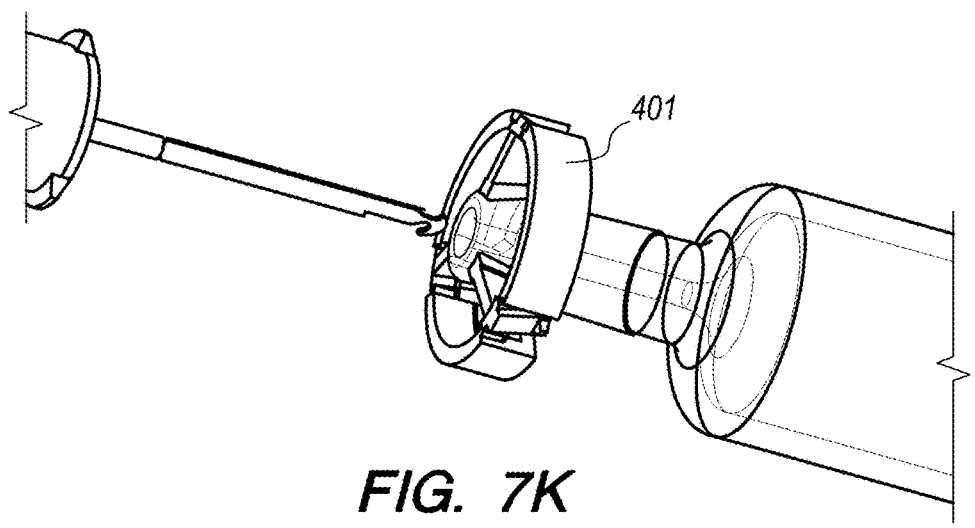
Figure 7L:
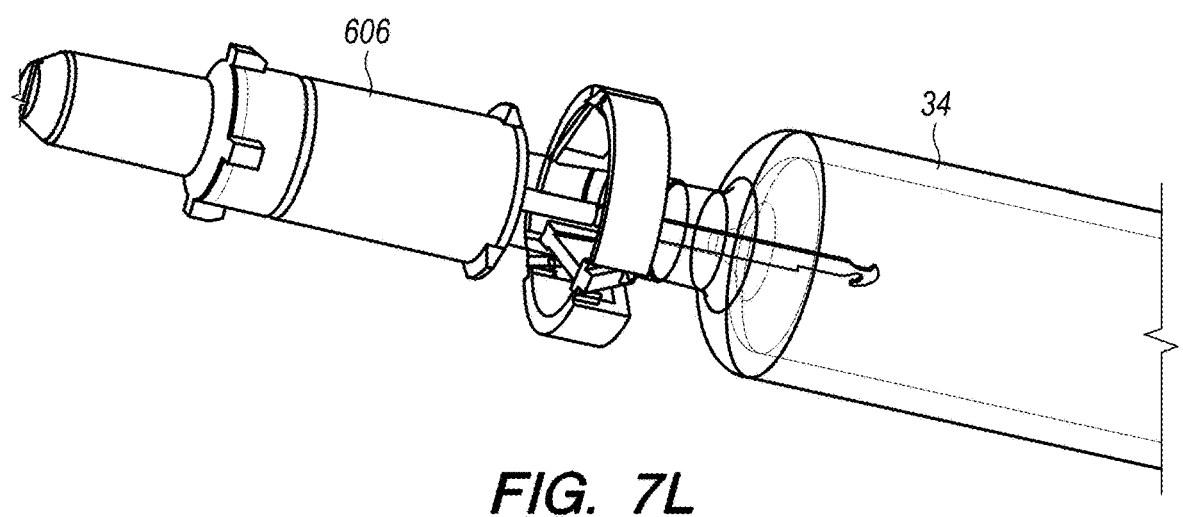
Figure 7M:
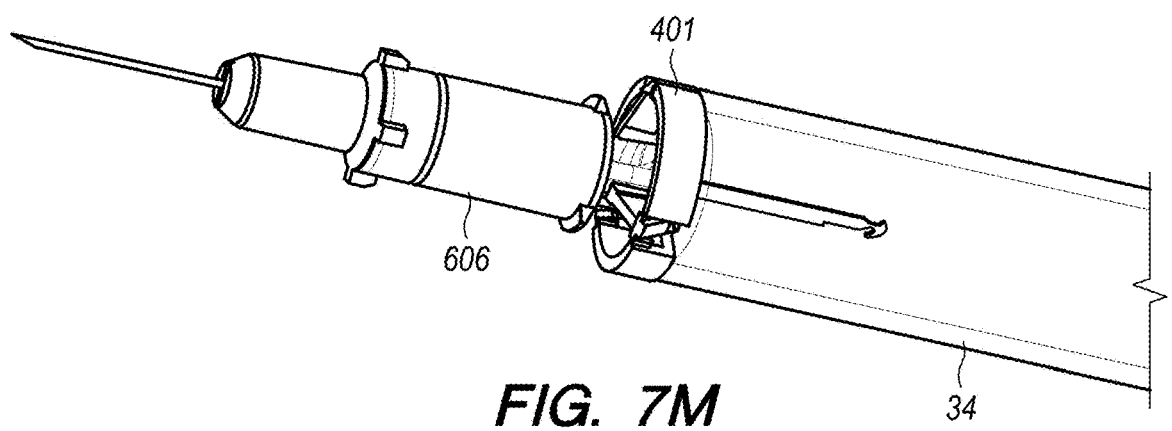

Referring to FIG. 7H-7J, in which the needle shield has been removed for clarity, the filter disc has an internal diameter (406) that is sized to let a Luer slip coupling (14) enter through the internal diameter (406), while excluding the syringe cap (400). FIG. 7I illustrates the syringe cap (400) interfacing with/being blocked by the filter disc (401). FIG. 7J illustrates the insertion of the Luer slip coupling (14) into the internal diameter of the filter disc (401). Inserting the Luer slip coupling (14) into the internal diameter of the filter disc (401) causes a plurality (e.g., three) rotatable latches (402) on the filter disc (401) to rotate and disengage from the needle cover, allowing the filter disc (401) to slide inside and allowing the Luer slip to advance into the needle cover into engagement with the needle coupling assembly (606). FIGS. 7K-7M show the filter disc (401) accepting the syringe (34) and being displaced down below the needle coupling assembly (606) as the needle coupling assembly (606) is installed onto the syringe (34).

Figure 7N:
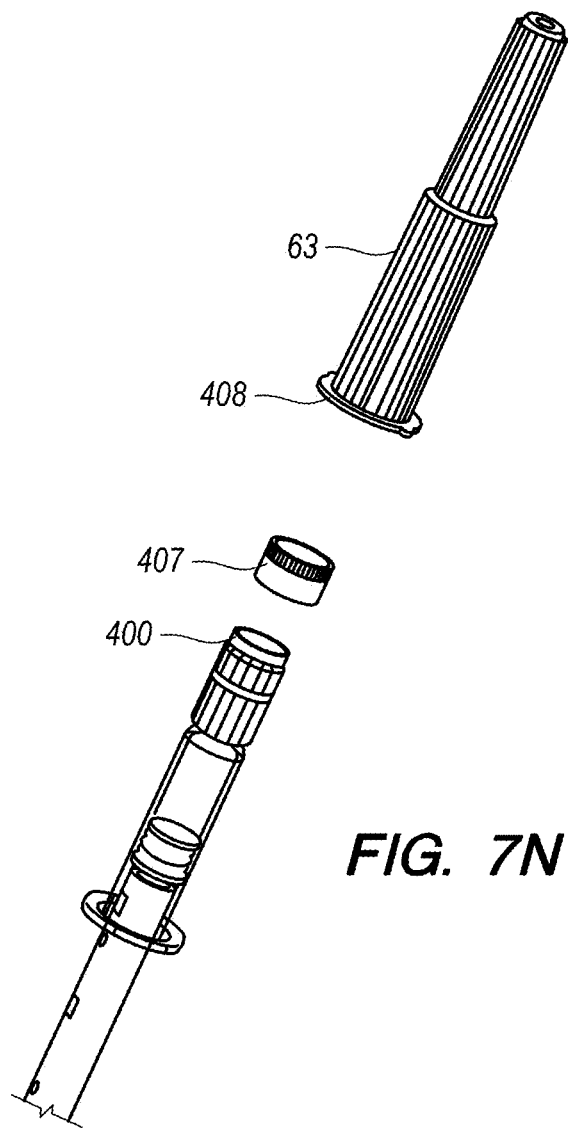

FIG. 7N illustrates an alternative embodiment of a syringe cap (400) which has an external crown (407) that is larger in diameter than the internal diameter (408) of the needle cover (63), preventing the cap from being inadvertently inserted into the needle cover (63). The external crown (407) may be integrally molded to the syringe cap, or attached by glue, welding, or press fit.

In certain circumstances, the staked needle configurations may be desired for properties such as glue/adhesive free nature of the described embodiments, silicone films which may be "baked on" due to the fact that adhesive-free staked coupling configurations may not be as limiting on temperatures during processing, and also the tungsten-free nature of the aforementioned staked needle coupling configurations, wherein preferably there is no tungsten pin exposure for forming a needle aperture, as the aforementioned staked coupling configurations utilize Luer-style syringe bodies even for staked coupling, and may be completed using tungsten-free rods. The needle retraction mechanism for the embodiment depicted in FIGS. 7A-7E is similar to the corresponding mechanisms in the embodiments depicted in FIGS. 6A-6CC and described above.

Exemplary Needle Assembly Proximal Ends and Needle Retention Features

Other and exemplary safe injection systems and various needle assembly proximal ends and needle retention features are described in Ser. No. 62/416,102, which has been incorporated by reference herein.

As described above, the retraction force required to withdraw the needle spine assembly (76) through the stopper (36) and into the plunger housing member (67, 69) is significant compared to the other forces involved in the safe injection systems. For example, in one embodiment, the force required to unlatch the cantilevered latch members (616) to release the needle spine assembly (76) is about 1.5 lbs. In that embodiment, the force required for the needle assembly proximal end (50) to penetrate the stopper (36) and/or the needle retention feature (712) is about 2.5 lbs. The gap between the penetration force (2.5 lbs.) and the unlatching force (1.5 lbs.) ensures that the needle assembly proximal end (50) will not actuate the unlatching member (710) to release the compressed energy-storing member (718) to retract the needle spine assembly (76) before the latch members (716) are unlatched. Once penetrated, the force to pull the needle spine assembly (76) through the stopper (36) and into at least a portion of the plunger assembly is configured to be about 2 lbs. In other embodiments, this needle retraction force is between about 1 lbs. and about 7 lbs. This force depends upon the thickness of the rubber which makes up the distal end of the stopper (36), and the geometry of the needle spine assembly (76). Further, for the staked type syringe, the needle tip (48) is penetrated into the protective cap (63), which can be constructed of a rubber material, for storage of the drug and to prevent leakage of the drug out of the id of the needle tip (48). Upon removal of the protective cap (63), pulling the protective cap (63) distally imparts a distally directed force on the needle tip (48) from the friction between the needle cap (63) and the needle tip (48), in a direction which would attempt to unlock the needle tip (48). Typically, the protective cap (63) imparts between 0.25 lbs. and 1.0 lb. of force on the needle spine assembly (76) during removal of the cap (63). The needle latch (612) and the cantilever members (616) provide a force to resist unlocking the needle spine assembly (76) during removal of the protective cap (63).

When unlatched, the compressed energy-storing member (718) is configured to generate a needle retraction force greater than the force required to pull the needle spine assembly (76) through the stopper (36). In one embodiment, the required needle retraction force is about 3 lbs. In other embodiments, this needle retraction force is about between about 2 lbs. and about 10 lbs. This needle retraction force must be supported by the coupling interaction between the needle assembly proximal end (50) and the needle retention feature (712). The ratio between the needle penetration force and the needle retraction force is defined herein as a penetration/retraction force ratio. The various needle assembly proximal ends (50) and needle retention features (712) described herein are configured to achieve this sizable force differential/ratio in the proximal (insertion/penetration) and distal (retraction) directions.

A. Three-Dimensional Arrowhead Needle Assembly Proximal End and Corresponding Needle Retention Feature FIGS. 8A-8K depict a needle assembly proximal end (50) and a corresponding needle retention feature (712) according to one embodiment. As shown in FIGS. 8B (perspective view) and 8C (longitudinal cross-sectional view), the most proximal end (84) of the needle assembly proximal end (50) forms a 3-D arrowhead shape (84). The 3-D arrowhead shape (84) extends proximally from an elongate needle proximal portion (102) of the needle assembly proximal end (50). The 3-D arrowhead shape (84) has an annular distally facing surface (104), a substantially constant diameter surface (106), and a proximally directed tapering surface (108). The proximally directed tapering surface (108) defines a proximally pointed cone that ends in a proximal tip (110).

The elongate needle proximal portion (102) has a substantially constant first cross-sectional diameter that abruptly expands to a greater second cross-sectional diameter at the annular distally facing surface (104). The substantially constant diameter surface (106) extends proximally from the annular distally facing surface (104), and has the second cross-sectional diameter. The proximally directed tapering surface (108) extends proximally from the substantially constant diameter surface (106), and tapers down from the second cross-sectional diameter. The proximally directed tapering surface (108) tapers down to the proximal tip (110), which has a third cross-sectional diameter that is less than the first and second cross-sectional diameters. While the 3-D arrowhead shape (84) depicted in FIGS. 8A-8K includes a substantially constant diameter surface (106), this feature is optional and other embodiments may transition directly from the annular distally facing surface (104) to the proximally directed tapering surface (108). The annular distally facing surface (104) is shown encompassing a full 360 degrees around the 3-D arrowhead shape. (84). In alternative embodiments, the annular distally facing surface may be an interrupted surface (e.g., not encompass a full 360 degrees).

The cone shape of the 3-D arrowhead shape (84) facilitates insertion of the 3-D arrowhead shape (84) into the needle retention feature (712), as shown in FIGS. 8F to 8I. The annular distally facing surface (104) facilitates an interaction between the 3-D arrowhead shape (84) and the needle retention feature (712) that prevents distal movement of the 3-D arrowhead shape (84) relative to the needle retention feature (712). The needle retention feature (712) also includes various parts that facilitate coupling of the 3-D arrowhead shape (84) and the needle retention feature (712).

Figure 8A:
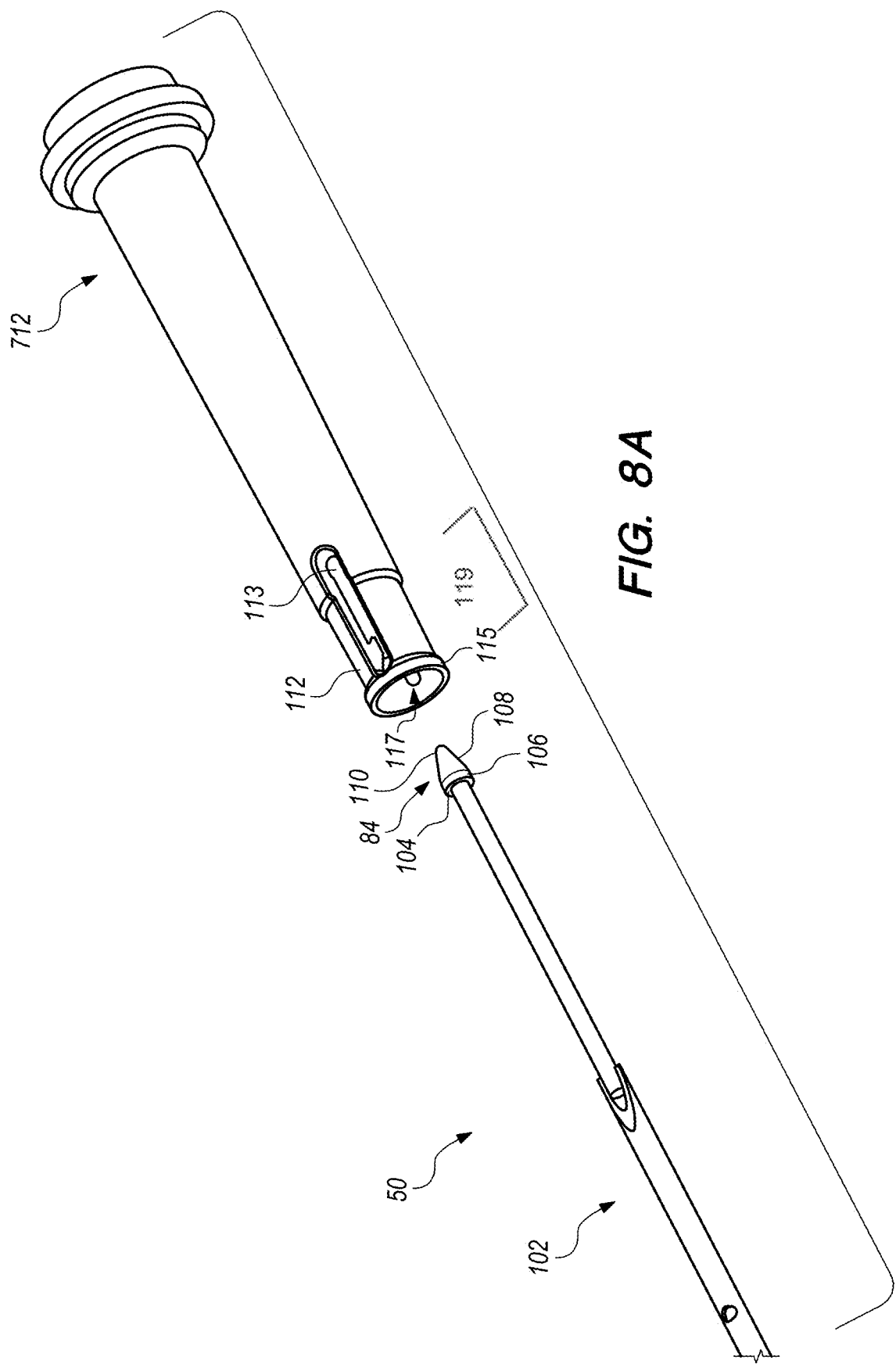
FIGS. 8A-8K illustrate a 3-D arrowhead assembly proximal end and corresponding needle retention feature for a safe injection system according to one embodiment.
Figure 8B:
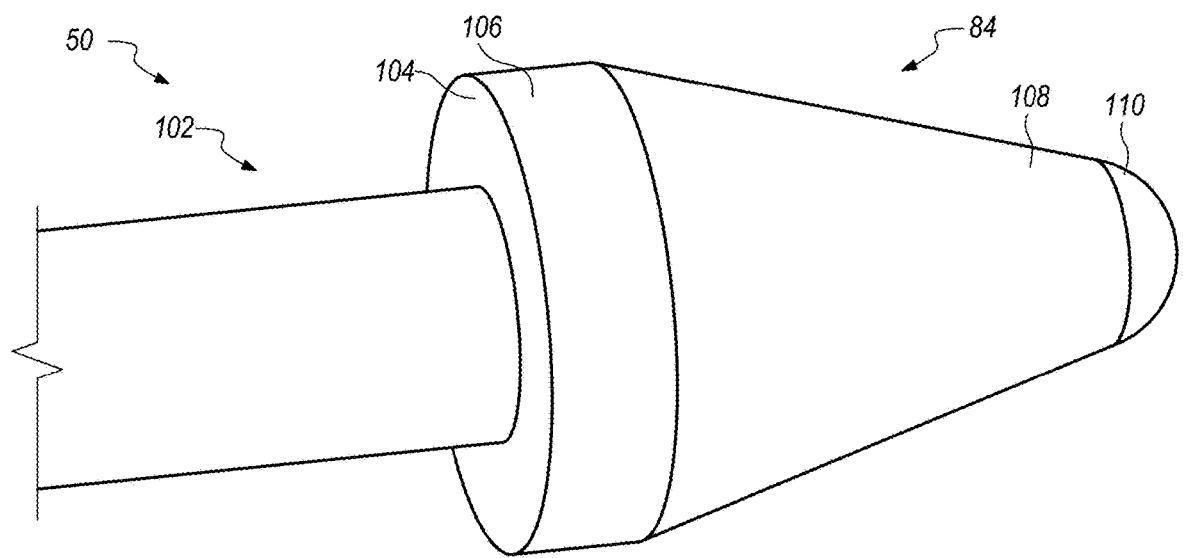
Figure 8C:
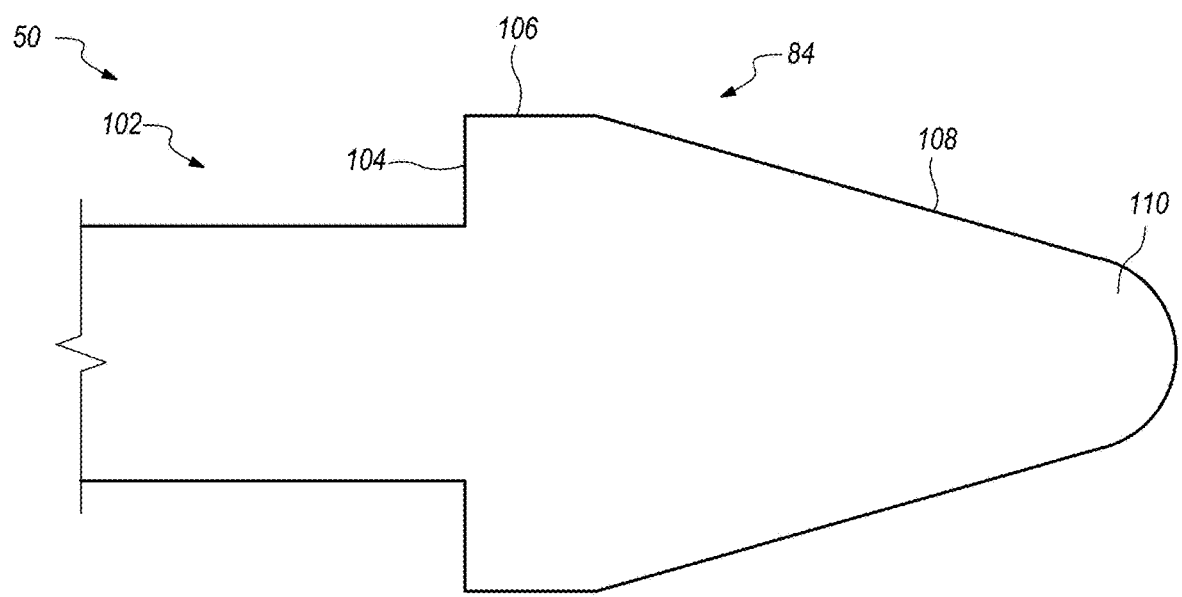
Figure 8D:
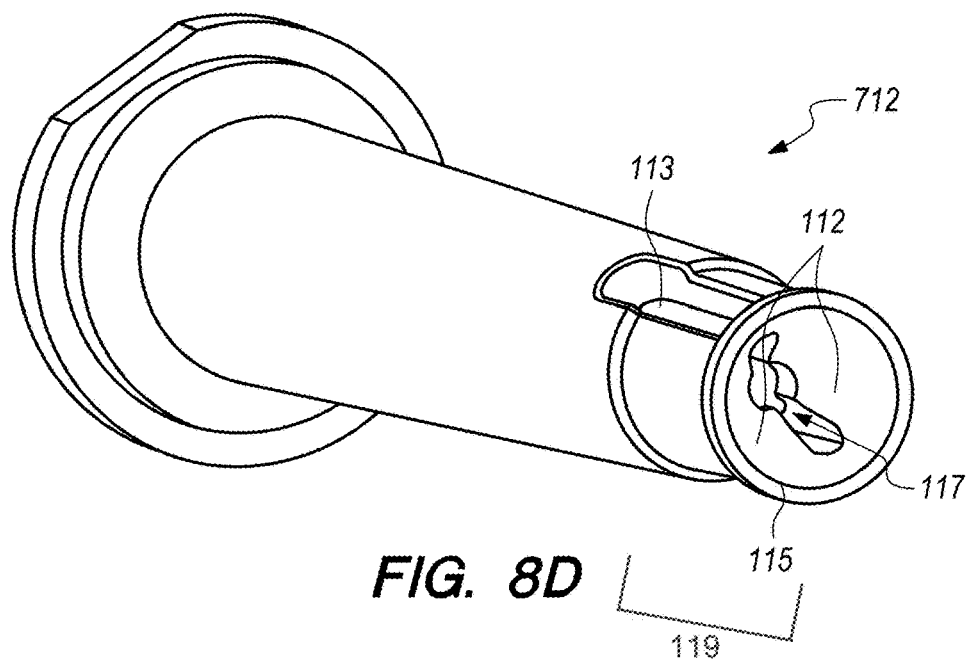
Figure 8E:
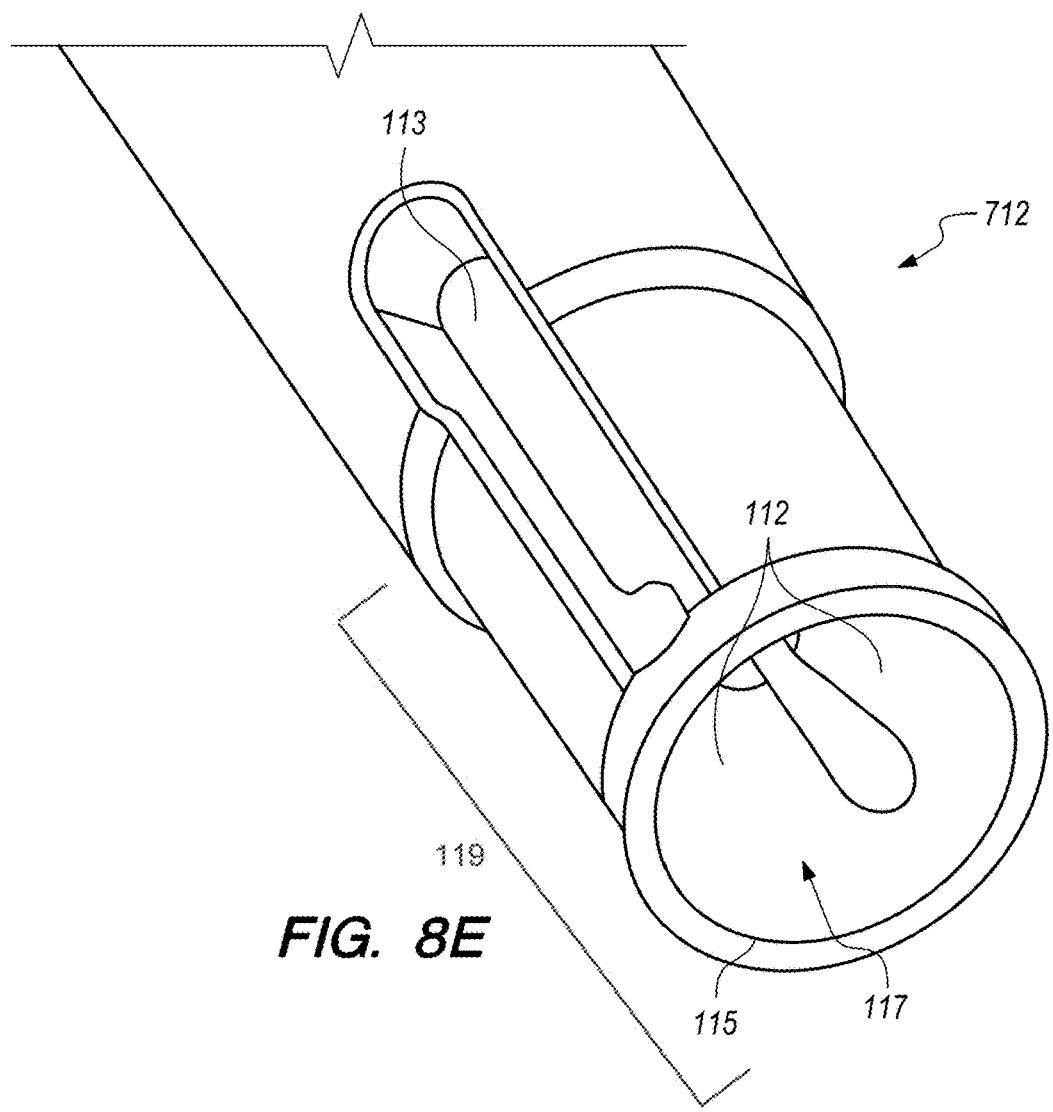
Figure 8F:
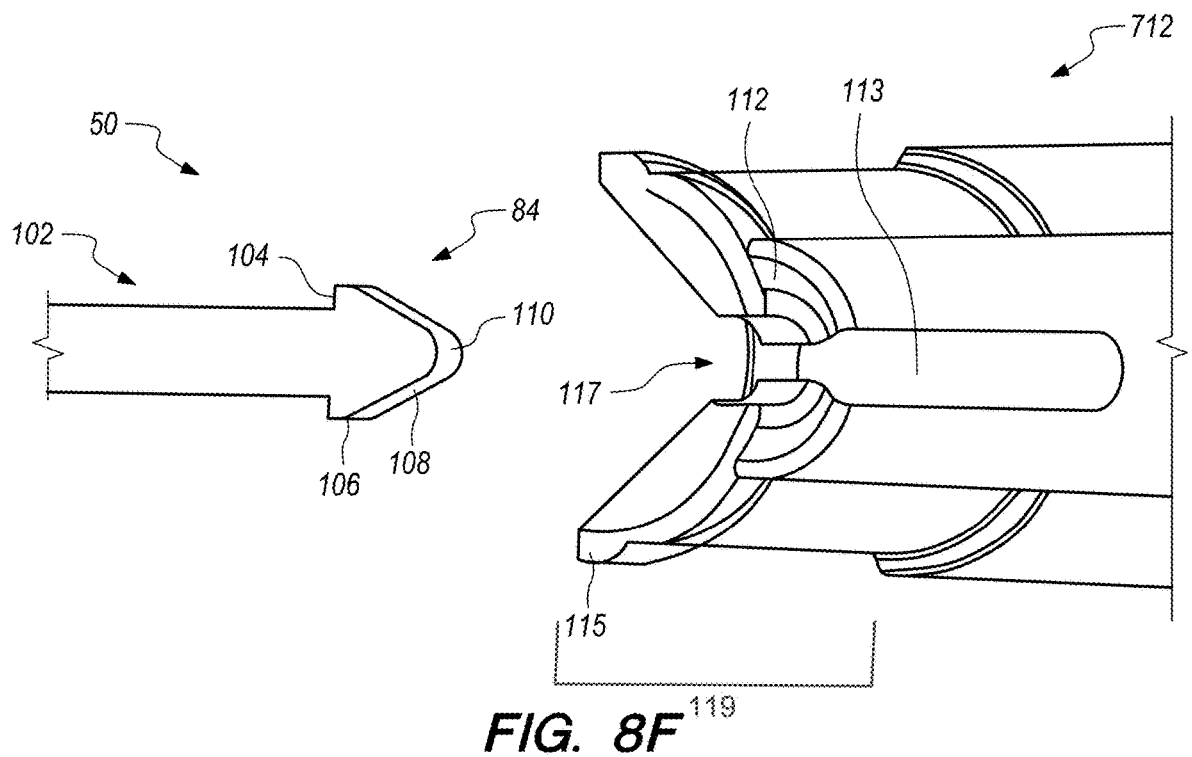
Figure 8G:
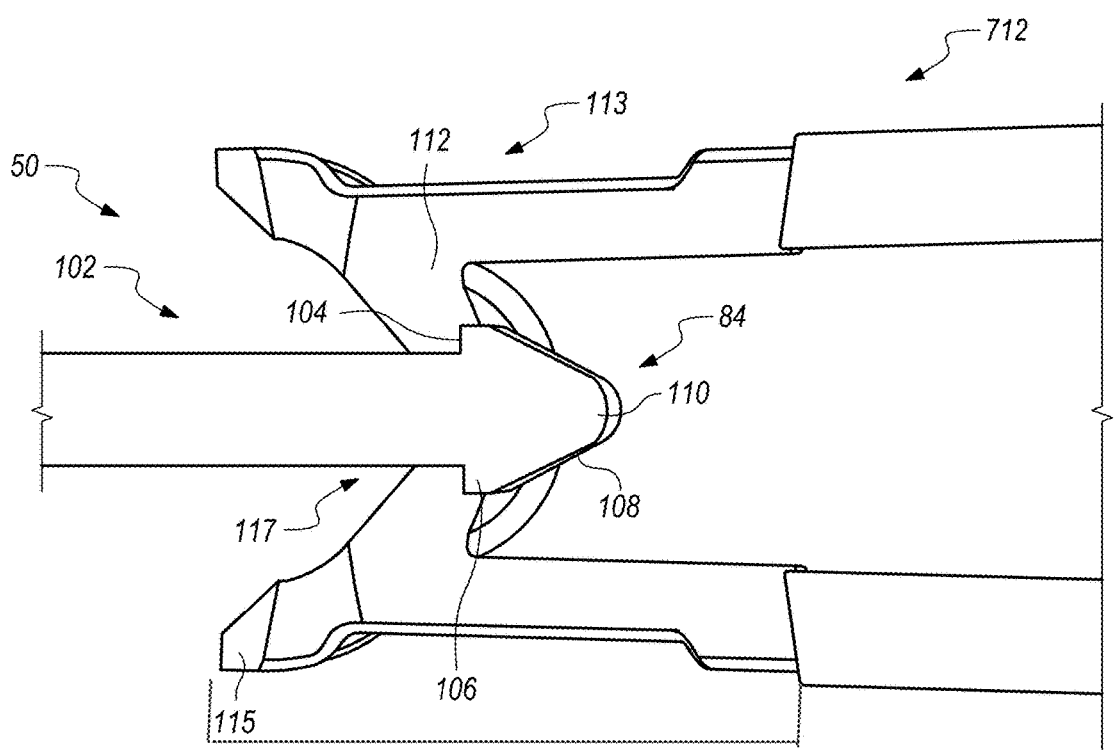
Figure 8H:
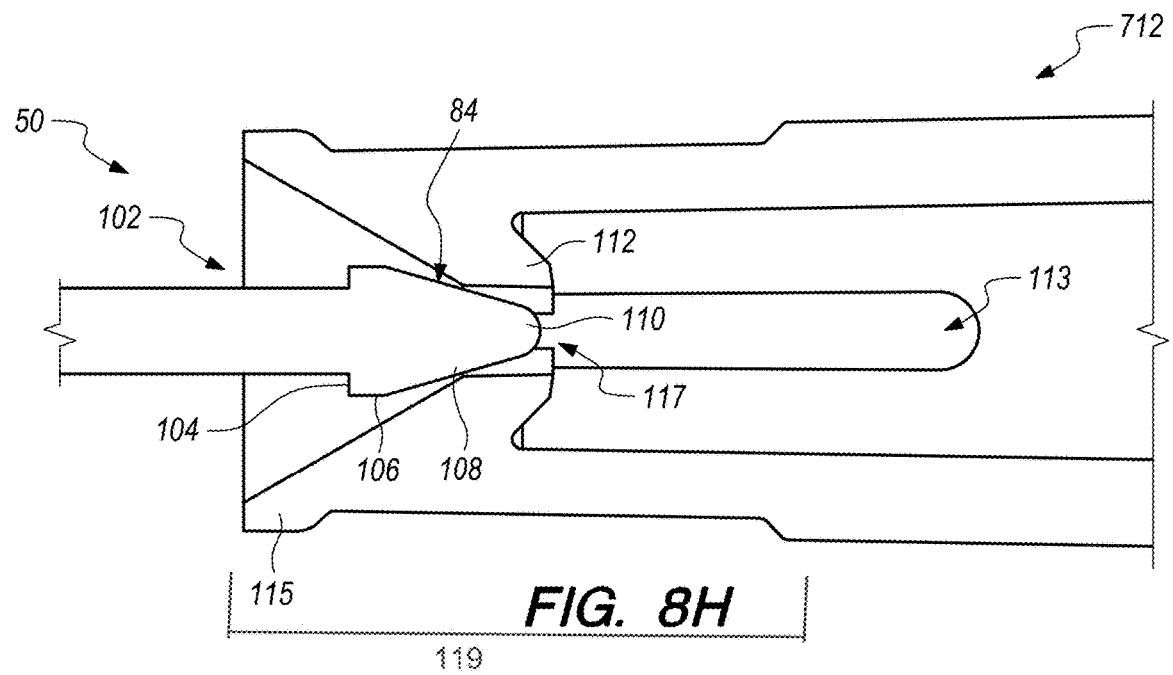
Figure 8I:
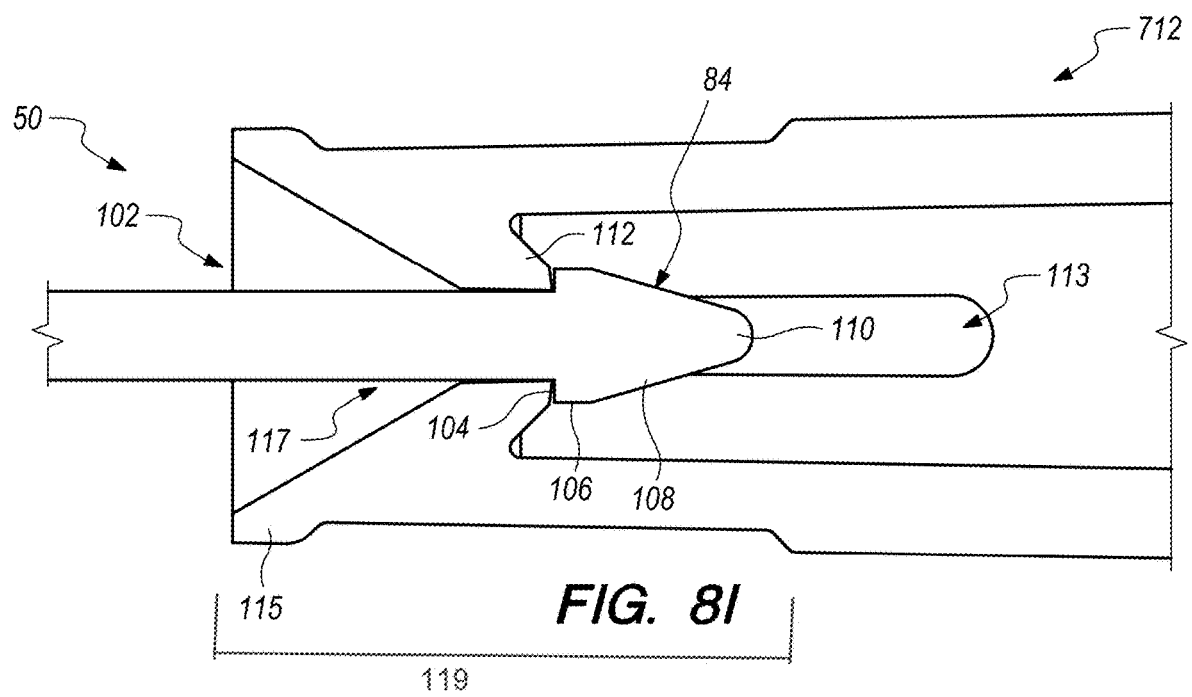
Figure 8J:
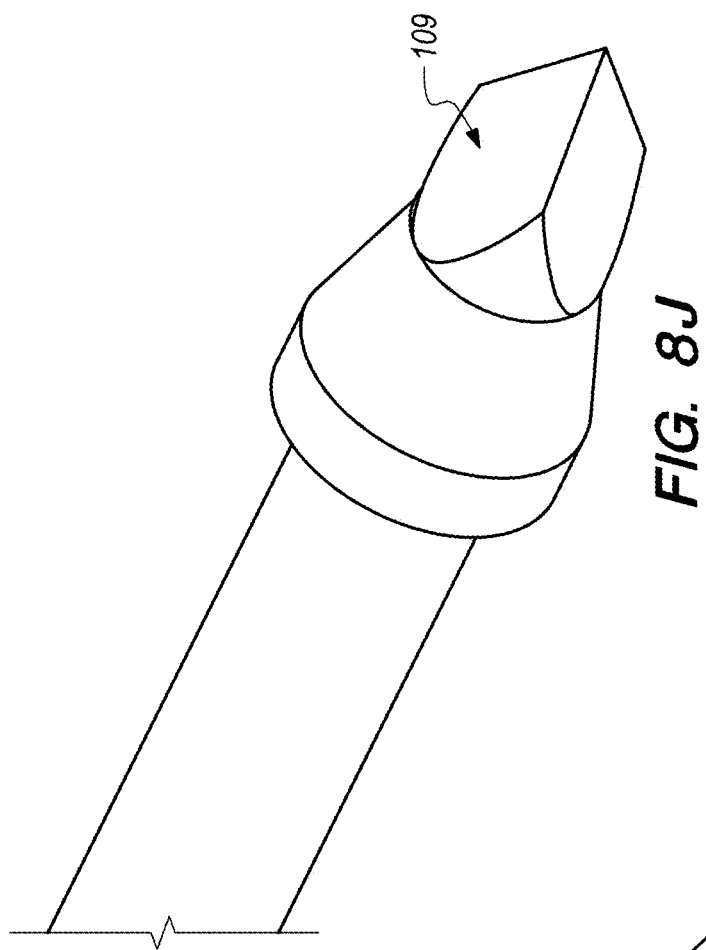
Figure 8K:
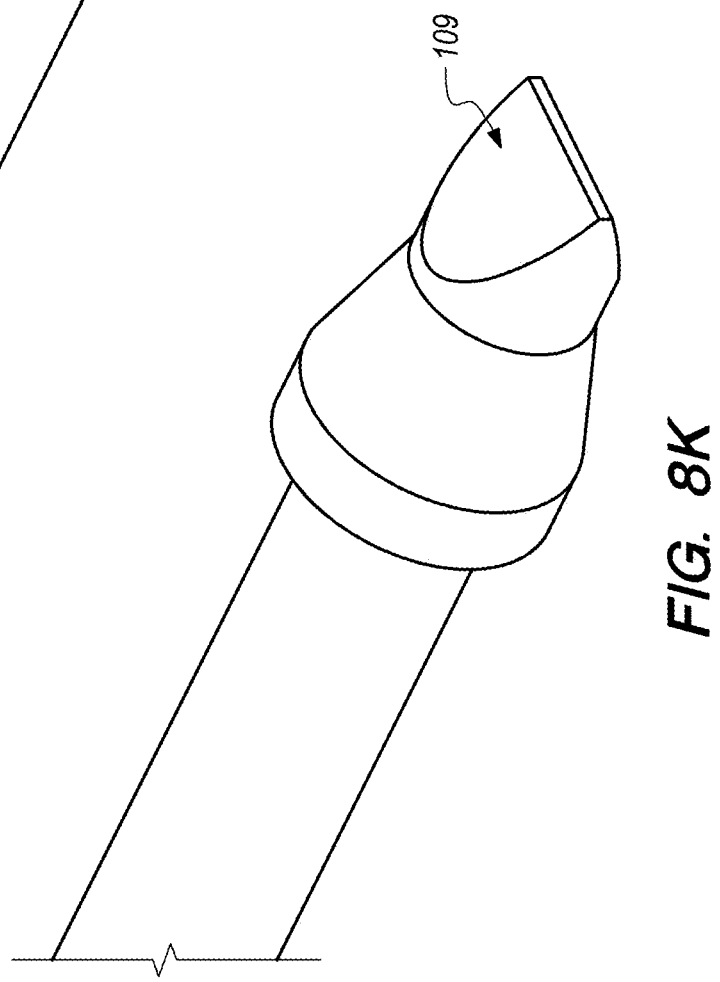

Referring to FIGS. 8J-8K, alternative tapering surface geometries are shown. The proximally directed tapering surface(s) (108) define a proximally pointed geometry that may be constructed of a series of facets (109). Two, three, or more generally proximally facing facets (109) may be used to form the distal end of the 3-D arrowhead shape (84) such that it ends in a proximal tip (110), which may be a point, an arcuate, straight line, etc. The edges where these facets come together may be sharp to facilitate cutting and dilating of the rubber stopper (36) during piercing of the stopper during injection. Alternatively, the edges between the facets may be smoothed to dilate the rubber stopper without cutting during piercing of the stopper during injection.

As shown in FIGS. 8D and 8E, the needle retention feature (712) includes a plurality of (i.e., two) latching members (112). The latching members (112) are circumferentially separated by a plurality of (i.e., two) longitudinally extending slots (113). The latching members (112) extend proximally from a rigid ring (115) and pivot about the rigid ring (115) so that each latching member (112) functions as a "living hinge." Each latching member has an arcuate cross-sectional geometry (see FIGS. 8F and 8G). Together, the latching members (112), the longitudinally extending slots (113), and the rigid ring (115) define a proximally directed funnel-shaped receiving member (119) that guides the 3-D arrowhead shape (84) into the needle retention feature (712).

FIGS. 8F to 8I show the needle proximal end (50), the needle spine assembly (76) including the needle proximal end (50), before (FIGS. 8F and 8H) and after (FIGS. 8G and 8I) coupling to the needle retention member (712) using the 3-D arrowhead shape (84). As shown in FIG. 8H, the proximal tip (110) is sized to fit through a central opening (117) defined by the latching members (112) in the receiving member (119). As the 3-D arrowhead shape (84) moves proximally through the central opening (117) and into the needle retention feature (712), the tapering surface (108) moves the plurality of latching members (112) away from each other and enlarges the central opening (117) so that the 3-D arrowhead shape (84) can pass therethrough. During the transformation into this "open configuration" of the receiving member (119), the plurality of latching members (112) pivot about the rigid ring (115) to enlarge the central opening (117). After the 3-D arrowhead shape (84) has passed through the central opening (117) and into the needle retention feature (712), the resilience of the latching members (112) moves the latching members (112) toward each, reducing the size of the central opening (117) such that the 3-D arrowhead shape (84) cannot pass therethrough. In this "resting configuration" of the receiving member (119), the annular distally facing surface (104) of the 3-D arrowhead shape (84) interfere with an interior surface of the latching members (112) to prevent distal movement of the 3-D arrowhead shape (84) relative to the needle retention feature (712), as shown in FIGS. 8G and 8I.

The latching members (112) can be made of an elastically deformable material (e.g., a polymer, or a metal) such that the central opening (117) defined by the latching members (112) in the receiving member (119) can be enlarged to allow the 3-D arrowhead shape (84) to pass therethrough in a proximal direction.

The respective three-dimensional shapes of the 3-D arrowhead shape (84) and the latching members (112) conform to each other such that their interaction couples the needle assembly proximal end (50) and the needle retention feature (712) and prevents distal movement of the needle assembly proximal end (50) relative to the needle retention feature (712). The three-dimensional shapes form a more secure connection while minimizing slippage of the needle assembly proximal end (50) relative to the needle retention feature (712). As shown in FIGS. 8G and 8I, the annular distally facing surface (104) of the 3-D arrowhead shape (84) engages both of the latching members (112) in their resting configuration, thereby coupling the needle retention feature (712) and the needle spine assembly (76) with respect to proximal movement along the longitudinal axis of the needle spine assembly (76) by increasing the surface area contacted between the 3-D arrowhead shape (84) and the needle retention feature (712). The conversion of the latching members (112) between the open configuration and the resting configuration allows the needle assembly proximal end (50) and the corresponding needle retention feature (712) to have the insertion force/retraction force differential/ratio required for operation of the safe injection system.

B. Other Needle Retention Features for Use with Three-Dimensional Arrowhead Needle Assembly Proximal End While the embodiment depicted in FIGS. 8A-8K include needle retention feature (712) having two latching members (112), other embodiments may including needle retention feature (712) having different numbers and/or configurations of latching members (112). Other embodiments of safety injection systems include needle retention feature (712) having elastically deformable latching members (112) to move between a resting configuration and an open configuration. In the open configuration, the needle retention feature (712) is configured such that the 3-D arrowhead shape (84), or other similar shaped needle most proximal end (84), can be inserted into the needle retention feature (712) with relatively low force. In the resting configuration, the needle retention feature (712) is configured such that the 3-D arrowhead shape (84), or other similar shaped needle most proximal end (84), remains coupled to the needle retention feature (712) under relatively high retracting/separating force. The structure of the 3-D arrowhead shape (84) and its corresponding needle retention feature (712) therefore achieves the insertion force/retraction force differential/ratio required for the safe injection system.

Figure 9A:
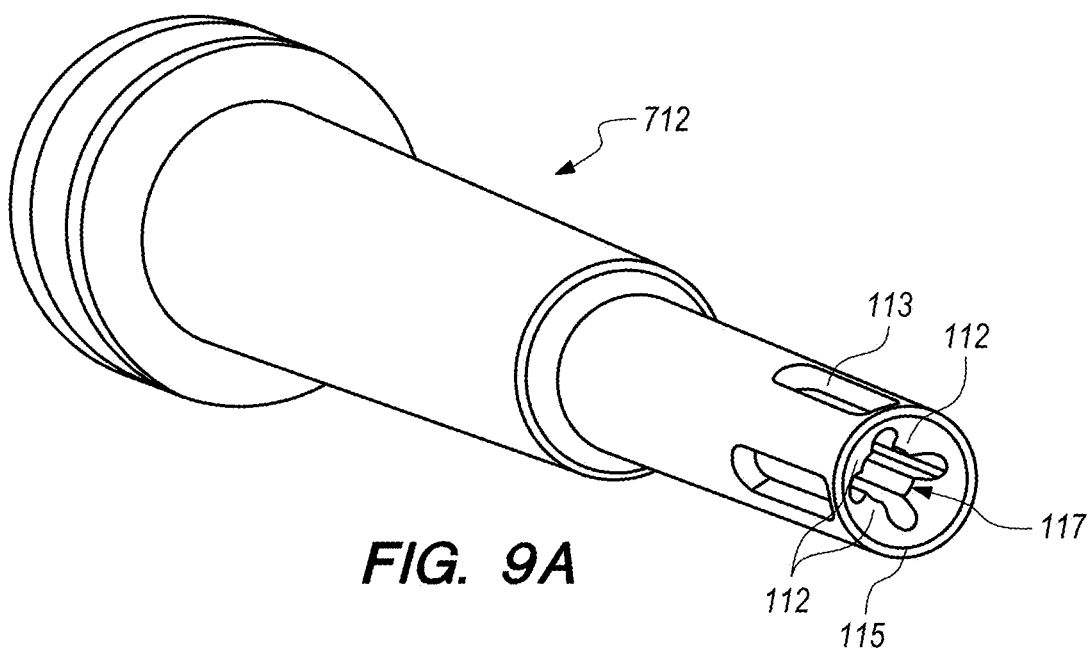
FIGS. 9A-10B illustrate two needle retention features for use with a 3-D arrowhead assembly proximal and in safe injection systems according to two embodiments.
Figure 9B:
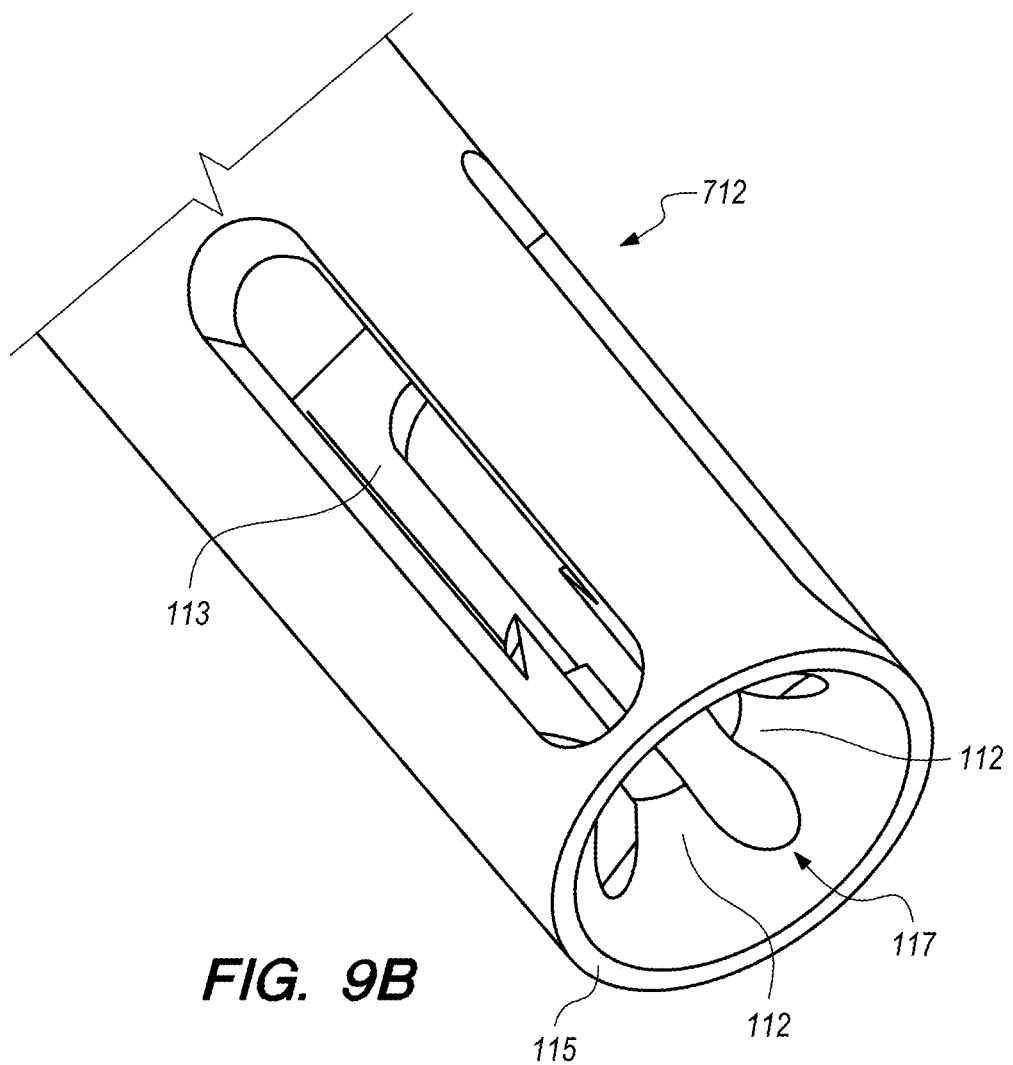

FIGS. 9A and 9B depict a needle retention feature (712) according to another embodiment. The needle retention feature (712) includes a plurality of (i.e., four) latching members (112). The latching members (112) are circumferentially separated by a plurality of (i.e., four) longitudinally extending slots (113). The latching members (112) extend proximally from a rigid ring (115) and pivot about the rigid ring (115) so that each latching member (112) functions as a "living hinge." Each latching member has an arcuate cross-sectional geometry. Together, the latching members (112), the longitudinally extending slots (113), and the rigid ring (115) define a proximally directed funnel-shaped receiving member that guides the 3-D arrowhead shape (84) into the needle retention feature (712). While two or four latching member configurations have been shown, it is possible to construct a needle retention feature with other numbers of latching features.

Figure 10A:
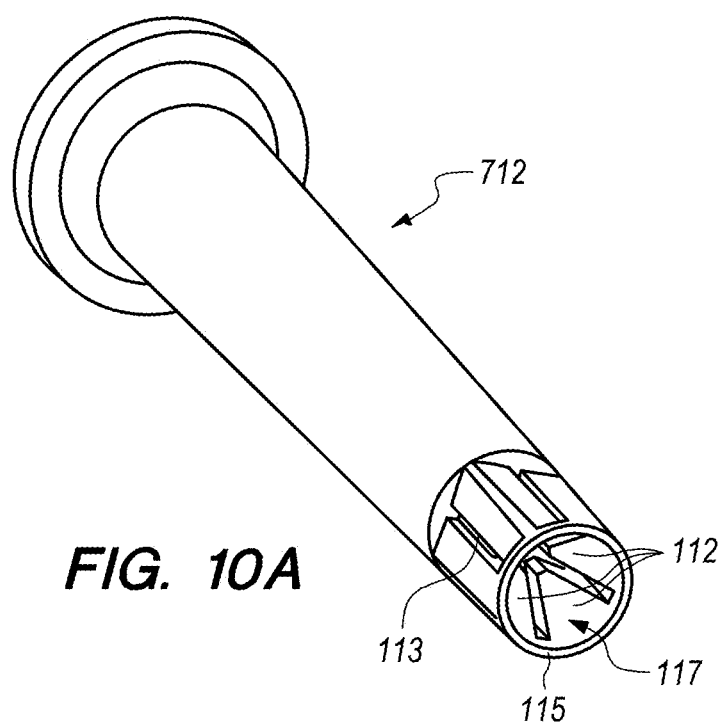
Figure 10B:
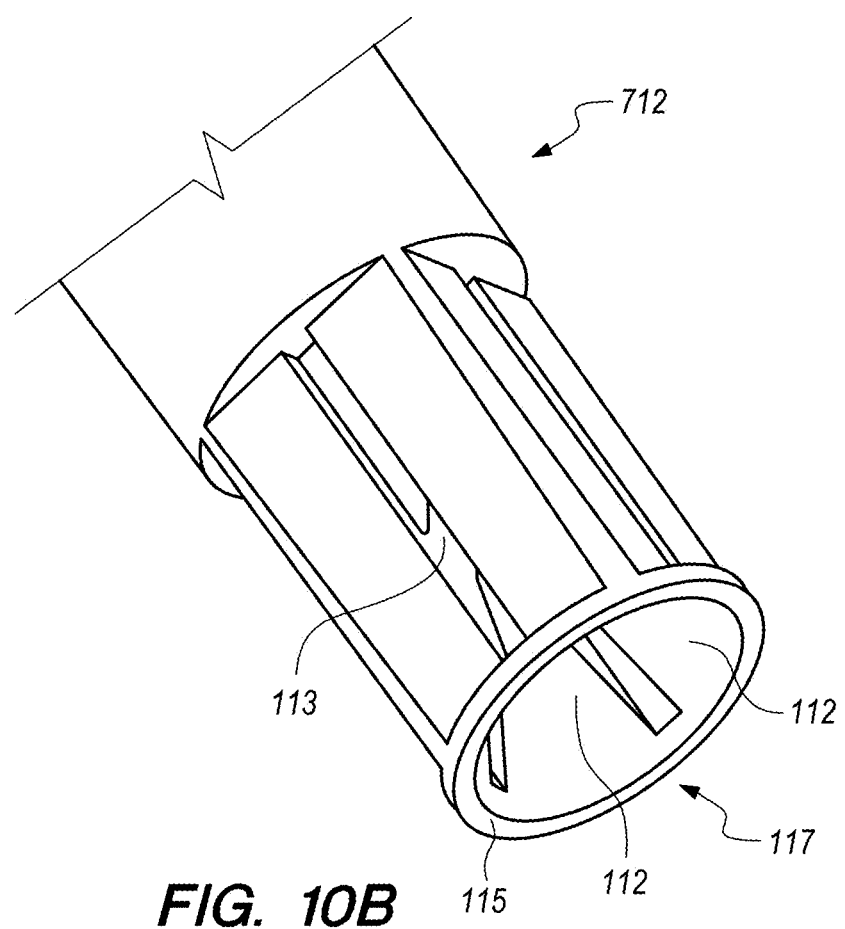

FIGS. 10A and 10B depict a needle retention feature (712) according to still another embodiment. The needle retention feature (712) includes a plurality of (i.e., four) latching members (112). The latching members (112) are circumferentially separated by a plurality of (i.e., four) longitudinally extending slots (113). The four longitudinally extending slots (113) in the needle retention feature (712) depicted in FIGS. 10A and 10B are narrower than the corresponding longitudinally extending slots (113) in the needle retention feature (712) depicted in FIGS. 9A and 9B. Further, the exterior of the distal end of the needle retention feature (712) depicted in FIGS. 10A and 10B includes four planar surfaces, while the exterior of the distal end of the needle retention feature (712) depicted in FIGS. 9A and 9B includes only curved surfaces. The latching members (112) extend proximally from a rigid ring (115) and pivot about the rigid ring (115) so that each latching member (112) functions as a "living hinge." Each latching member has an arcuate cross-sectional geometry. Together, the latching members (112), the longitudinally extending slots (113), and the rigid ring (115) define a proximally directed funnel-shaped receiving member that guides the 3-D arrowhead shape (84) into the needle retention feature (712).

Exemplary Dual-Chamber Safe Injection System

The needle assembly proximal ends (50), most proximal ends/harpoons (84), and needle retention features (712) described herein can also be used with dual-chamber safe injection systems. Referring to FIGS. 11A-11E, various aspects of an embodiment designed to facilitate injection of multi-part medications are illustrated, wherein two or more medication components are combined to form an injection combination or solution shortly before delivery into the patient. In one embodiment, a liquid diluent (252) may be combined with a substantially non-liquid form (254), such as a powdered form, of a drug agent, such as a freeze-dried or lyophilized drug component, shortly before injection. The embodiment depicted in FIGS. 11A-11E is a dual-chamber configuration, wherein two chambers within the same syringe body (34) are utilized to carry, mix, and inject an injection solution. Examples of such dual-chamber safe injection systems are described in U.S. patent application Ser. No. 14/696,342 and 62/431,382, the contents of which have been incorporated herein by reference.

Referring to FIGS. 11A-11B, a perspective and a longitudinal cross section view of a dual chamber safe injection system are shown, with a conventional off-the-shelf pre-filled syringe body (34) with conventional proximal and distal stopper members (32, 36) disposed therein. The proximal and distal stopper members (32, 36) together with the syringe body (34) define proximal and distal medicine chambers (40, 42). The proximal and distal stopper members (36, 37) occlude the proximal and distal ends of the proximal medicine chamber (40). The distal stopper member (36) occludes a proximal end of the distal medicine chamber (42). A needle coupling assembly (606) is disposed at the distal end of the distal medicine chamber (42) with a needle cover member (63) installed for storage. The dual chamber safe injection system controls transfer of a first medicine component from the proximal medicine chamber (40) to the distal medicine chamber (42) and exit of a mixed/combined medicine from the distal medicine chamber (42) distally subject to sequential insertion of a plunger assembly relative to the syringe body (34) to various degrees by a user. The plunger assembly includes the proximal stopper member (32), a plunger housing member (69) and a plunger manipulation interface (128). The first medicine component located in the proximal medicine chamber (40) may be a liquid such as aqueous or oil based medicine solutions, a gel, or the first medicine component may be a diluent for mixing with the second medicine component in the distal medicine chamber (42). The second medicine component in the distal medicine chamber (42) may be a dry form medicine such as a powder, microspheres, emulsion, lyophilized or freeze dried medicine, or a cake like solid medicine. The second medicine component in the distal medicine chamber (42) may also be a liquid that mixes with the first medicine component from the proximal medicine chamber (40).

The dual chamber safe injection system has a staked needle configuration wherein upon presentation to the user, a needle assembly, comprising a needle coupling assembly (606), a needle distal end/tip (48), a needle joining member (83—see, for example, FIG. 6E), and a needle proximal end (50) are mounted in position ready for injection after removal of a needle cover member (63) which may comprise an elastomeric sealing material on its internal surface to interface with the needle distal end (48) or the distal housing portion (610) during storage. Alternatively, the needle cover member (63) may comprise a vent (not shown) for allowing pressure resulting from the transfer and mixing of the medicine components to escape from inside the syringe body (34) while preventing contamination from entering the syringe body (34). While, the staked needle is depicted as mounted in position, the staked needle may be removably coupled to the syringe body (34) using a Luer interface (not shown), with the proximal end (50) of the needle member extending through the Luer interface and into the distal medicine chamber (42).

In the embodiment depicted in FIGS. 11A-11E, a significant portion of the safe needle retraction hardware resides within a plunger housing (44), similar to the embodiment depicted in FIGS. 6A-6CC and described above. Further, the embodiment depicted in FIGS. 11A-11O can include a proximal needle end (50) and a needle retention feature (712), similar to the embodiments depicted FIGS. 6A-10B, to couple the needle spine assembly (76) to the needle retention feature (712). Moreover, the embodiment depicted in FIGS. 11A-11E can include a needle latch (616) and a necked-down or radially-reduced portion (111) of the needle spine assembly (76), similar to the embodiment depicted FIGS. 6A-6CC, to selectively prevent proximal movement of the needle spine assembly (76) relative to the needle coupling assembly/hub (606).

Returning to FIGS. 11A-11B, for example, a dual chamber safe injection system comprises a conventional syringe body (34), fitted with proximal and distal plunger tips (32, 36) configured to be pierced by proximal needle end (50) at an appropriate time to assist with medication transfer and needle retraction; the proximal plunger tip (32) is coupled to a plunger manipulation interface (128) by a plunger housing member (69) defining an inner volume occupied by various other portions of the assembly, as described below, which are configured to retract the needle at an appropriate time in the sequence of use. A needle coupling assembly (606) described above is included in the illustrated embodiment; other embodiments may comprise Luer type needle assembly coupling to the syringe body (34). The depicted version of the syringe body (34) comprises a small diameter flange (33) coupled to the conventional integral syringe flange (38), which has a geometry that may be manipulated or interfaced between the index and middle fingers of the operator, for example, while a thumb of the operator is interfaced with the plunger manipulation interface (128). FIGS. 11A and 11B illustrate pre-utilization assemblies with a needle cover (63) in place to mechanically isolate the distal needle end (48). The needle cover (63) may be removed and the assembly readied for injection into a patient.

Figure 11C:
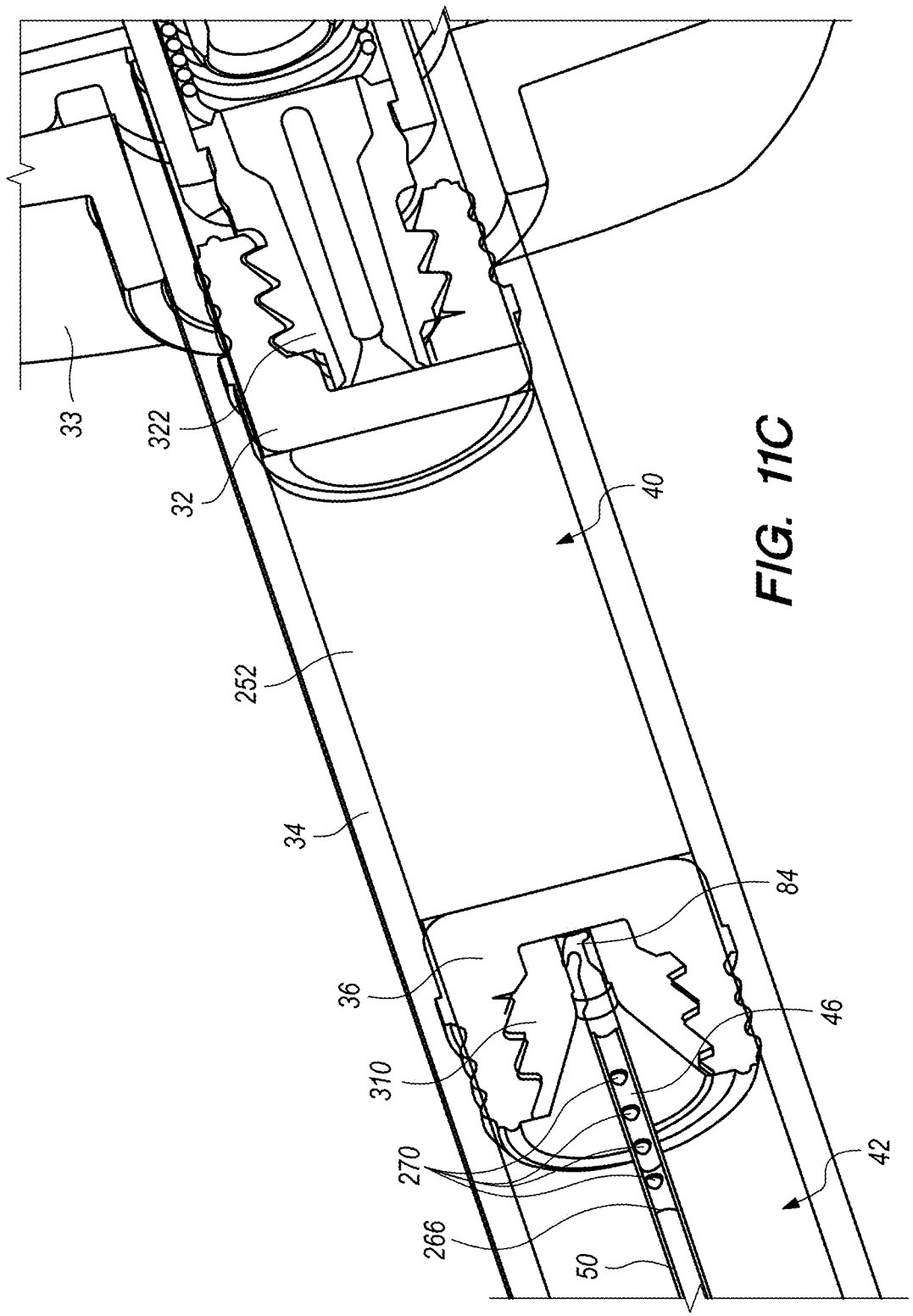
FIGS. 11A-13G illustrate various aspects of dual chamber safe injection systems according to various embodiments.

As shown in FIG. 11C, the proximal and distal stopper members (32, 36), together with the syringe body (34) define a proximal medicine chamber (40) with the dual chamber safe injection system in a transport configuration. In particular, because the distal end of the proximal stopper member (32) and the proximal end of the distal stopper member (36) are each coated with a lubricious polymer coating (e.g., PTFE), the first and second polymer coatings of the proximal and distal stopper members (32, 36), together with the syringe body (34) define the proximal medicine chamber (40). The lubricious polymer coating also serves to isolate the rubber of the proximal and distal stopper members (32, 36) from the medicine and medicine components. The proximal and distal stopper members (32, 36) may be oriented as shown in FIG. 11C or the distal stopper may be flipped so the lubricious coating faces the distal medicine chamber (42) such that the second drug component in the distal medicine chamber (42) contacts the lubricious coating for storage. In the case of the flipped stopper, the needle guide assembly may be held in place by a centering guide disc shown and described in U.S. patent application Ser. No. 62/431,382, the contents of which have been incorporated herein by reference. In an alternative embodiment, the proximal and distal stopper members (32, 36) are rubber without a lubricious polymer coating.

Because the proximal stopper member (32) is coupled to the plunger housing member (69) and the plunger manipulation interface (128), distally directed force applied to the plunger manipulation interface (128) will move the proximal stopper member (32) in a distal direction relative to the syringe body (34). Because the proximal medicine chamber (40) is prefilled with a substantially incompressible liquid and because in the transport configuration depicted in FIG. 11C there is no path for the incompressible liquid to escape the proximal medicine chamber (40), distal movement of the proximal stopper member (32) results in distal movement of the distal stopper member (36).

As shown in FIG. 11D, after the distal stopper member (36) has been moved distally relative to the syringe body (34) to place the dual chamber safe injection system into a transfer configuration, the needle proximal end (50) has pierced the distal stopper member (36) and partially entered the proximal medicine chamber (40). Indeed transfer configuration depicted in FIG. 11D, a transfer pipe (46) portion of the needle proximal end (50) forms a fluid path between the proximal and distal medicine chambers (40, 42). The transfer pipe (46) includes a plurality of proximal openings (270) and a middle opening (266). The transfer pipe (46) is hollow and forms the fluid path between the proximal most proximal opening (270), which is disposed in the proximal medicine chamber (40) and the middle opening (266), which is disposed in the distal medicine chamber (42). While the transfer pipe (46) depicted in FIGS. 11D-11E includes four proximal openings (270) and a middle opening (266), other embodiments may have more or fewer proximal and middle openings. Increasing the number of proximal and middle openings increases the tolerance for positioning of the transfer pipe (46)/needle proximal end (50) relative to the distal stopper member (42) while maintaining an open fluid path between the proximal and distal medicine chambers (40, 42).

After the dual chamber safe injection system is in the transfer configuration as depicted in FIG. 11D, as more force is applied to the plunger manipulation interface (128), the proximal stopper member (32) can move proximally relative to the distal stopper member (36), because liquid in the proximal medicine chamber (40) can move to the distal medicine chamber (42) via the transfer pipe (46). As the liquid in the proximal medicine chamber (40) is transferred to the distal medicine chamber (42), the liquid can mix with the contents of the distal medicine chamber (42). In the embodiment depicted in FIGS. 11A and 11B, the liquid in the proximal medicine chamber (40) in the transport configuration (FIGS. 11A-11C) is a first, liquid component of a medicine. The content of the distal medicine chamber (42) is a second component of the medicine. Transferring the liquid from the proximal medicine chamber (40) to the distal medicine chamber (42) mixes the first and second components to form a ready to inject medicine.

Figure 11E:
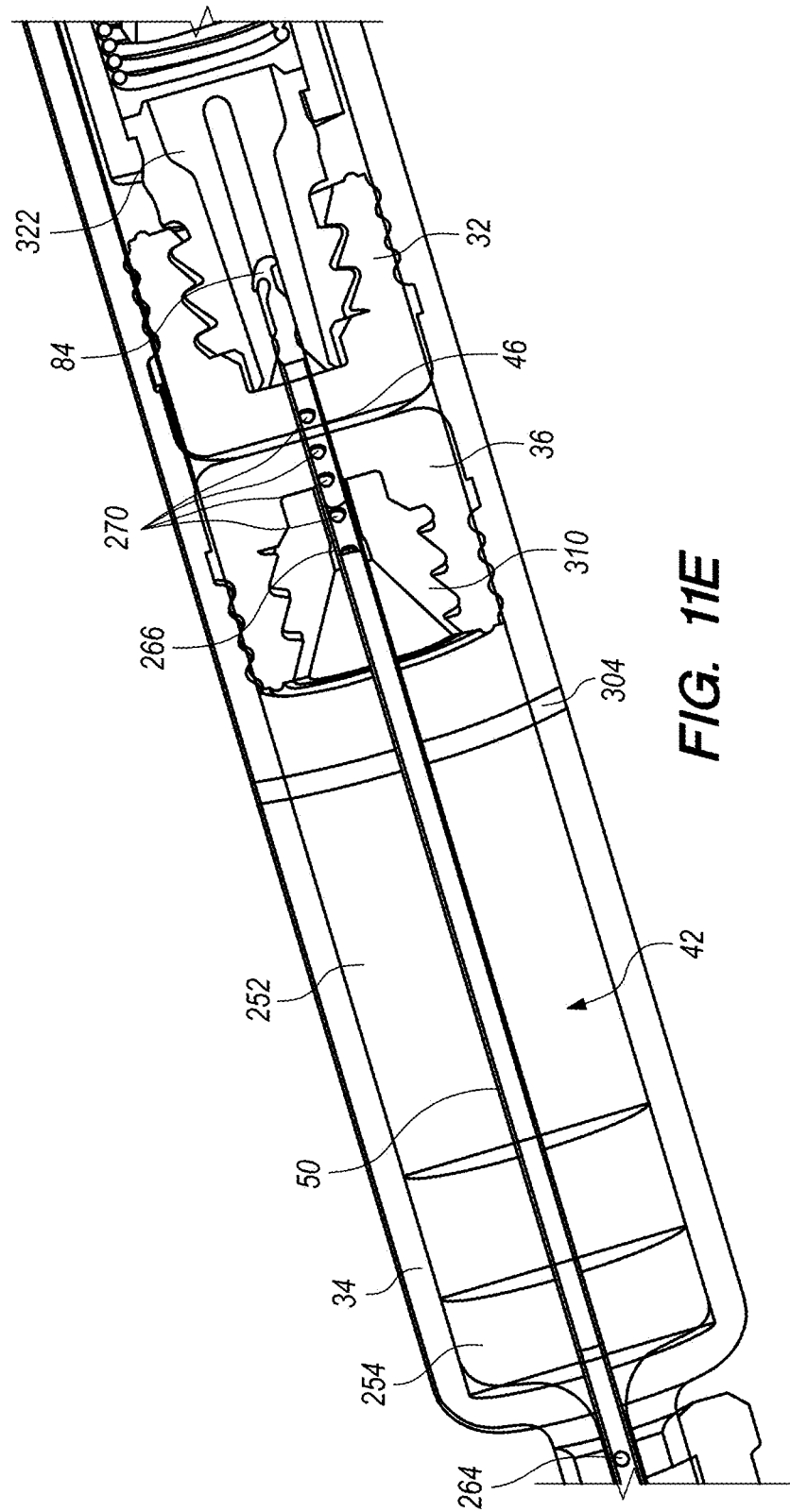
Figure 12C:
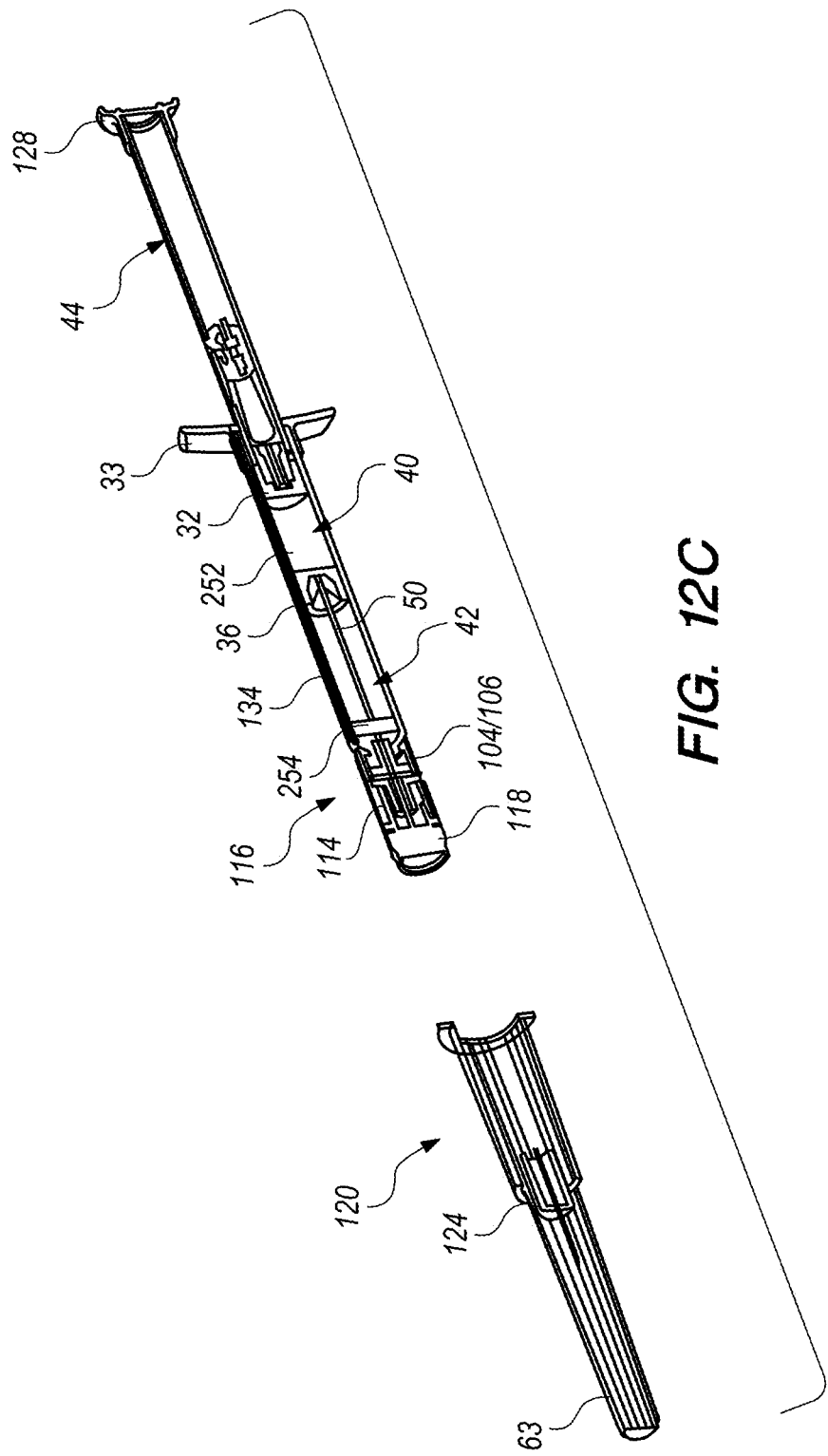
Figure 12D:
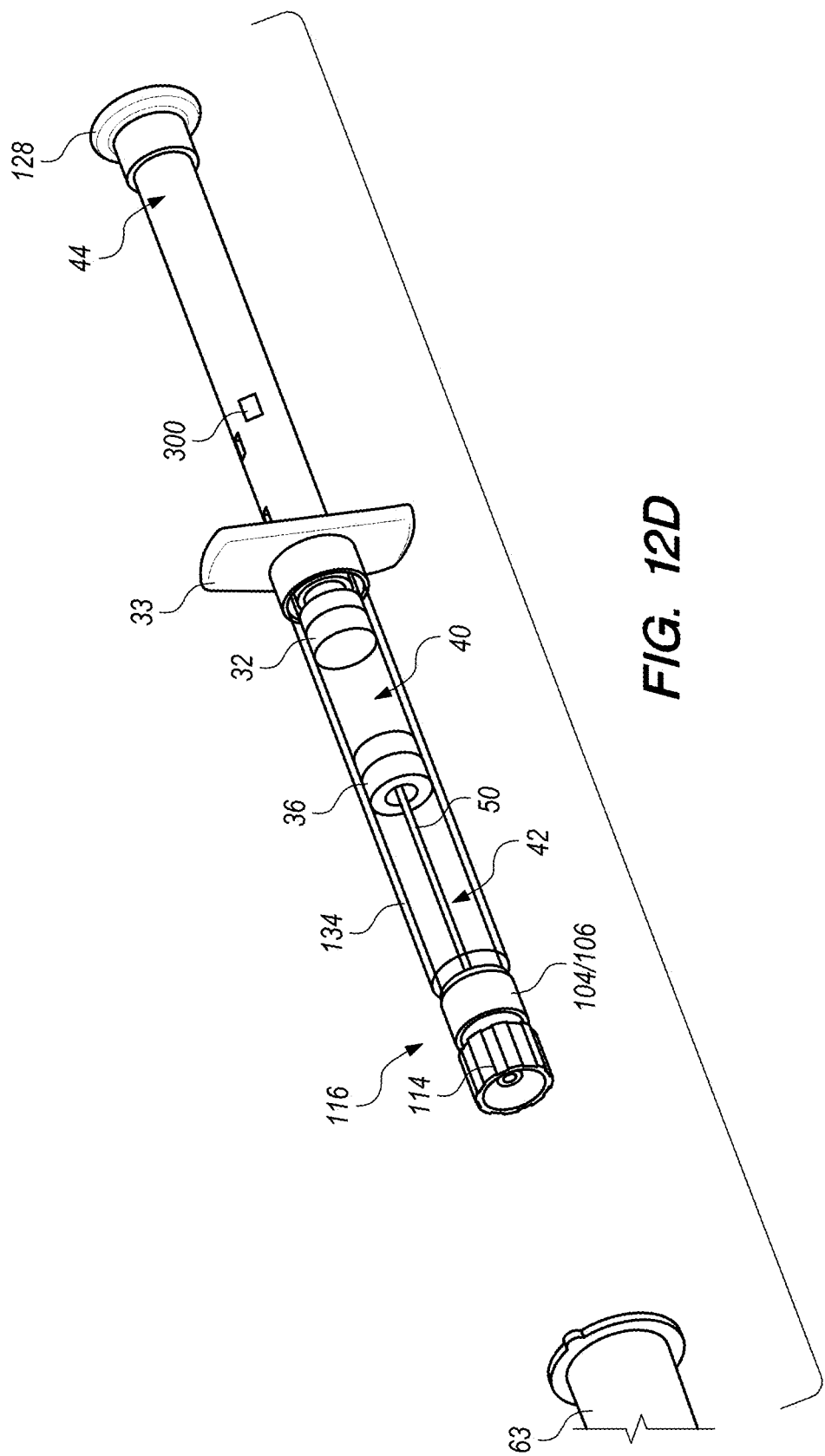
Figure 12J:
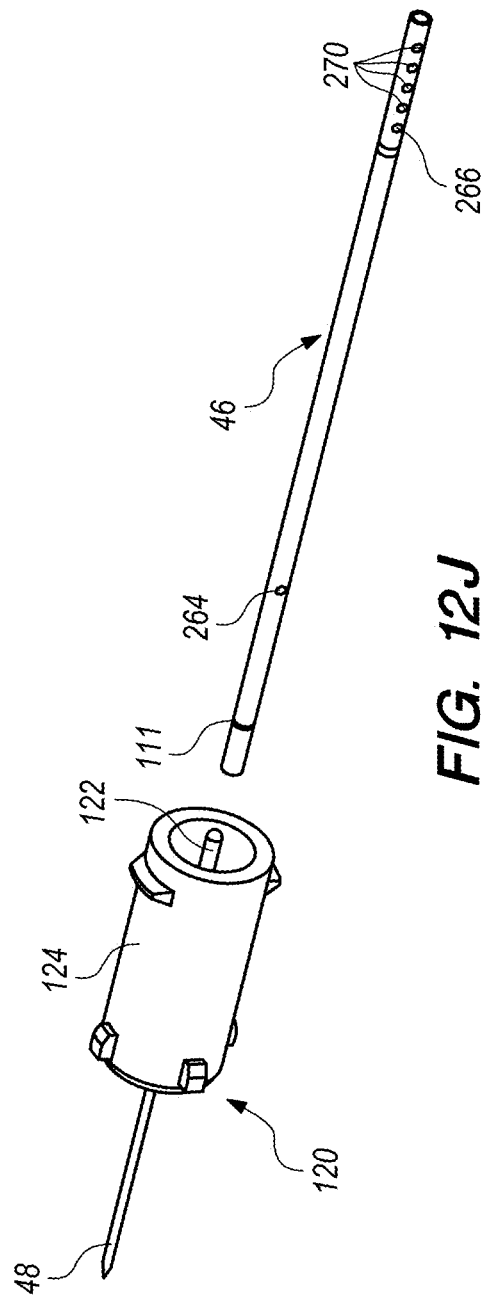
Figure 12K:
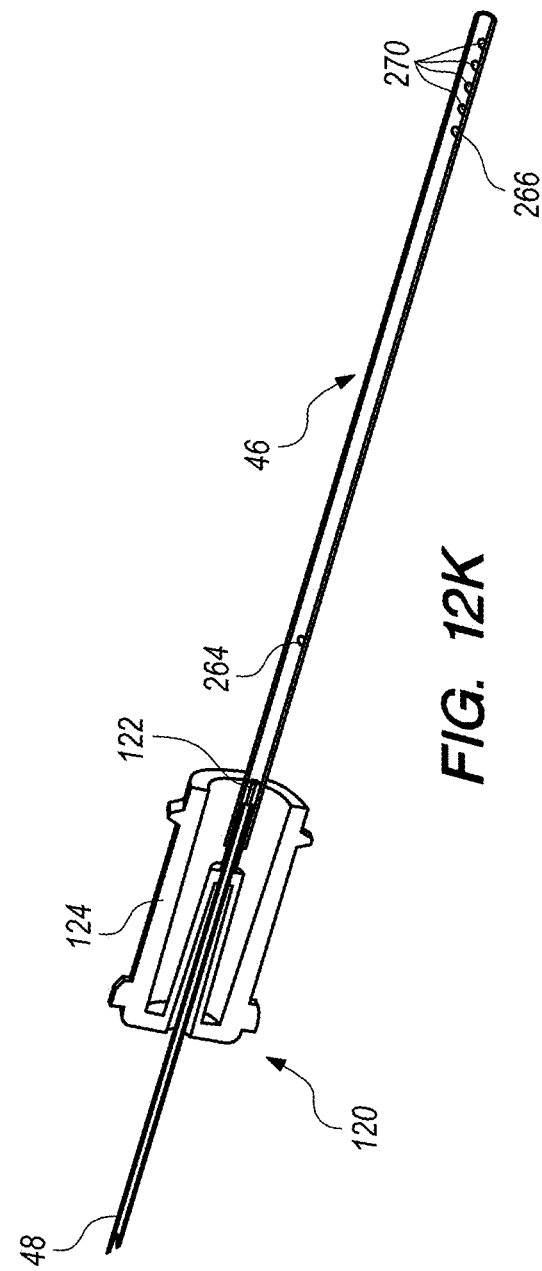
Figure 13A:
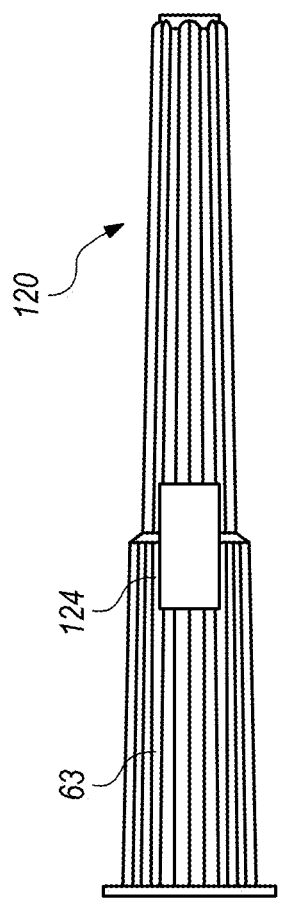
Figure 13B:
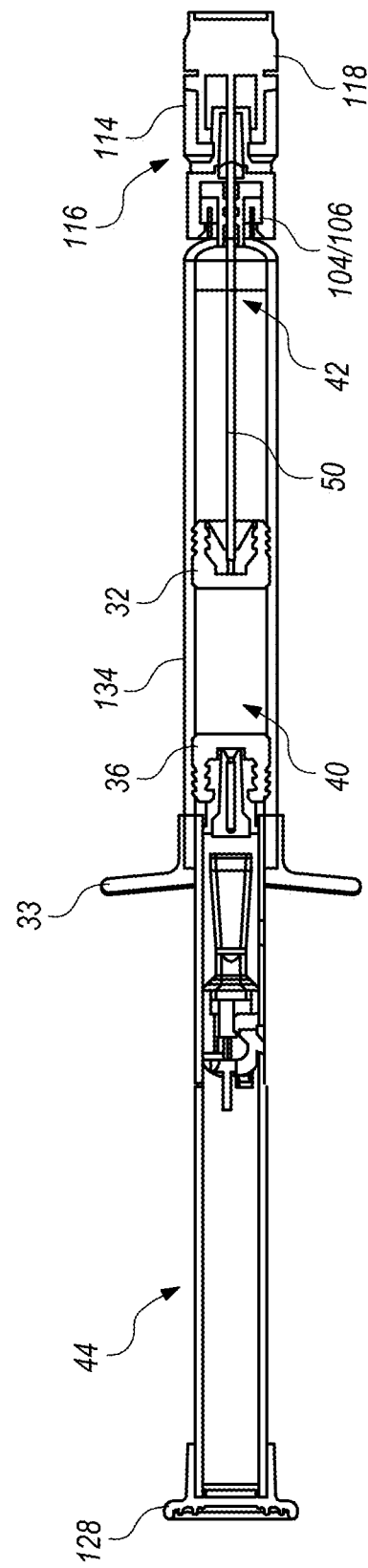
Figure 13C:
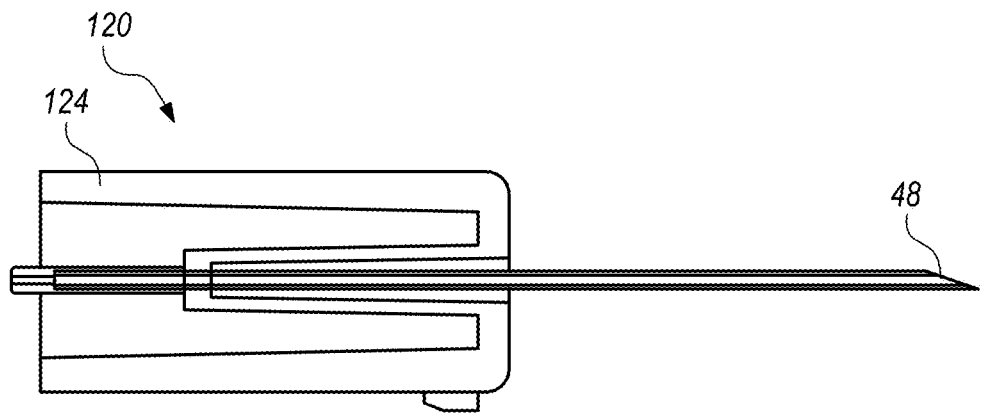
Figure 13D:
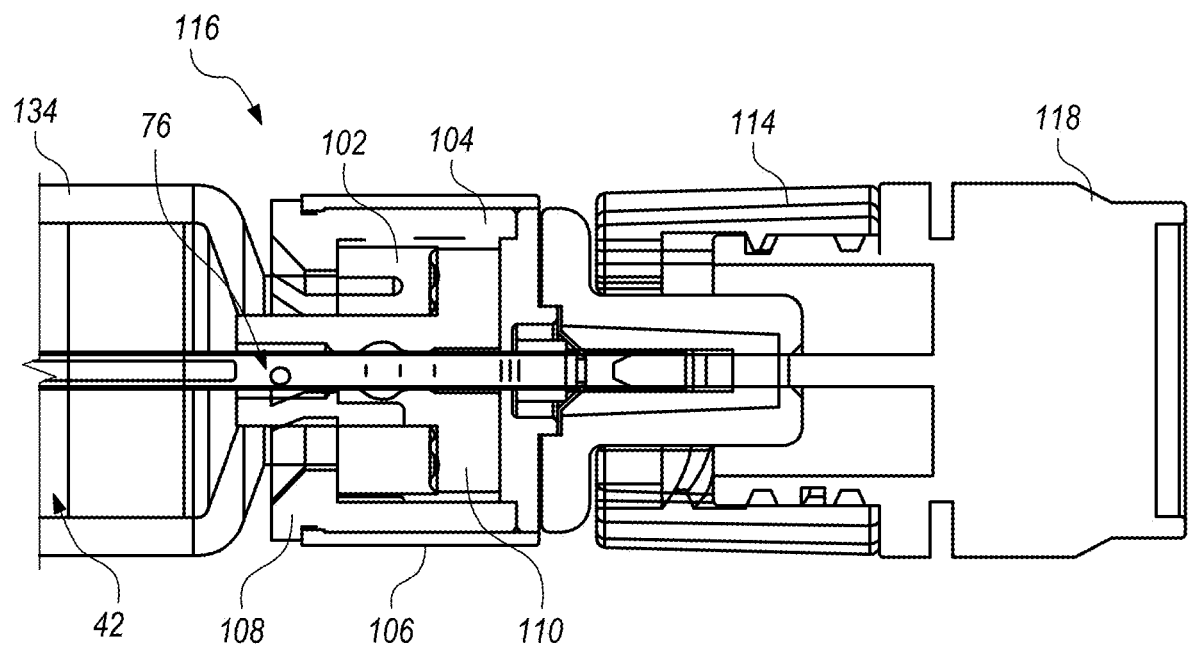
Figure 13E:
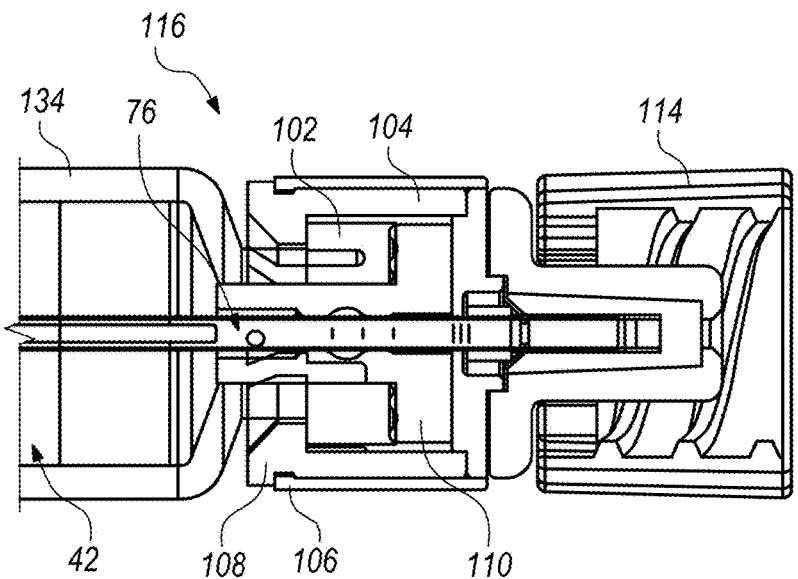
Figure 13F:
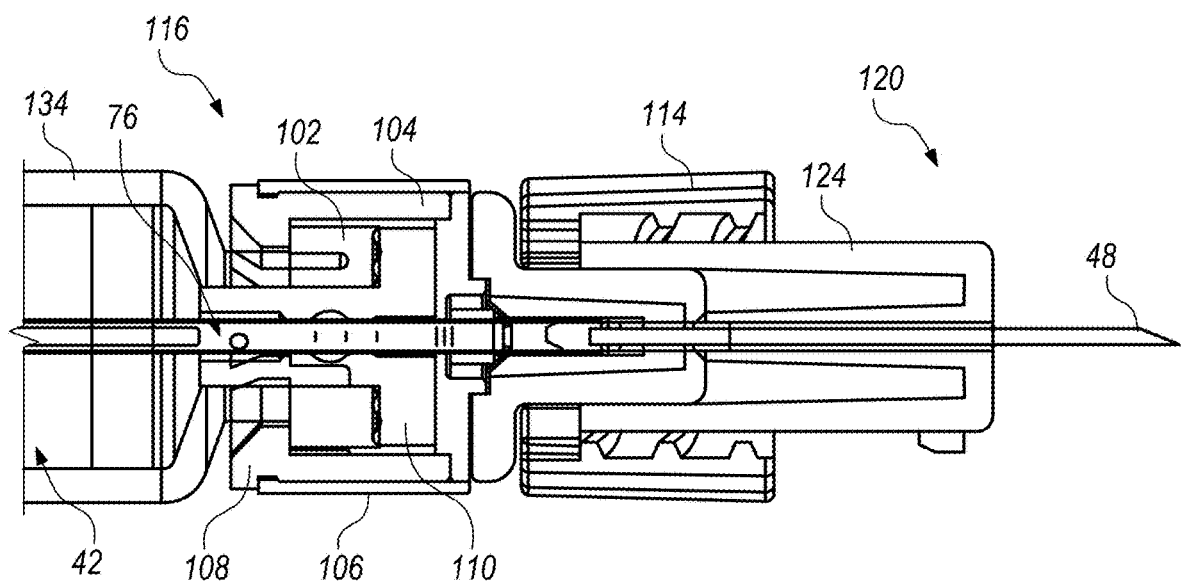
Figure 13G:
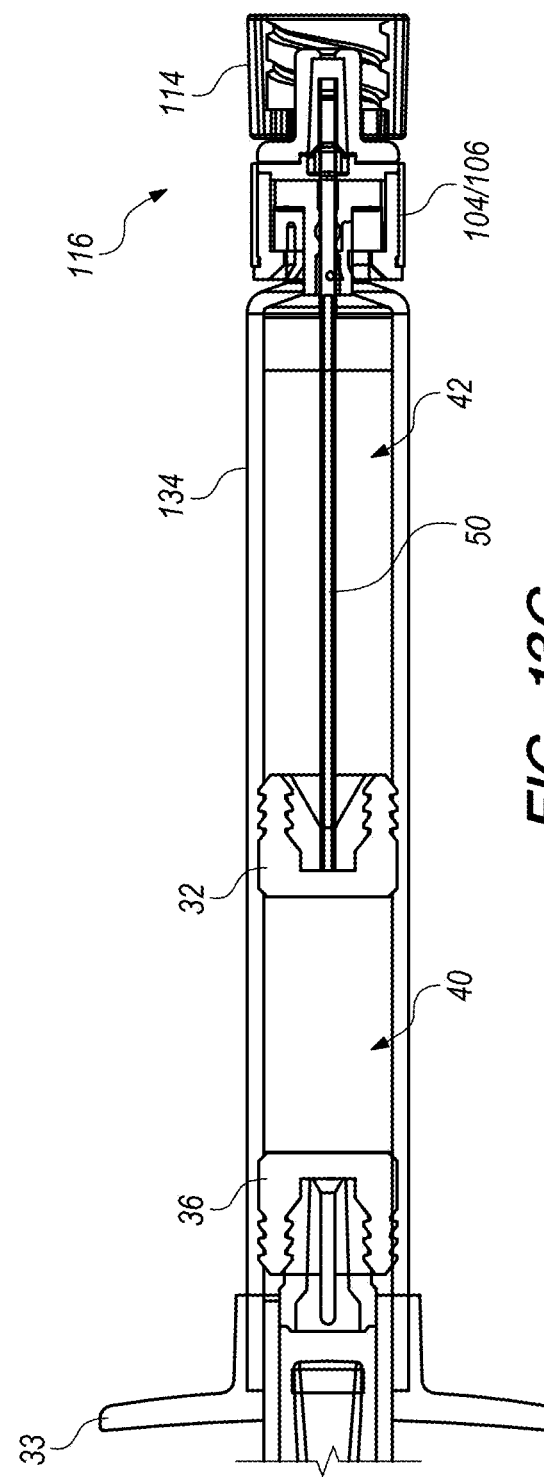

As shown in FIG. 11E, continued force applied to the plunger manipulation interface (128) from the transfer configuration completes the transfer of liquids from the proximal medicine chamber (40) to the distal medicine chamber (42) and places the dual chamber safe injection system into a mixed configuration. In the mix configuration the first and second components are mixed and the medicine is ready to inject into a patient. The mixed medicine is disposed in the distal medicine chamber (42). Distal movement of the proximal stopper member (32) relative to the distal stopper member (36) has placed the proximal and distal stopper members (32, 36) into contact and reduced the volume of the proximal medicine chamber (40) to substantially zero. Accordingly, continued force applied to the plunger manipulation interface (128) moves the proximal and distal stopper members (32, 36) together and ejects the mixed medicine through a distal opening/outflow port at the distal end of the transfer pipe (46) and out of the distal medicine chamber (42) through the needle and into the patient. The transfer pipe (46) also contains a lumen plug (268) disposed between the proximal end and the distal end of the interior lumen. The lumen plug (268) blocks the mixed medicine from being forced retrograde through the flow channels during injection of the mixed medicine into the patient.

Exemplary Dual Chamber Safe Injection Systems with Luer Connectors

FIGS. 12A-13G depict various dual chamber safe injection systems with Luer connectors (114) at their distal ends. For use with a cartridge (134), as described in described in U.S. patent application Ser. No. 62/431,382, the contents of which have been incorporated herein by reference, a female Luer lock connector (114) with internal threads is attached to a collet (104) and a sleeve (106) to form a needle hub (116). The collet (104) and the sleeve (106) can be used to attach the needle hub (116) to the distal end of the cartridge (134) for attaching the needle coupling assembly (606) to the cartridge (134). The distal end of the female Luer lock connector (114) is temporarily sealed with a removable Luer cap (118). Once the needle hub (116) is attached to the cartridge (134), the Luer cap (118) can be removed and a Luer needle (120) may be attached to the needle hub (116) and the dual chamber safe injection system using the female Luer lock connector (114) as shown in FIG. 12E.

After the Luer needle (120) is attached to the needle hub (116) and the dual chamber safe injection system, the system is ready to transport, store, and use (i.e., mixing, injecting and automatic retraction) following steps exactly identical to those depicted for the dual chamber safe injection system with the syringe in FIGS. 11A-11E. Mixing, injection and retraction steps are depicted for a dual chamber safe injection system with a female Luer lock connector (114) in FIGS. 12A-12H.

Using a Luer lock connector (114) and a replaceable Luer needle (120) leads to additional complications. A proximal end (122) of the Luer needle (120) must be connected to a transfer pipe (46) while connecting the Luer needle (120) to the female Luer lock connector (114) on the needle hub (116). During attachment of the Luer needle (120), a needle cover member (63) is configured to guide the Luer needle (120) into the needle hub (116), thereby aligning the proximal end (122) of the Luer needle (120) with the transfer pipe (46) to improve connection between the Luer needle (120) and the transfer pipe (46). Guiding needle cover members are described in U.S. patent application Ser. No. 14/696,342, which was previously incorporated by reference herein. FIGS. 12I-12K and 13C-13F show the connection between the Luer needle (120) and the transfer pipe (46). As seen in these figures, the male Luer lock connector (124) with external threads on the Luer needle (120) guide the proximal end (122) of the Luer needle (120) into the transfer pipe (46) for a secure connection there between. The threads on the Luer lock connectors (114, 124) force the proximal end (122) of the Luer needle (120) into the transfer pipe (46) for a hermetic press fit or snap fit. The distal end of the transfer pipe (46) also includes a latch groove (111) configured to interact with one or more cantilevered latch members (616) to prevent the transfer pipe from being forced proximally into the cartridge (134) during attachment of the Luer needle (120).

Further, using a Luer lock connector (114) and a replaceable Luer needle (120) in a dual chamber safe injection system requires a secure connection/interface between the needle distal tip (48) and the needle joining member (83), as well as the connection/interface that has been formed between the proximal needle end (50) and the needle retention features (712), which is described above. Like the more proximal connection between the proximal needle end (50) and the needle retention features (712), the connection between the needle distal tip (48) and the needle joining member (83) must be secure enough to retract the needle spine assembly (76) through the stopper member/plunger tip (36), without losing "grip" on the needle distal tip (48). The embodiments described herein address this issue using a proximal end connector (212) on the needle distal tip (48) and a distal end receiving member (232) on the needle joining member (83).

Figure 14E:
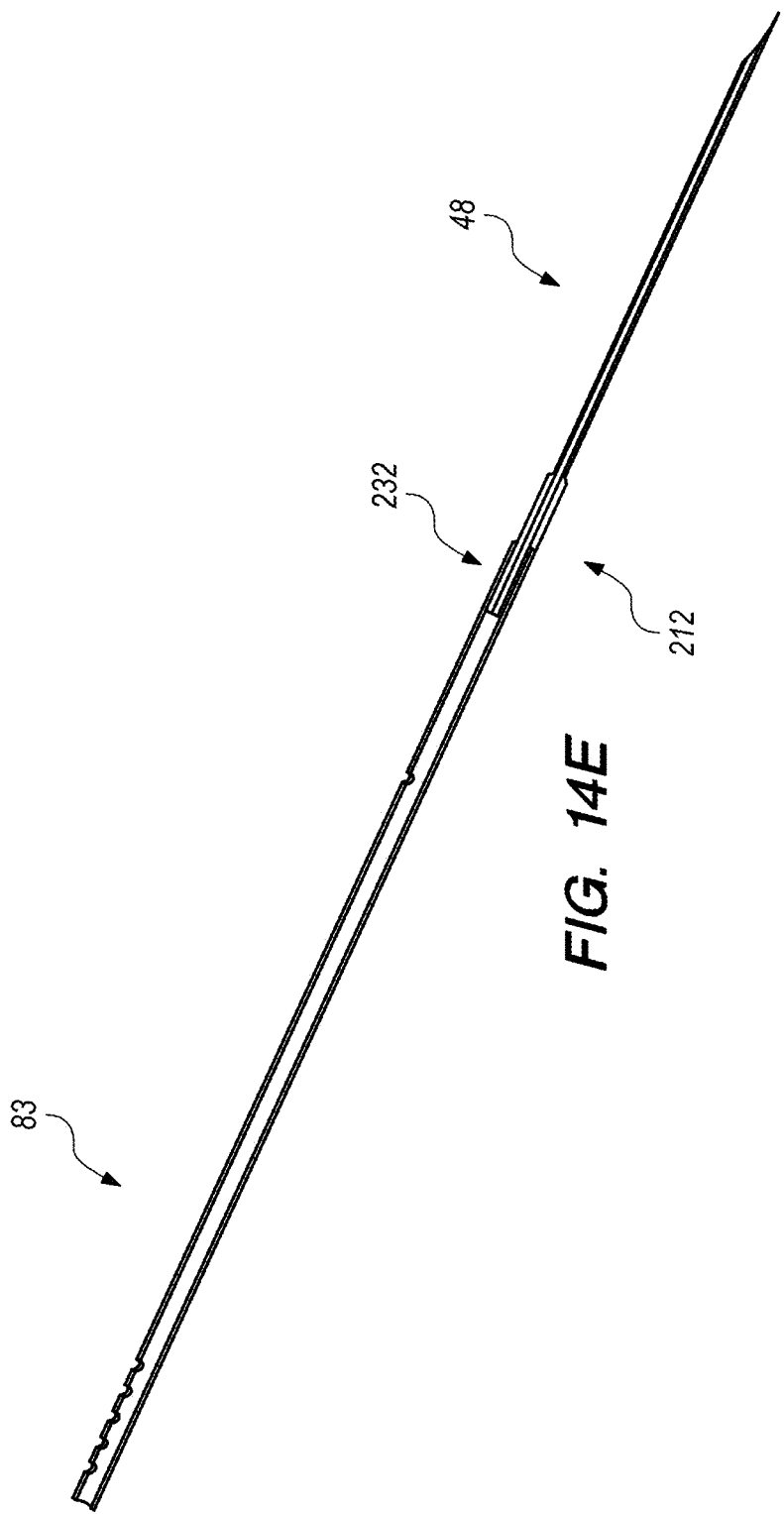
FIGS. 14A-15J illustrate safe injection systems having Luer connectors and distal needle tip connectors according to various embodiments.

As shown in FIGS. 14A and 14B, the needle distal tip (48), e.g., of a replaceable Luer needle, includes a proximal end connector (212). The proximal and connector (212) includes a reduced diameter portion (214), a seal holding portion (216) proximal of the reduced diameter portion (214), and a proximally directed tapering surface (218). As shown in FIGS. 14C-14D and 14G-14H, the distal end receiving member (232) includes a plurality of (i.e., two) latching members (234) circumferentially separated by a plurality of (i.e., two) longitudinally extending slots (236). The latching members (234) of the distal end receiving member (232) include respective proximally directed tapering surfaces (238), which form a proximally directed funnel that facilitates insertion of a proximal end of the proximal end connector (212) into the distal end receiving member (232). Like the needle joining member (83) depicted in FIG. 6E, then needle joining member (83) of the embodiment depicted in FIGS. 12A-13G also include a necked-down or radially-reduced portion (111) that is configured to interface with a latching member (612) to selectively prevent proximal movement of the needle spine assembly (76).

Figure 14H:
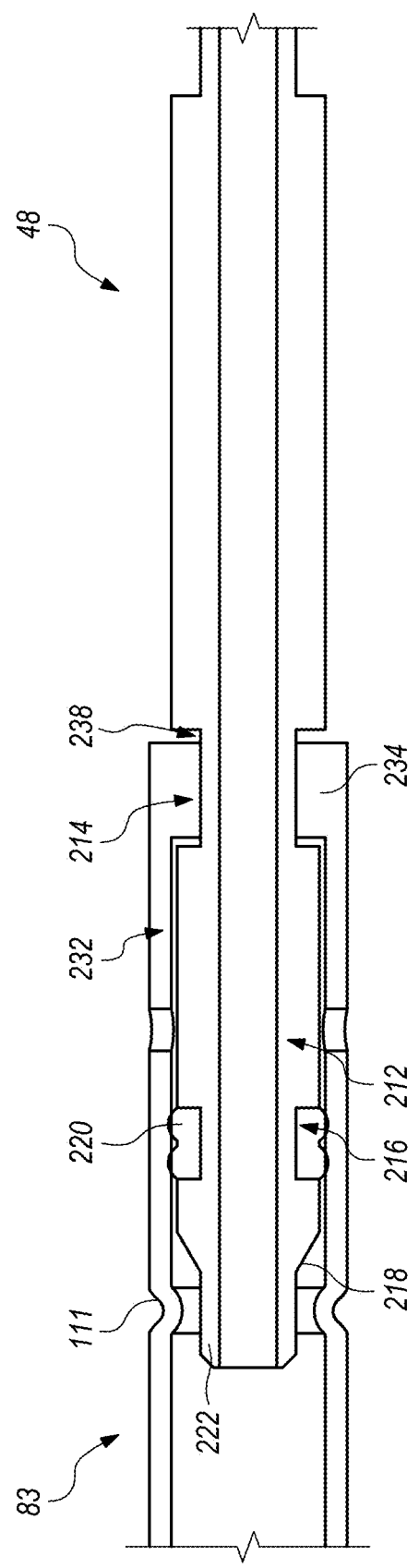
Figure 14I:
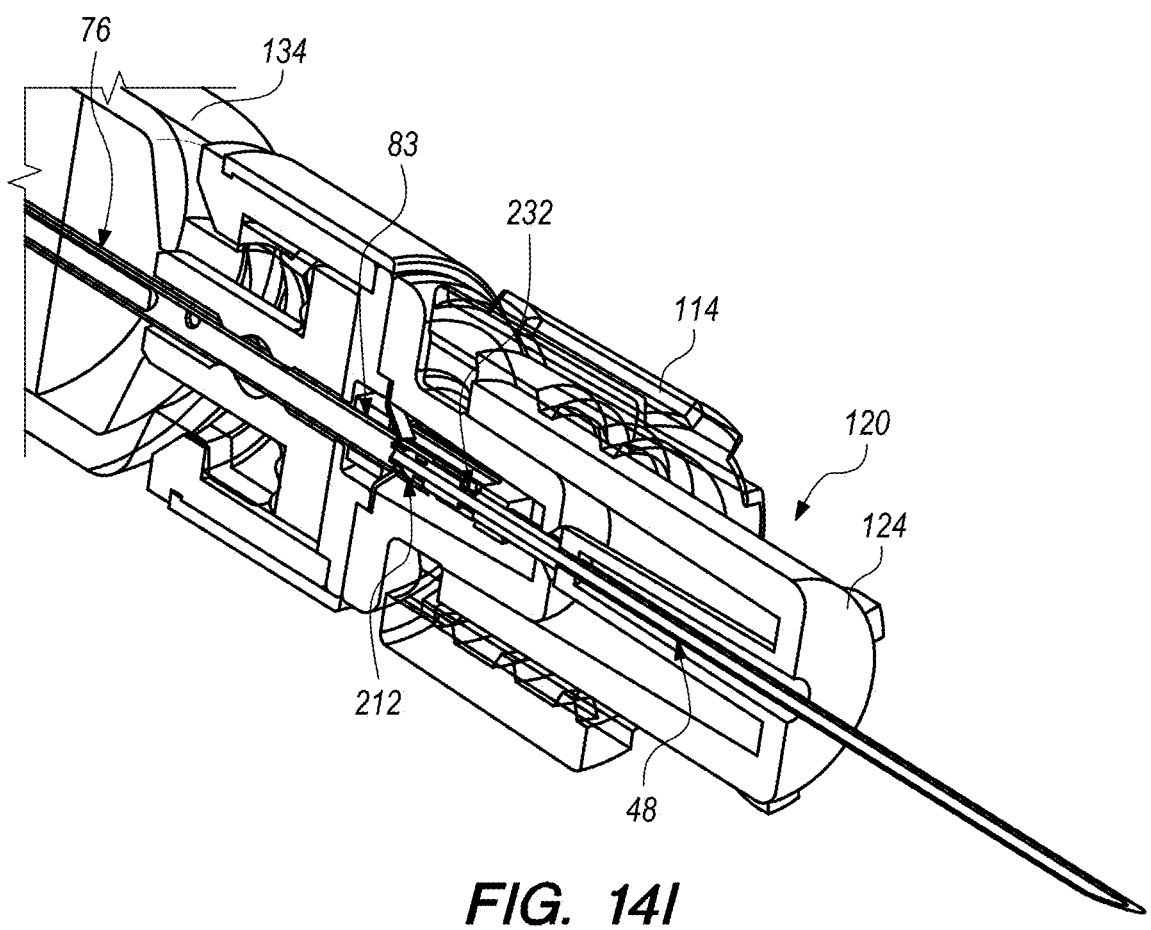
Figure 14K:
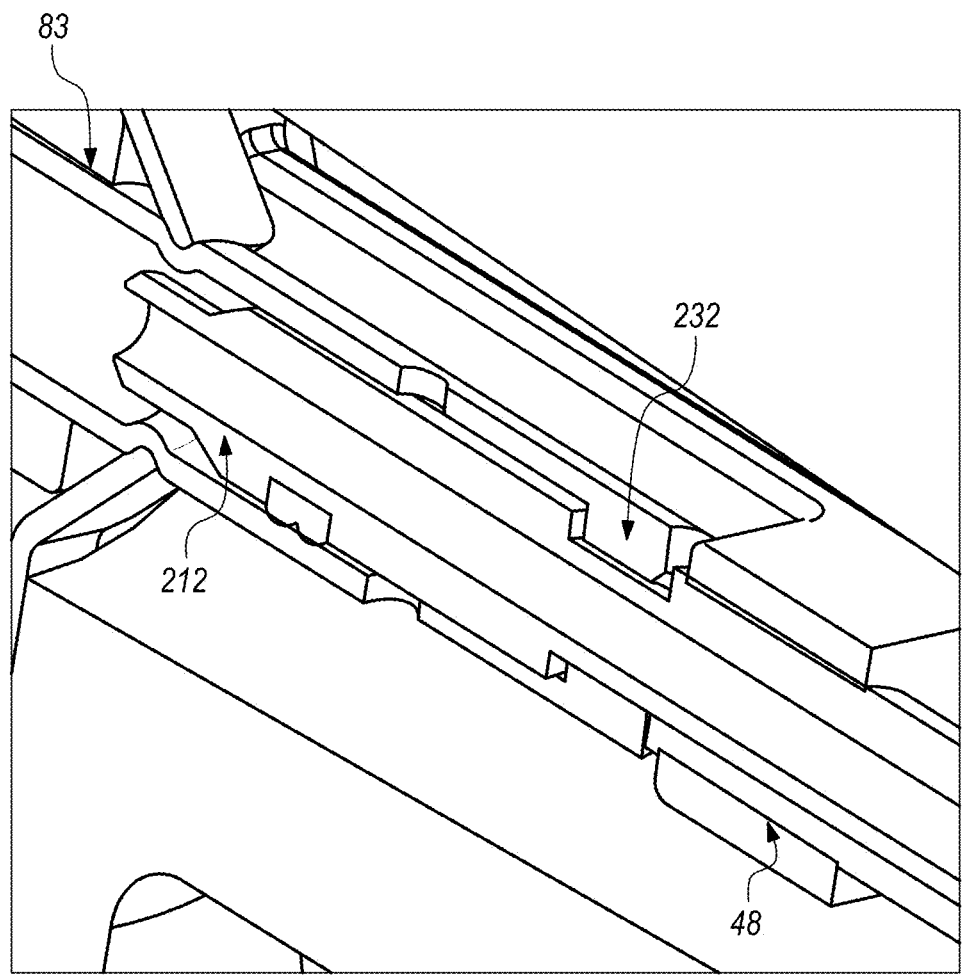
Figure 15A:
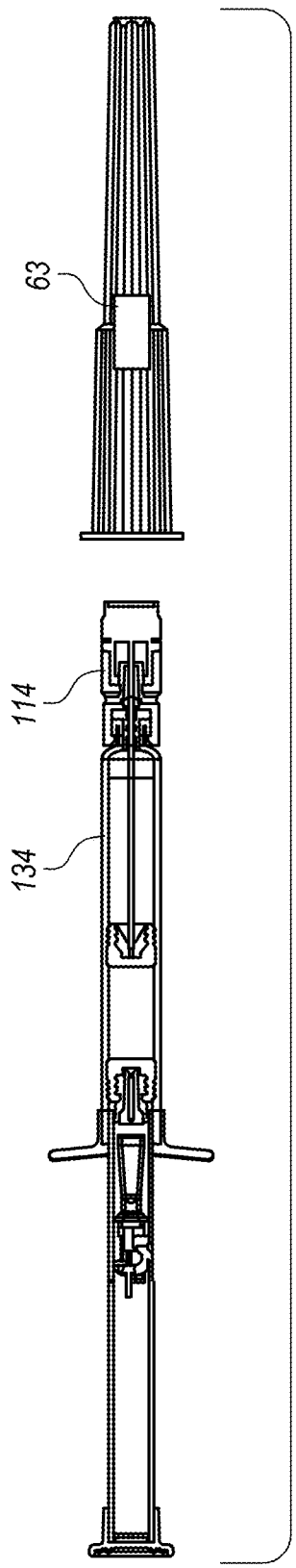
Figure 15B:
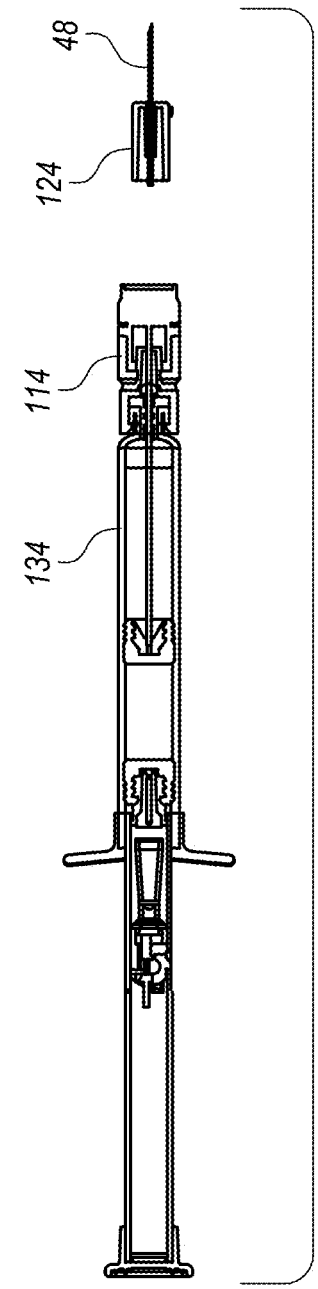
Figure 15C:
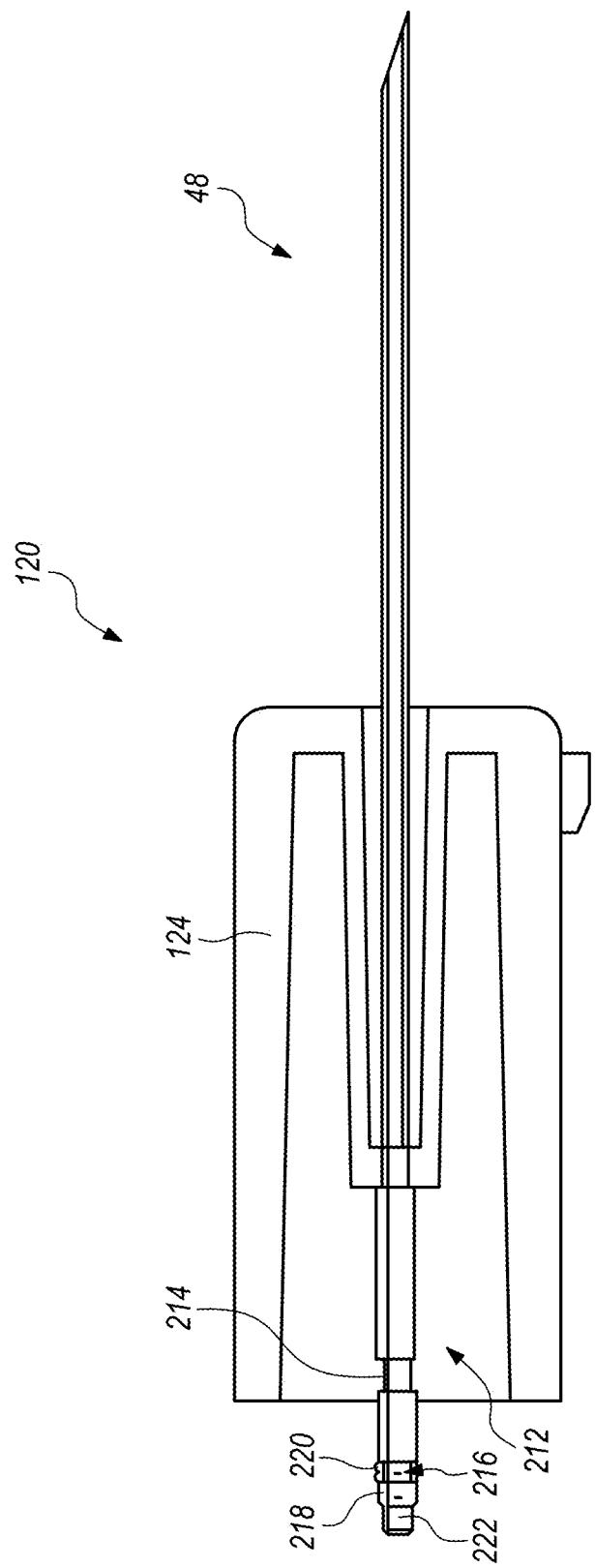
Figure 15D:
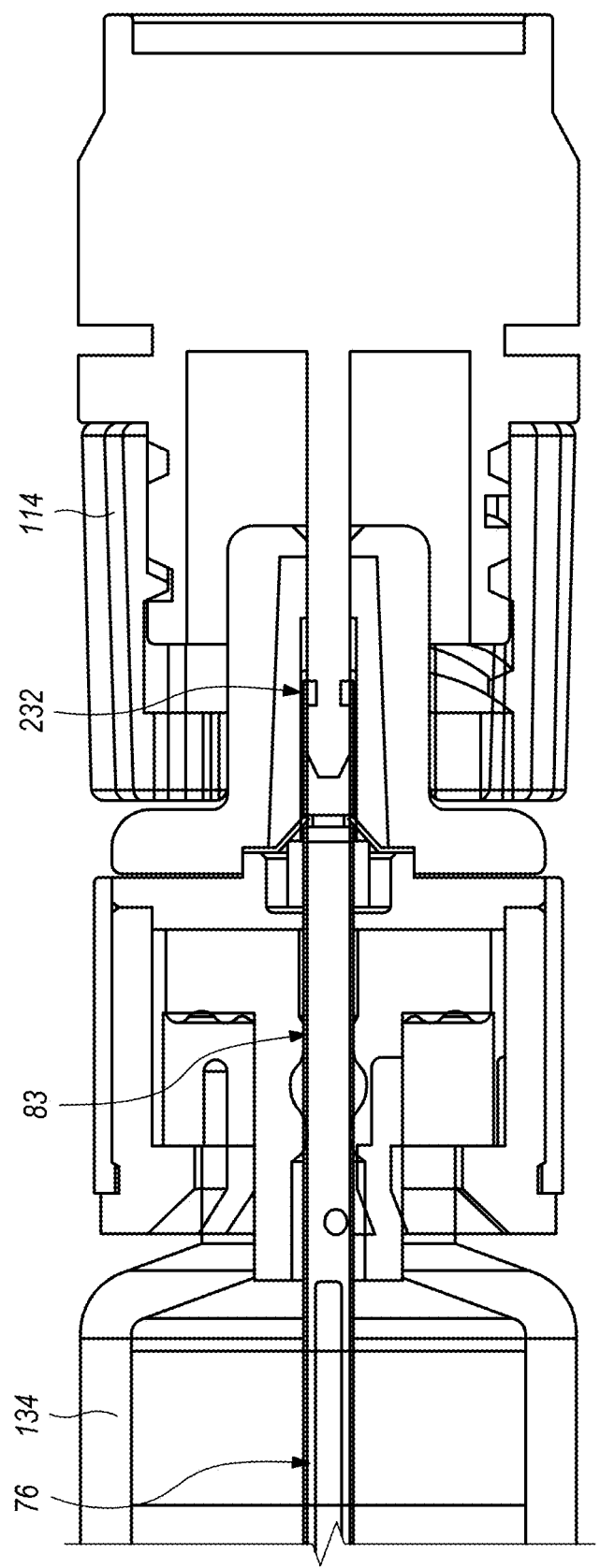
Figure 15E:
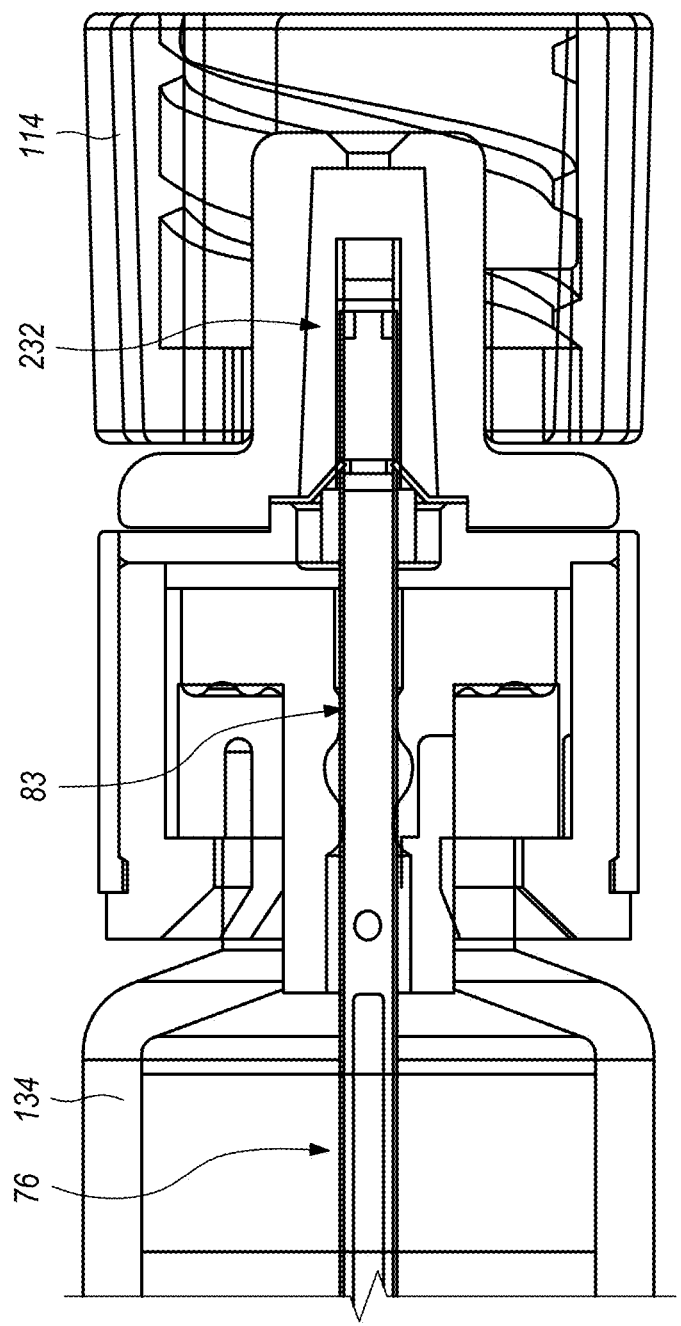
Figure 15F:
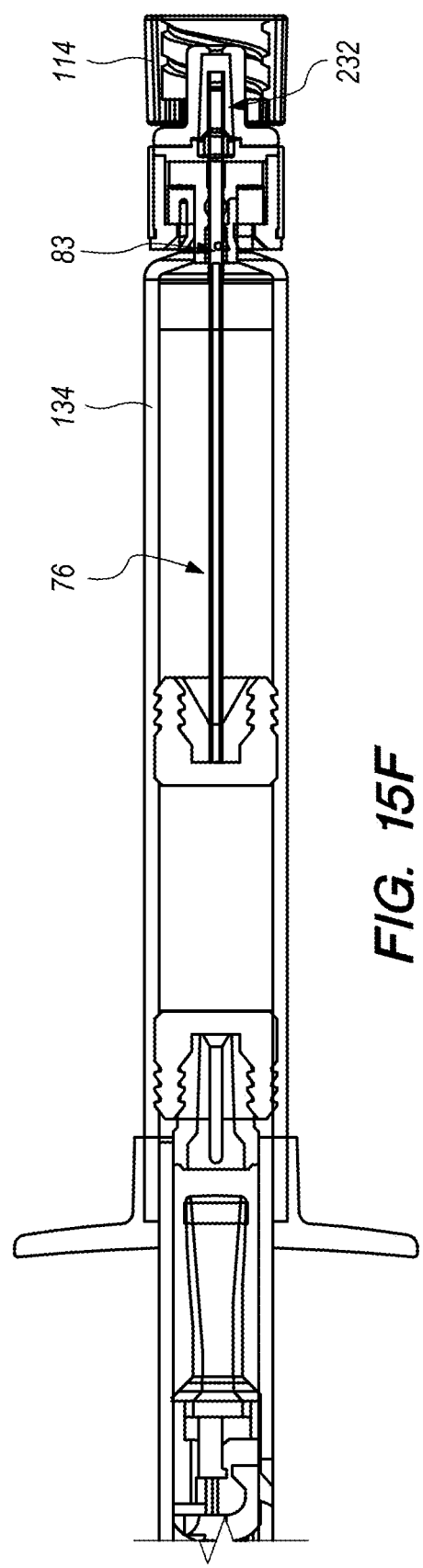
Figure 15G:
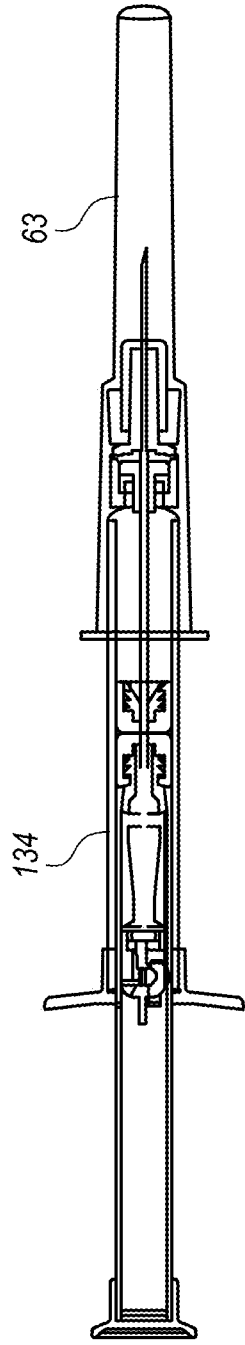
Figure 15H:
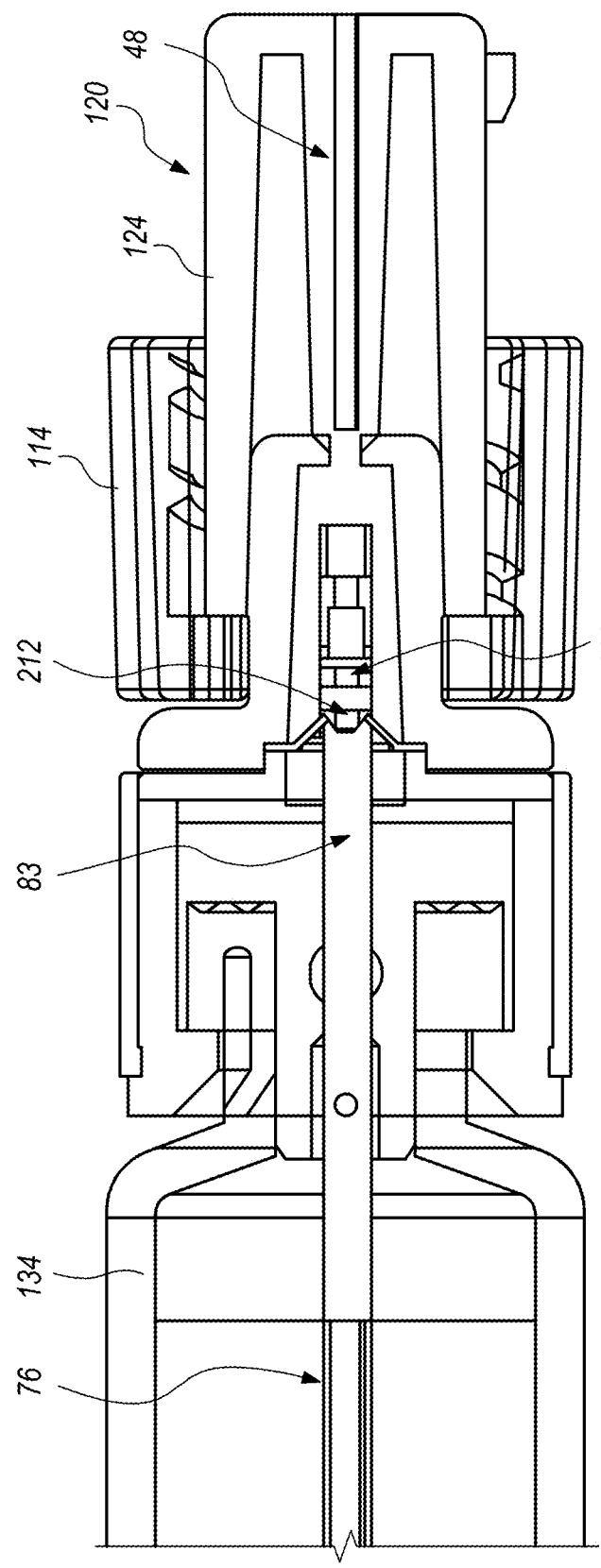
Figure 15I:
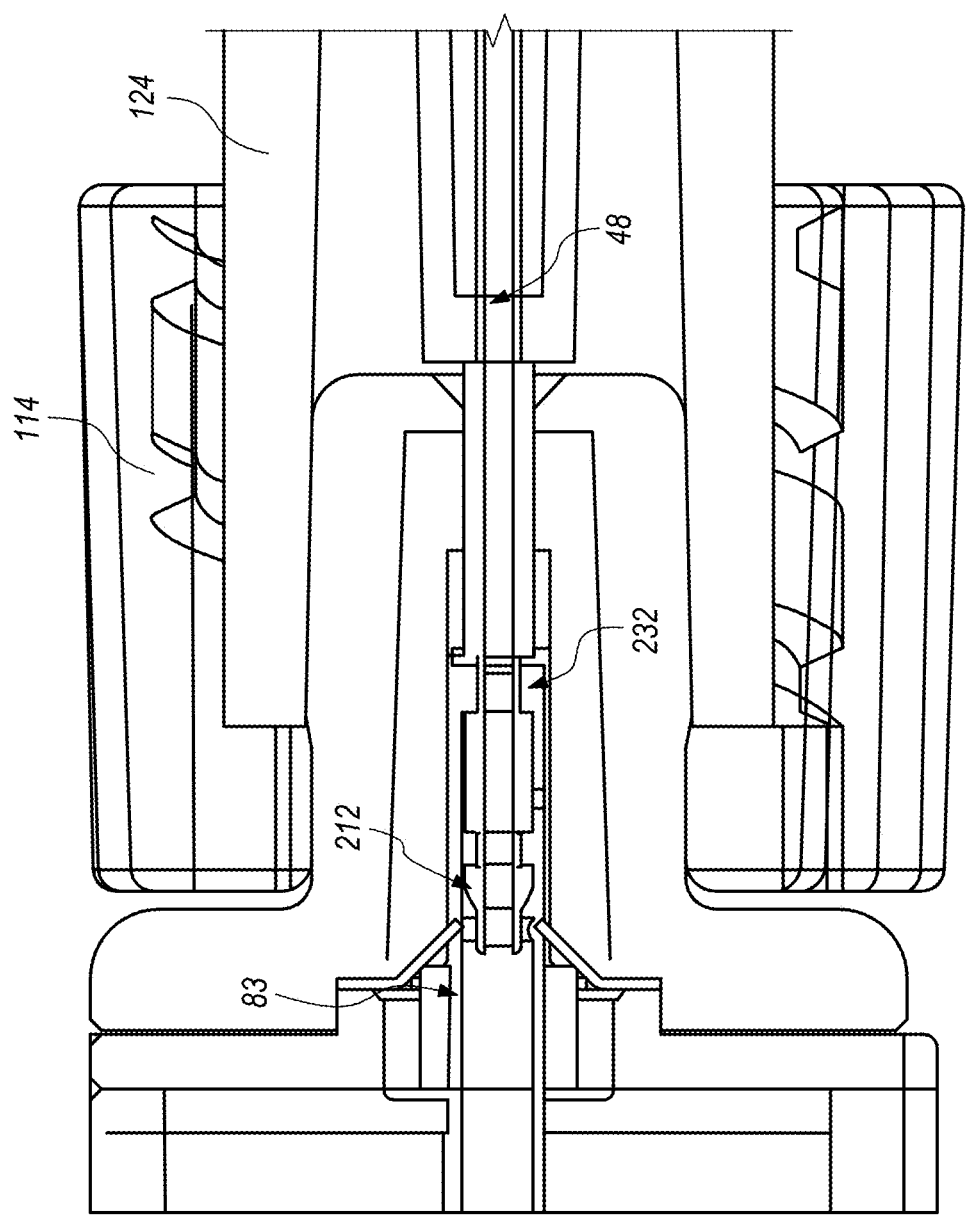

The proximally directed tapering surface (218) of the proximal end connector (212) (of the needle distal tip (48)) forms a partial cone shape that facilitates insertion of the proximal end connector (212) into the distal end receiving member (232), as shown in FIGS. 14D, and 14G-14H. The reduced diameter portion (214) of the proximal end connector (212) facilitates an interaction between the proximal end connector (212) and the distal end receiving member (232) that prevents axial movement of the proximal end connector (212) relative to the distal end receiving member (232). The seal holding portion (216) of the proximal end connector (212) is configured to hold one or more (e.g., two) O-rings (220) to form a fluid tight between an outer surface of the proximal end connector (212) and an inner surface of the distal end receiving member (232), as shown in FIGS. 14C, 14D, and 14H. The fluid tight seal prevents liquid being injected through the needle spine assembly (76) from leaking under pressure through the connection between the needle distal tip (48) and the needle joining member (83).

The distal end receiving member (232) of the needle joining member (83) also includes various parts that facilitate coupling of the proximal end connector (212) and the distal end receiving member (232). As shown in FIGS. 14C-14D and 14G-14H, the distal end receiving member (232) includes a plurality of (i.e., two) latching members (234). The latching members (234) are circumferentially separated by a plurality of (i.e., two) longitudinally extending slots (236). The latching members (234) extend distally from the distal end receiving member (232) of the needle joining member (83). The latching members (234) pivot about their connection to the distal end receiving member (232) of the needle joining member (83) so that each latching member (112) functions as a "living hinge." Each latching member has an arcuate cross-sectional geometry (see FIGS. 14C and 14D).

FIGS. 14C to 14D show the proximal end connector (212) on the needle distal tip (48) before and after coupling to the distal end receiving member (232) on the needle joining member (83). As shown in FIG. 14C, a proximal tip (222) of the proximal end connector (212) is sized to fit through a central opening (238) defined by the latching members (234) in the distal end receiving member (232). As a proximal portion (i.e., from the proximal tip (222) to the reduced diameter portion (214)) of the proximal end connector (212) moves proximally through the central opening (238) and into the distal end receiving member (232), the tapering surface (218) moves the plurality of latching members (234) away from each other and enlarges the central opening (238) so that the proximal portion the proximal end connector (212) can pass therethrough. During the transformation into this "open configuration" of the distal end receiving member (232), the plurality of latching members (234) pivot about their connection to the distal end receiving member (232) of the needle joining member (83) to enlarge the central opening (238). After the portion of proximal end connector (212) has passed through the central opening (238) and into the distal end receiving member (232), the resilience of the latching members (234) moves the latching members (234) toward each, reducing the size of the central opening (238) and moving respective distal portions of the latching members (234) into the reduced diameter portion (214) such that the proximal end connector (212) cannot move axially relative to the distal end receiving member (232). In this "resting configuration" of the distal end receiving member (232), the distal portions of the latching members (234) interfere with interior surfaces of the reduced diameter portion (214) to prevent axial movement of the proximal end connector (212) relative to the distal end receiving member (232), as shown in FIGS. 14D, 14G, and 14H.

The latching members (234) can be made of an elastically deformable material (e.g., a metal or a polymer) such that the central opening (238) defined by the latching members (234) in the distal end receiving member (232) can be enlarged to allow the portion of proximal end connector (212) to pass therethrough in a proximal direction. The living hinges of the latching members (234) may be configured to be operated by elastic deformation. For example, the latching members (234) may elastically deform upon insertion of the portion of the proximal end connector (212) to allow for penetration. The force transmitted by the relative movement of the proximally directed tapering surfaces (238) of the latching members (234) and proximally directed tapering surface (218) of the proximal end connector (212) generates a moment about the connection of the latching members (234) to the distal end receiving member (232) of the needle joining member (83). This generated moment elastically deforms the latching members (234) from the resting configuration to the open configuration. After insertion of the portion of the proximal end connector (212), the latching members (234) are configured to return (because of the elastic deformation) to the resting configuration to resist axial movement of the needle distal tip (48) relative to the needle joining member (83) at a force sufficiently high to allow for needle retraction of the needle spine assembly (76), including the needle distal tip (48) through the stopper (36) and into the plunger housing member (67).

The respective three-dimensional shapes of the proximal end connector (212) and the latching members (234) conform to each other such that their interaction couples proximal end connector (212) and the distal end receiving member (232), and prevents distal movement of the needle distal tip (48) and the needle joining member (83). The three-dimensional shapes form a more secure connection while minimizing slippage of the distal movement of the needle distal tip (48) relative to the needle joining member (83). As shown in FIGS. 14G-14H, the proximal ends of the respective latching members (234) engages the reduced diameter portion (214) of the proximal end connector (212) in their resting configuration, thereby coupling the distal end receiving member (232) and the proximal end connector (212) with respect to axial movement along the longitudinal axis of the needle spine assembly (76) by an interference fit. The conversion of the latching members 63 (234) between the open configuration and the resting configuration allows the proximal end connector (212) and the corresponding distal end receiving member (232) to withstand the retraction force required for operation of the safe injection system.

FIGS. 14I to 15J depict the proximal end connector (212) and the distal end receiving member (232) in an injection system including a replaceable Luer needle (120). The injection system depicted in FIGS. 14I to 15J is also a dual chamber injection system. The distal needle tip connectors described above are particularly suited for dual stopper dual chamber injection systems like those depicted herein, because the needle distal tip (48) may be pulled through a plurality of stopper members (32, 36) in such systems. As used in this embodiment, the proximal end connector (212) and the distal end receiving member (232) allow a reusable Luer needle (120) to be connected to a syringe and/or cartridge having a corresponding Luer connector as described above, while forming a sufficiently secure connection between the needle distal tip (48) and the needle joining member (83) to allow the safe injection system to withdraw the needle spine assembly (76), including the needle distal tip (48), at least partially into the plunger after injection. The outside diameter of the needle spine assembly (76) is configured to be generally streamlined, smooth, and/or of a constant diameter so as to provide minimal resistance to the retraction of the needle distal tip (48) into the plunger after injection. Such a system is especially useful in dual chamber safe injection systems including Luer connectors, as described above.

Hollow Three-Dimensional Arrowhead Needle Assembly Proximal End

Figure 17:
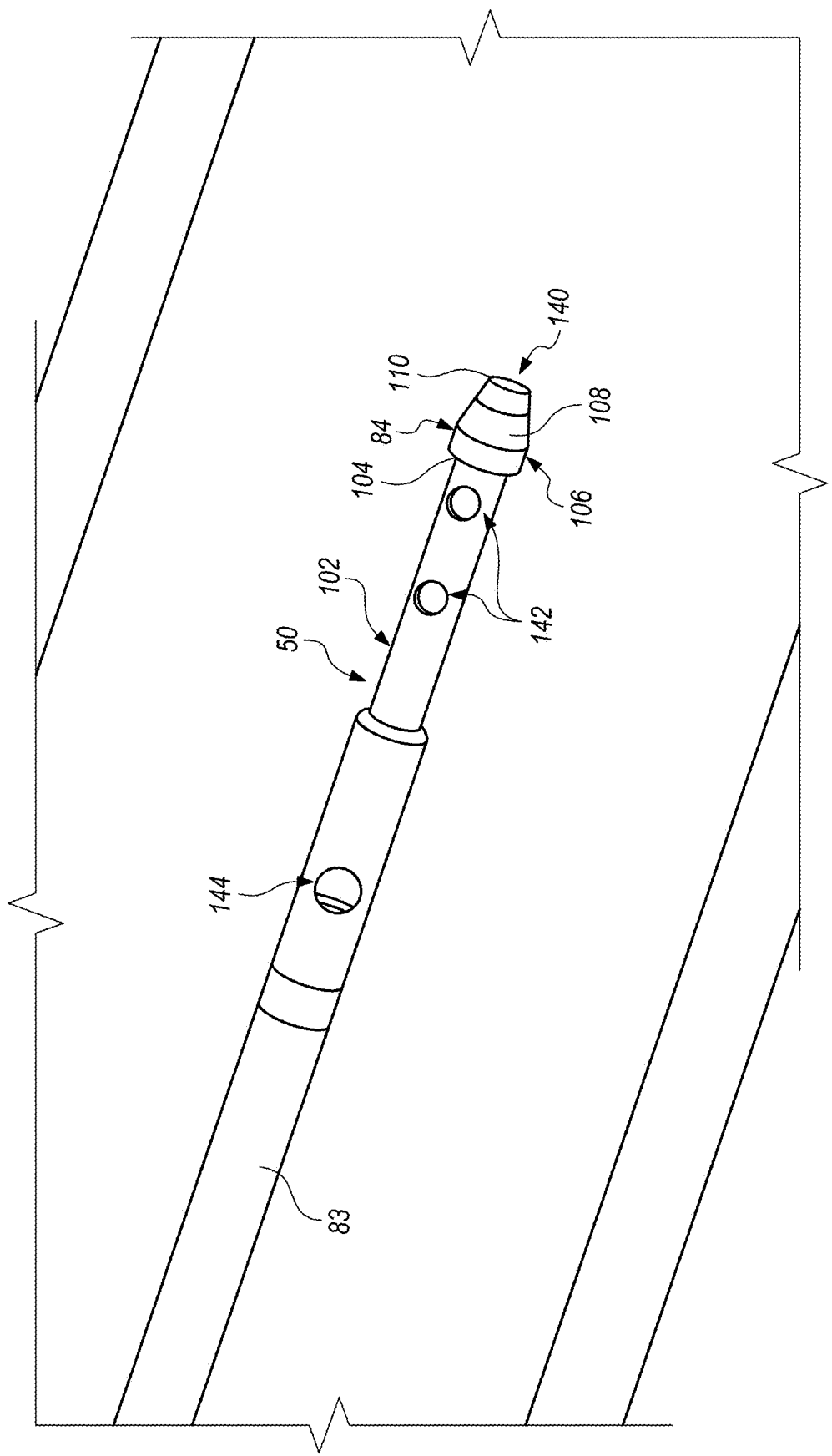
FIGS. 17-21 illustrate hollow 3-D arrowhead assembly proximal ends according to various embodiments.

FIGS. 17-21 depict needle assembly proximal ends (50) according two other embodiments. As shown in FIGS. 17 (perspective view) and 18-21 (longitudinal cross-sectional views), the most proximal end (84) of a first needle assembly proximal end (50) forms a hollow 3-D arrowhead shape (84), with a shape similar to the solid 3-D arrowhead shape (84) depicted in FIGS. 8A-8C. The hollow 3-D arrowhead shape (84) extends proximally from an elongate needle proximal portion (102) of the needle assembly proximal end (50). The hollow 3-D arrowhead shape (84) has an annular distally facing surface (104), a substantially constant diameter surface (106), and a proximally directed tapering surface (108). The proximally directed tapering surface (108) defines a proximally pointed cut-off cone that ends in a proximal tip (110).

The elongate needle proximal portion (102) has a substantially constant first cross-sectional diameter that abruptly expands to a greater second cross-sectional diameter at the annular distally facing surface (104). The substantially constant diameter surface (106) extends proximally from the annular distally facing surface (104), and has the second cross-sectional diameter. The proximally directed tapering surface (108) extends proximally from the substantially constant diameter surface (106), and tapers down from the second cross-sectional diameter. The proximally directed tapering surface (108) tapers down to the proximal tip (110), which has a third cross-sectional diameter that is less than the first and second cross-sectional diameters. While the hollow 3-D arrowhead shapes (84) depicted in FIGS. 17-21 includes a substantially constant diameter surface (106), this feature is optional and other embodiments may transition directly from the annular distally facing surface (104) to the proximally directed tapering surface (108). The annular distally facing surface (104) is shown encompassing a full 360 degrees around the 3-D arrowhead shape (84). In alternative embodiments, the annular distally facing surface may be an interrupted surface (e.g., not encompass a full 360 degrees).

Figure 20:
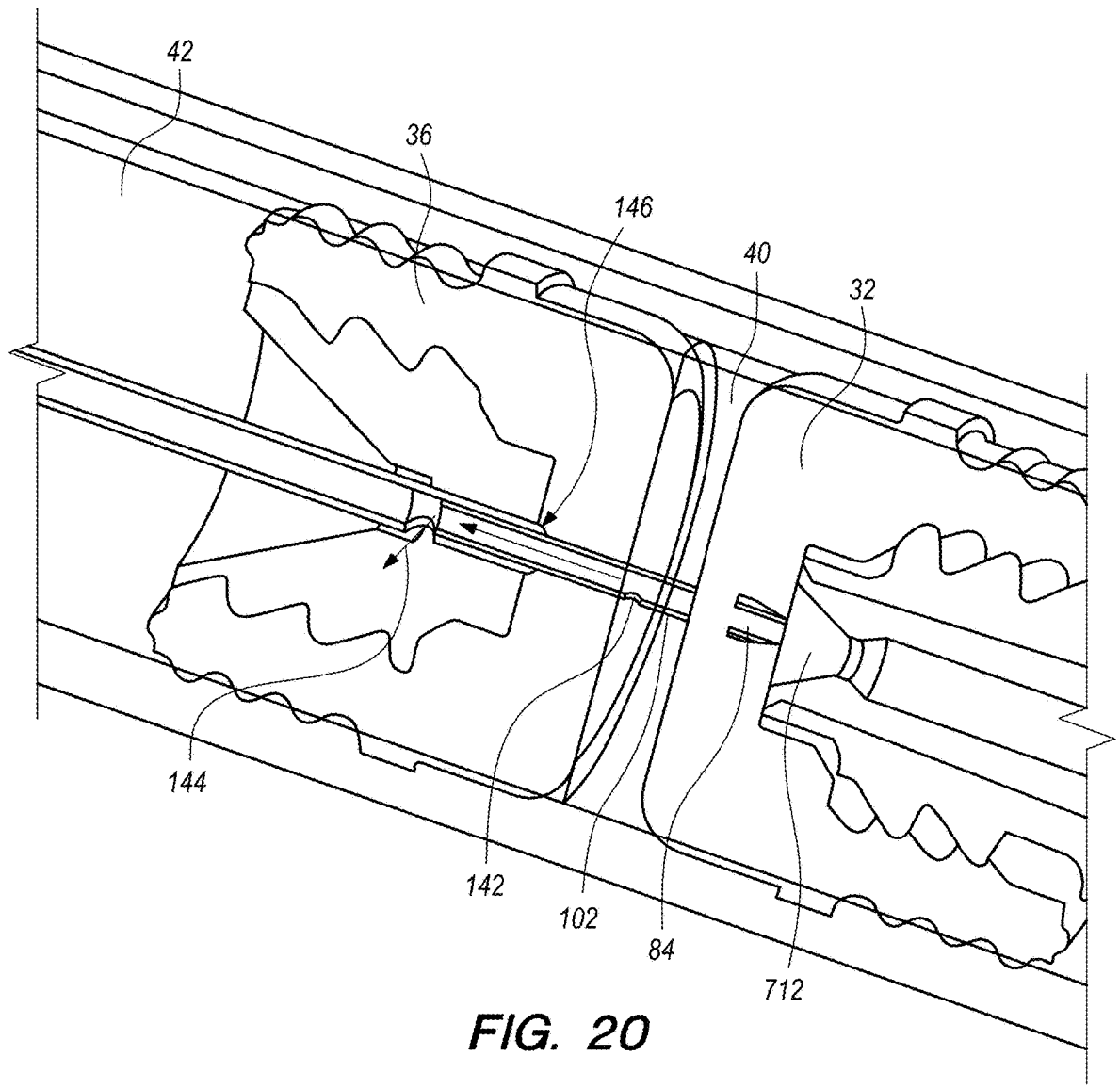

The cut-off cone shape of the hollow 3-D arrowhead shape (84) facilitates insertion of the hollow 3-D arrowhead shape (84) into the needle retention feature (712, see FIG. 20). See FIGS. 8D to 8I and the corresponding description for a similar 3-D arrowhead shape embodiment. The annular distally facing surface (104) facilitates an interaction between the hollow 3-D arrowhead shape (84) and the needle retention feature (712) that prevents distal movement of the hollow 3-D arrowhead shape (84) relative to the needle retention feature (712). The needle retention feature (712) also includes various parts that facilitate coupling of the hollow 3-D arrowhead shape (84) and the needle retention feature (712), as described above.

A difference between the hollow 3-D arrowhead shapes (84) depicted in FIGS. 17-21 and the solid 3-D arrowhead shape (84) depicted in FIGS. 8A-8C is that the hollow 3-D arrowhead shapes (84) depicted in FIGS. 17-21 have a hollow elongate needle proximal portion (102) and a hollow 3-D arrowhead shape (84) with various openings formed thereon. The proximal tip (110) defines a proximal opening (140), which allows communication between an outside of the hollow 3-D arrowhead shape (84) and an interior thereof. The hollow elongate needle proximal portion (102) defines a plurality (e.g., two) of side openings (142), which allow communication between an outside of the hollow elongate needle proximal portion (102) and an interior thereof. The side openings (142) in the hollow elongate needle proximal portion (102) function similarly to the proximal openings (270) in the transfer pipe (46) in FIGS. 11C-11E. The needle joining member (83) defines a side opening (144), which allows communication between an outside of the needle joining member (83) and an interior thereof. The side opening (144) in the needle joining member (83) function similarly to the middle opening (266) in the transfer pipe (46) in FIGS. 11C-11E. The hollow elongate needle proximal portion (102) and the needle joining member (83) may be form from tubes with some rigidity (e.g., hypotubes).

The respective interiors of the hollow 3-D arrowhead shape (84), the hollow elongate needle proximal portion (102), and the needle joining member (83) are in fluid communication with each other. Accordingly, a liquid entering the proximal opening (140) in the hollow 3-D arrowhead shape (84) can travel distally along the respective interiors of the hollow 3-D arrowhead shape (84), the hollow elongate needle proximal portion (102), the needle joining member (83), and the needle distal tip (48) to exit a distal end of the needle spine assembly (76). As such, the needle assembly proximal end assemblies (50) with the hollow 3-D arrowhead shapes (84) depicted in FIGS. 17-21 facilitate transfer of liquids from the proximal medicine chamber (40) to the distal medicine chamber (42) of a dual chamber safe injection system, such as those described herein and in U.S. Utility patent application Ser. No. 15/801,259, filed on Nov. 1, 2017 under Ser. No. 15/801,259 and, entitled "SYSTEM AND METHOD FOR SAFETY SYRINGE," the disclosure of which has been previously incorporated by reference herein.

While the proximal opening (140) in FIG. 17 is at the extreme distal end of the hollow 3-D arrowhead shape (84), in other embodiments, the proximal opening (140) can be anywhere on or adjacent to the hollow 3-D arrowhead shape (84). In one other embodiment (not shown), the proximal opening (140) is formed on the annular distally facing surface (104). In embodiments where the proximal opening (140) is at least partially proximally facing, the edges of the hollow 3-D arrowhead shape (84) that define the proximal opening (140) can be treated (e.g., sand-blasted) to blunt/minimize sharp edges, which may lead to coring/cutting of the distal stopper member (36). Cutting the distal stopper member (36) can lead to fragments thereof being deposited in the injectable liquid, which is undesirable.

Figure 18:
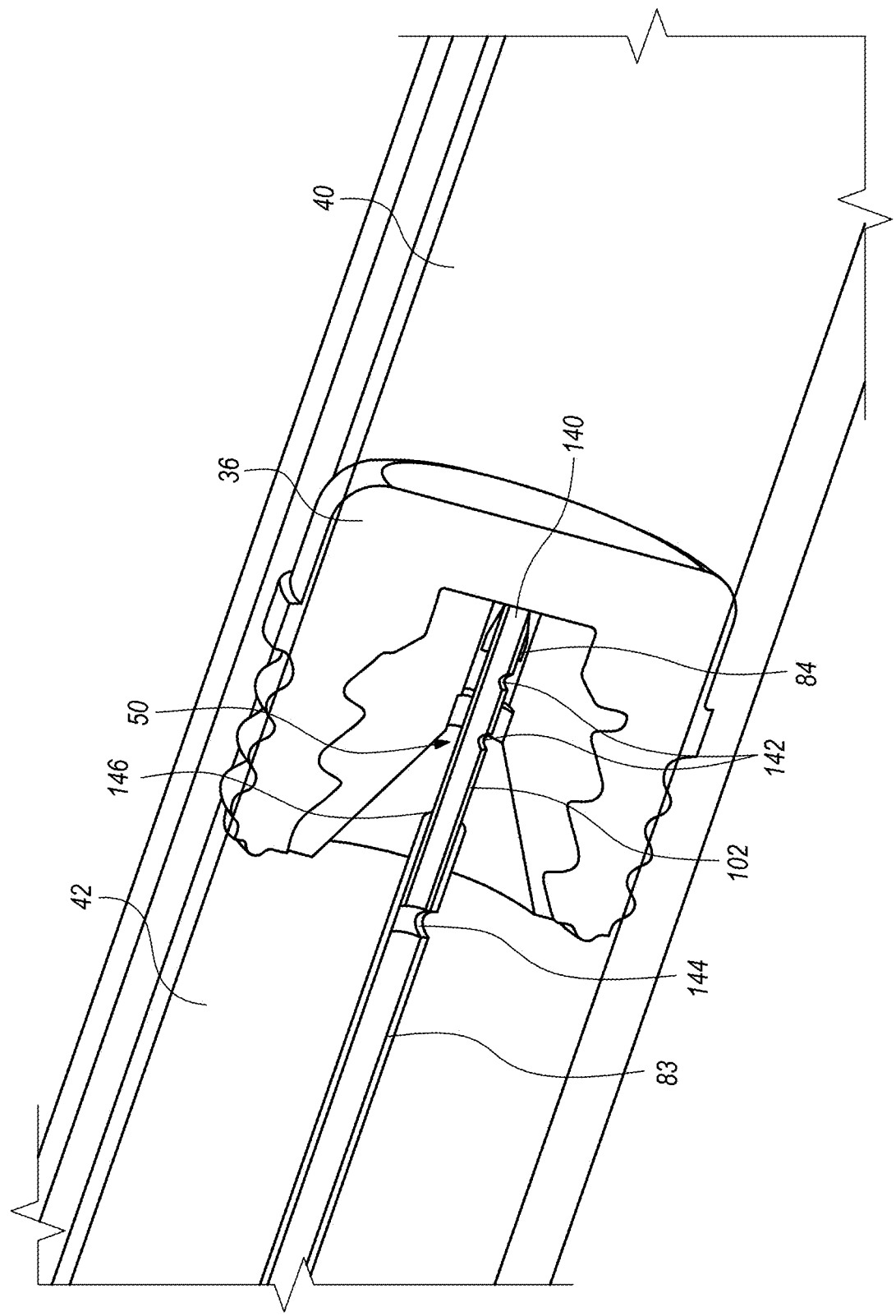

FIG. 18 depicts the hollow 3-D arrowhead shape (84) disposed in the distal stopper member (36) without piercing the distal stopper member (36). As explained above, because the proximal stopper member (32, see FIG. 20) is coupled to the plunger housing member (not shown) and the plunger manipulation interface (not shown), distally directed force applied to the plunger manipulation interface (not shown) will move the proximal stopper member (32) in a distal direction relative to the syringe body (34). Because the proximal medicine chamber (40) is prefilled with a substantially incompressible liquid and because in the transport configuration depicted in FIG. 18 there is no path for the incompressible liquid to escape the proximal medicine chamber (40), distal movement of the proximal stopper member (32) results in distal movement of the distal stopper member (36).

Figure 19:
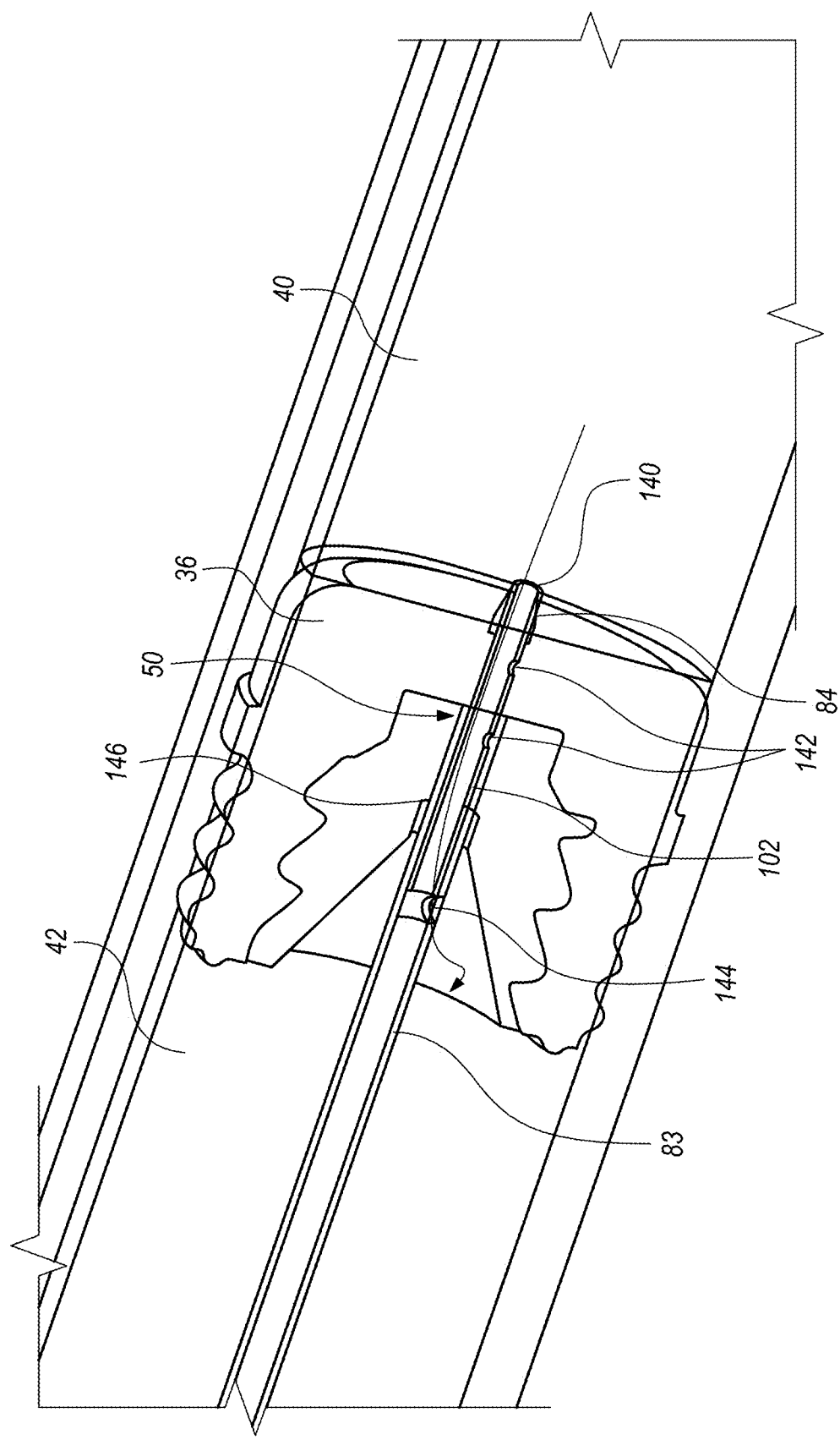

FIG. 19 depicts the relative position of the needle assembly proximal end (50) (including the hollow 3-D arrowhead shape (84), the hollow elongate needle proximal portion (102), and the needle joining member (83)) and the distal stopper member (36) after the distal stopper member (36) has moved distally causing the hollow 3-D arrowhead shape (84) to pierce the distal stopper member (36). A relatively small distal movement of the distal stopper member (36) (e.g., approximately the thickness of a proximal end of the distal stopper member (36)) can start liquid flow through the proximal opening (140) in the hollow 3-D arrowhead shape (84). Minimizing distal motion of the distal stopper member (36) during liquid transfer from the proximal medicine chamber (40) to the distal medicine chamber (42) maximizes the amount of liquid that can be transferred to the distal medicine chamber (42).

FIG. 20 depicts the relative position of the needle assembly proximal end (50) (including the hollow 3-D arrowhead shape (84), the hollow elongate needle proximal portion (102), and the needle joining member (83)) and the proximal and distal stopper members (32, 36) after the proximal stopper member (32) has moved almost all the way to the distal stopper member (36), thereby transferring the majority of the liquid from the proximal medicine chamber (40) to the distal medicine chamber (42). As described above, distal movement of the proximal stopper member (32) is driven by continued application of distally directed force to the plunger manipulation interface (not shown). Because the proximal opening (140) in the hollow 3-D arrowhead shape (84) is occluding by the proximal stopper member (32), liquid moves from the proximal medicine chamber (40) to the distal medicine chamber (42) through the side openings (142) in the hollow elongate needle proximal portion (102).

As shown in FIG. 20, the side opening (144) in the needle joining member (83) is almost occluded by the distal stopper member (36). To prevent the distal stopper member (36) from prematurely occluding the side opening (144) in the needle joining member (83), the needle joining member (83) defines a proximal shoulder (146) that increases the force needed to move an elastic portion of the distal stopper member (36) over the needle joining member (83). The side opening (144) is positioned on the needle joining member (83) such that preventing the elastic portion of the distal stopper member (36) from moving over the needle joining member (83), prevents the distal stopper member (36) from occluding the side opening (144). However, then the proximal and distal stopper members (32, 36) are in contact, the continued application of distally directed force to the plunger manipulation interface (not shown) overcomes the interference from the proximal shoulder (146) and occludes the side opening (144) in the needle joining member (83), thereby prevent backflow of liquid from the distal medicine chamber (42) to the proximal medicine chamber (40). This configuration of the needle assembly proximal end (50) (including the hollow 3-D arrowhead shape (84), the hollow elongate needle proximal portion (102), and the needle joining member (83)) and the proximal and distal stopper members (32, 36) maximizes liquid transfer from the proximal medicine chamber (40) to the distal medicine chamber (42).

Figure 21:
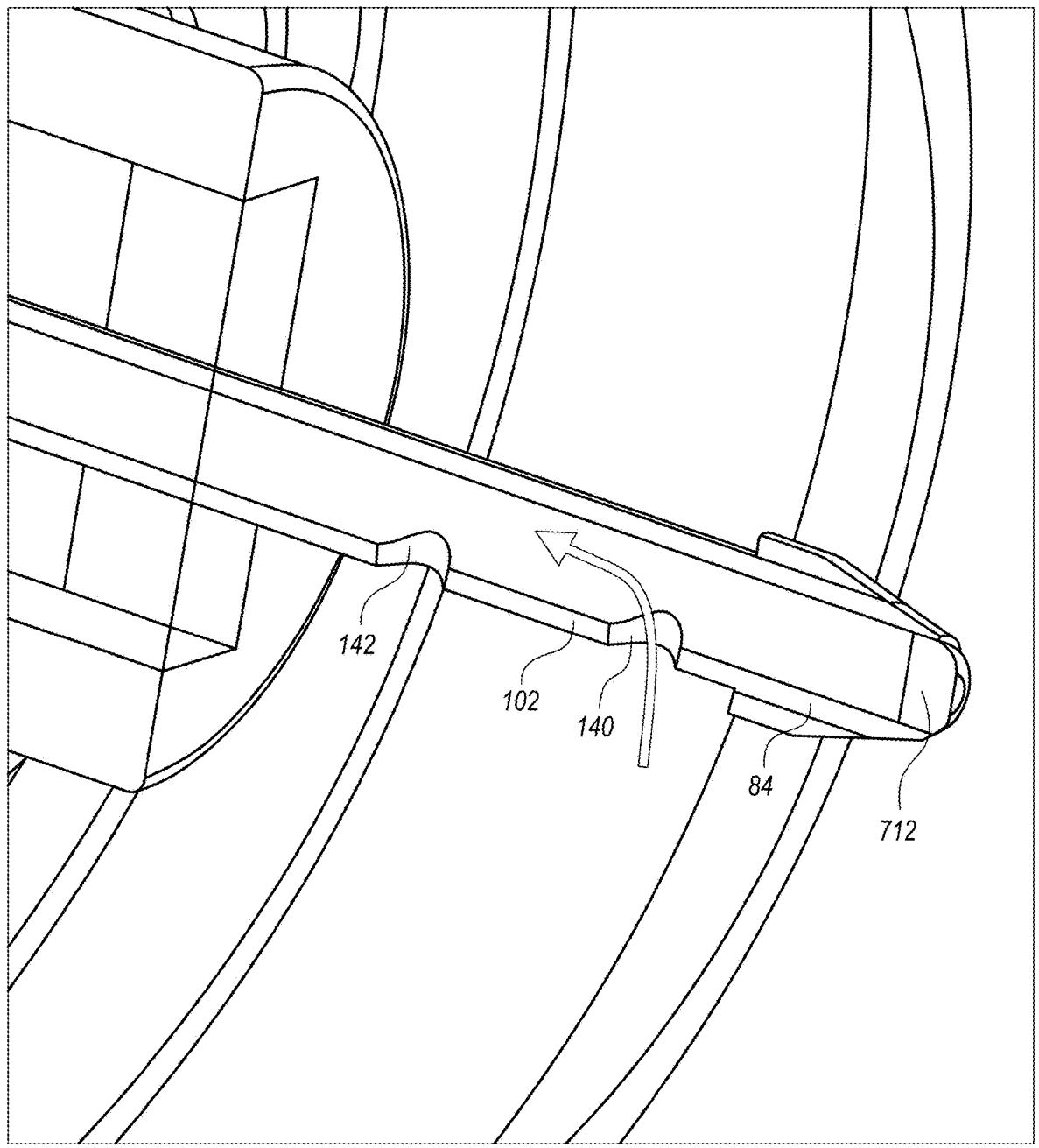

FIG. 21 depicts a hollow 3-D arrowhead shape (84) according to another embodiment. In this embodiment, the extreme proximal end of the hollow 3-D arrowhead shape (84) is welded shut and rounded. This moves the proximal opening (140) to the proximal most opening on the elongate needle proximal portion (102). This change requires the elongate needle proximal portion (102) to penetrate the distal stopper member (36) slightly farther to start liquid transfer compared to the hollow 3-D arrowhead shape (84) depicted in FIG. 17. However, this configuration minimizes the coring/cutting of the distal stopper member (36) problem described above.

The needle assembly proximal end assemblies (50) with the hollow 3-D arrowhead shapes (84) depicted in FIGS. 17-21 and described above facilitate transfer of liquids from the proximal medicine chamber (40) to the distal medicine chamber (42) of a dual chamber safe injection system while also facilitating coupling of the needle assembly proximal end (50) to the needle retention feature (712) for retraction of the needle spine assembly (including the needle assembly proximal end (50)) to a safe position as described above. The hollow 3-D arrowhead shape (84) provides a fluid path from the proximal opening (140) therein to the side opening (144) in the needle joining member (83) for liquid transfer with minimal distal stopper member (36) movement. This maximizes the volume of the distal medicine chamber (42) during liquid transfer and mixing. The hollow 3-D arrowhead shape (84) also provides an annular distally facing surface (104) to securely couple the needle spine assembly (76) to the needle retention feature (712) needle retraction.

While the dual chamber safe injection system with Luer connector embodiments depicted in FIGS. 11A-13G involve cartridges, Luer connectors and the distal needle tip connectors described above can also be used with syringes and other dual chamber safe injection systems. Further, the distal needle tip connectors described above can also be used with single chamber safe cartridge injection systems, such as the system depicted in FIGS. 16A and 16B. The distal needle tip connectors described above are particularly suited for cartridge injection systems, because the needle distal tip (48) may be pulled through a plurality of seals (e.g., backup seal (132) and cartridge seal (130)) in addition to a stopper member (not shown) in such systems.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injecting, comprising:
    a syringe body defining a proximal opening and a distal needle interface;
    a plunger member defining a plunger interior and configured to be manually manipulated to insert a stopper member relative to the syringe body, the plunger member including
        a needle retention feature disposed in the plunger interior,
        an energy-storage member disposed in the plunger interior, and
        an energy-storage member latching member disposed in the plunger interior; and
    a needle hub assembly coupled to the distal needle interface of the syringe body, the needle hub assembly including
    a needle having a needle proximal end feature comprising an elongate needle proximal portion, a collar portion, and a proximal tip,
        a hub, and
        a needle latching member configured to couple the needle to the hub,
    wherein the needle is at least partially retractable into the plunger interior upon manipulation of the plunger member relative to the syringe body to transform the energy-storage member latching member from a latched state to an unlatched state,
    wherein the energy-storage member latching member is intercoupled between an interior surface of the plunger member and the needle retention feature,
    wherein the elongate needle proximal portion has a substantially constant first cross-sectional diameter,
    wherein the collar portion has a second cross-sectional diameter, and
    wherein the second cross-sectional diameter is greater than the first cross-sectional diameter,
    wherein the collar portion comprises an annular distally facing surface,
    wherein the needle retention feature comprises a receiving member having a plurality of latching members to cooperate with the annular distally facing surface to prevent distal movement of the needle relative to the needle retention feature, when the needle is coupled to the needle retention feature, and
    wherein the receiving member has a rigid ring disposed at a distal end thereof.

2. The system of claim 1, wherein the needle is configured to pierce through the stopper member to initiate needle retraction.

3. The system of claim 1, wherein the annular distally facing surface is configured to prevent distal movement of the needle relative to the needle retention feature, when the needle is coupled to the needle retention feature.

4. The system of claim 1, wherein the plurality of latching members consists of two latching members, and
    wherein each of the two latching members has an arcuate cross-sectional geometry.

5. The system of claim 1, wherein the plurality of latching members consists of four latching members.

6. The system of claim 1, the receiving member also having a plurality of slits, wherein each slit of the plurality of slits is disposed between two latching members of the plurality of latching members.

7. The system of claim 1, wherein the elongate needle proximal portion consists of a solid body.

8. The system of claim 1, wherein the proximal tip of the needle has a third cross-sectional diameter, and
    wherein the first cross-sectional diameter is greater than the third cross-sectional diameter.

9. The system of claim 1, the needle proximal end feature further comprising a proximally directed tapering surface.

10. The system of claim 9, wherein the proximally directed tapering surface defines a proximally pointed cone.

11. The system of claim 1, wherein the needle proximal end feature includes a proximal opening and a hollow interior.

12. The system of claim 11, wherein the needle comprises a tubular member coupled to the proximal end feature such that an interior of the tubular member is in fluid communication with the hollow interior of the needle proximal end feature, and
    wherein the tubular member includes a side opening.

13. The system of claim 11, the needle comprising a shoulder configured to increase a distal force required to push the stopper member over the needle.

14. The system of claim 11, wherein the proximal opening is defined by blunted edges of the needle proximal end feature.

15. The system of claim 1, the receiving member having an open configuration in which the needle proximal end feature can move proximally past the receiving member and a resting configuration in which the needle proximal end feature cannot move distally past the receiving member,
    wherein the plurality of latching members are closer to each other when the receiving member is in the resting configuration than when the receiving member is in the open configuration.

16. The system of claim 15, wherein the plurality of latching members are biased to move closer to each other such that the receiving member is in the resting configuration.

17. The system of claim 15, wherein the plurality of latching members are configured to move away from each other when the needle proximal end feature is moved proximally past the receiving member to place the receiving member in the open configuration.

18. The system of claim 17, wherein the plurality of latching members are biased to move closer to each other when the needle proximal end feature has moved past the receiving member in a proximal direction such that the receiving member is returned to the resting configuration, such that an interaction between the plurality of latching members and the annular distally facing surface of the needle proximal end feature prevents distal movement of the needle relative to the needle retention feature.

\* \* \* \* \*